United States Patent

Sugiura et al.

Patent Number: 5,116,869
Date of Patent: May 26, 1992

[54] 2-SUBSTITUTED-2-CYCLOPENTENONES

[75] Inventors: Satoshi Sugiura; Atsuo Hazato; Toru Minoshima; Yoshinori Kato, all of Hino; Yasuko Koshihara, Kawaguchi; Seizi Kurozumi, Kokubunji, all of Japan

[73] Assignee: Teijin Limited, Osaka, Japan

[21] Appl. No.: 759,785

[22] Filed: Sep. 3, 1991

Related U.S. Application Data

[63] Continuation of Ser. No. 340,207, Apr. 19, 1989, abandoned.

[30] Foreign Application Priority Data

Apr. 19, 1988 [JP] Japan .................. 63-94687
Jan. 24, 1989 [JP] Japan .................. 1-13036

[51] Int. Cl.$^5$ ............................. A61K 31/35
[52] U.S. Cl. .................. 514/456; 514/460; 514/473; 514/530; 514/546; 514/548; 514/570; 514/572; 514/573; 514/684; 514/690; 514/691; 549/284; 549/285; 549/414; 549/415; 549/416; 549/421; 549/422; 549/423; 549/473; 549/475; 556/427; 556/428; 560/9; 560/11; 560/15; 560/17; 560/18; 560/106; 560/107; 560/108; 560/109; 560/116; 560/118; 560/121; 560/122; 560/142; 560/231; 560/254; 560/255; 562/426; 562/429; 562/431; 562/432; 562/503; 562/504; 568/29; 568/31; 568/36; 568/37; 568/42; 568/43

[58] Field of Search ............ 549/284, 285, 414, 415, 549/416, 421, 422, 423, 473, 475; 556/427, 428; 560/9, 11, 15, 17, 18, 106, 107, 108, 109, 116, 118, 121, 122, 142, 231, 254, 255; 562/426, 429, 431, 432, 503, 504; 568/29, 31, 36, 37, 42, 43; 514/456, 460, 473, 530, 546, 548, 570, 572, 573, 684, 690, 691

[56] References Cited

FOREIGN PATENT DOCUMENTS

| | | |
|---|---|---|
| 0106576 | 4/1984 | European Pat. Off. |
| 0131441 | 1/1985 | European Pat. Off. |
| 0180399 | 5/1986 | European Pat. Off. |
| 53-90246 | 8/1978 | Japan ................. 568/43 |
| 56-15236 | 2/1981 | Japan ................. 568/43 |
| 58-216155 | 12/1983 | Japan . |
| 59-59646 | 4/1984 | Japan . |
| 59-184158 | 10/1984 | Japan . |
| 60-4129 | 1/1985 | Japan . |
| 62-96438 | 5/1987 | Japan . |
| WO85/03706 | 8/1985 | PCT Int'l Appl. |
| 87/04189 | 7/1987 | PCT Int'l Appl. |
| 632992 | 11/1982 | Switzerland . |

OTHER PUBLICATIONS

J. Amer. Chem. Soc., 95, 6831 (1973).
Biochem. Biophys. Res. Commun., 87, 795 (1979).
Prostaglandins and Cancer: First International Conference, 365-368 (1982).
Proc. Natl. Acad. Sci., 81, 1317-1321 (1984).
Tetrahedron Lett., 23, 5171 (1982).
Tetrahedron Lett., 23, 5331 (1987).
Cancer and Chemotherapy, 10, 1930, (1983), (and English Summary), p. 3, lines 14-15.
J. Am. Chem. Soc., 106, 3384 (1984).
Tetrahedron Letters, 25, 33, 3621-3624 (1984).
J. of American Chemical Society, 107, 2976 (1985).
Proceedings of the Japanese Cancer Association, Collected Abstracts of the 43rd Meeting of Japanese Society of Cancer, p. 258 (1984).
Biochemical Society of Japan, (Collected Abstracts, p. 767, 1988), (and English Summary), p. 7, lines 21-22.

*Primary Examiner*—Bruce Gray
*Attorney, Agent, or Firm*—Sughrue, Mion, Zinn, Macpeak & Seas

[57] ABSTRACT

2-Substituted-2-cyclopentenones represented by the formula (I):

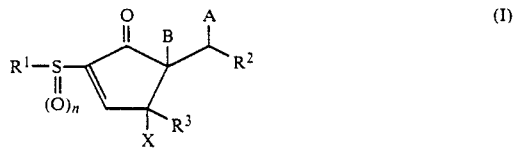

wherein A is a hydroxyl group or

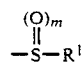

and B is a hydrogen atom or A and B are bonded together to form one bonding arm;
$R^1$ represents a substituted or unsubstituted hydrocarbon group having 1 to 10 carbon atoms;
$R^2$ represents a substituted or unsubstituted aliphatic hydrocarbon group having 1 to 10 carbon atoms;
$R^3$ represents a substituted or unsubstituted aliphatic hydrocarbon group having 1 to 10 carbon atoms; wherein,
when $R^3$ is a single bond bonded to the cyclopentene skeleton, X represents a hydrogen atom, a hydroxyl group or a protected hydroxyl group; and
when $R^3$ is a double bond bonded to the pentene skeleton, X represents a bonding arm constituting a part of said double bond; and
m and n independently represent 0, 1 or 2.

17 Claims, No Drawings

2-SUBSTITUTED-2-CYCLOPENTENONES

This is a continuation of application Ser. No. 07/340,207, filed Apr. 19, 1989 now abandoned.

BACKGROUND OF THE INVENTION

1. Field of the Invention

The present invention relates to novel 2-substituted-2-cyclopentanones. More specifically, the present invention relates to 2-substituted-2-cyclopentenones having pharmacological activities such as an excellent antitumor activity, and an excellent bone formation acceleration activity, and to an anti-tumor agent and a bone formation accelerator.

2. Description of the Related Art

Prostaglandins are compounds having specific biological activities such as platelet aggregation inhibitory activities and hypotensive activities, and are naturally occurring substances which are useful as therapeutical agents for peripheral circulatory organ system diseases in current medical treatments. Among these prostaglandins, prostaglandins A are known to have a double bond in the cyclopentane ring; for example, prostaglandin $A_2$ is considered to be a medicament having hypotensive activities (see E. J. Corey et al, J. Amer. Chem. Soc., 95, 6831, 1973).

Also, since prostaglandins A inhibit potential DNA synthesis, the possibility of using prostaglandins A as an antitumor agent has been reported (see Biochem. Biophys. Res. Commun., 87, 795, 1979; W. A. Turner et al, Prostaglandins and Cancer: First International Conference 365-368, 1982.

European Unexamined Published Patent Publication No. 0106576 (published on Apr. 25, 1984), disclosed 4,5-substituted 2-cyclopentenones including prostaglandins A, among which are 5-alkylidene-4-substituted-2-cyclopentenones represented by the formula:

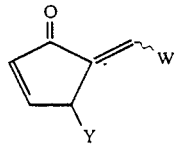

wherein W represents a hydrocarbon group having 1 to 12 carbon atoms which also may be substituted, and Y represents a hydrocarbon group having 1 to 12 carbon atoms which also may be substituted and 5-(1-hydroxyhydrocarbon)-4-substituted-2-cyclopentenones of the formula:

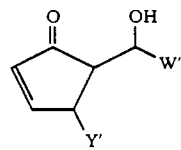

wherein W' and Y' are the same as W and Y, respectively. Further, it is disclosed that these compounds are useful for the treatment of malignant tumors.

Also, European Unexamined Published Patent Publication No. 0131441 (published on Jan. 16, 1985), disclosed 5-alkylidene-2-halo-4-substituted-2-cyclopentenones of the formula:

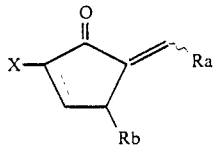

wherein Ra represents a substituted or non-substituted hydrocarbon having 1 to 12 carbon atoms or a substituted or non-substituted phenyl group; Rb represents a substituted or non-substituted hydrocarbon having 1 to 12 carbon atoms; and X represents a halogen atom, and further, that these compounds are similarly effective for the treatment of malignant tumors.

Further, prostaglandins D and J different from prostaglandins A are known to be useful as antitumor agents (Japanese Unexamined Patent Publication (Kokai) 58-216155 and proceedings of the National Academy of Sciences of the United States of America (Proc. Natl. Acad. Sci. U.S.A.), 81, 1317-1321, 1984).

Also, prostaglandin analogues represented by the formula:

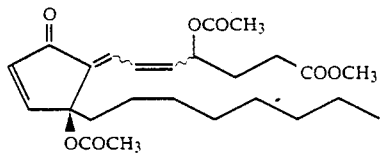

and isolated from coral produced in Okinawa [Okinawa soft coral: clavularia viridis] are known to have an antiinflammatory activity and antitumor activity as physiological activities thereof [see Kikuchi et al, Tetrahedron Lett., 23, 5171, 1982; Kobayashi et al, Tetrahedron Lett., 23, 5331, 1982; Masanori Fukushima, Cancer and Chemotherapy, 10, 1930, 1983).

Japanese Unexamined Patent Publication (Kokai) No. 59-59646 disclosed culavulon derivatives including the above natural products of the formula:

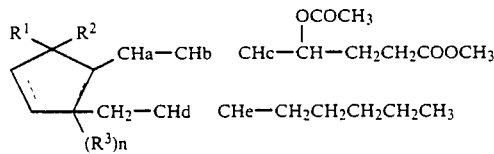

$R^1$ and $R^2$ together represent a keto group, or one thereof is a hydrogen group and the other is hydroxy group, $R^3$ is a hydrogen atom or acetoxy group, n is 0 or 1, n being 0 when there is a double bond between the positions 8 and 12, a, b, c, d, and e are each 1 or 2, and the dotted line denotes a single bond or double bond between c and d, and that these compounds are useful as antiinflammatory agents.

Japanese Unexamined Patent Publication (Kokai) No. 59-184158 disclosed, as a compound having a similar antiinflammatory activity, culavulon derivatives of the formula:

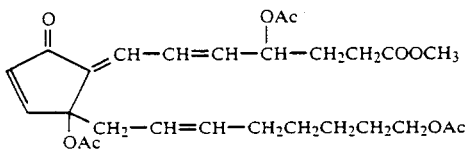

wherein Ac denotes an acetyl group.

Japanese Unexamined Patent Publication (Kokai) No. 60-4129 disclosed that the culavalon derivatives included in the above two formulae are useful as antitumor agents.

E. J. Corey et al synthesized the culavalon derivatives represented by the following formula:

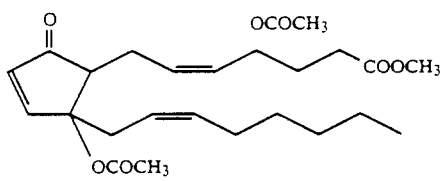

(Journal of the American Chemical Society (J. Am. Chem. Soc.), 106, 3384, 1984).

Nagaoka et al similarly synthesized culavulon derivatives represented by the following formula:

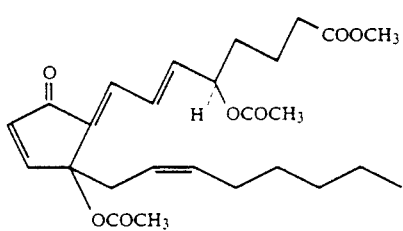

(Tetrahedron Letters, vol. 25, No. 33, pages 3621–3624, 1984).

Further, recently, punaglandins 1 and 2 represented by the formula:

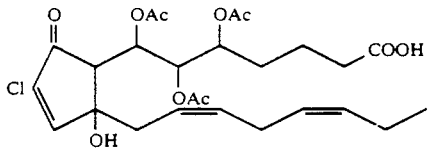

and the formula:

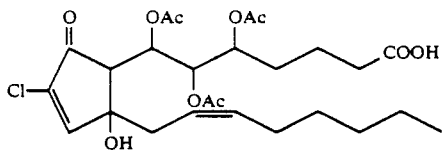

were isolated from Telesto riisei growing on a ship's bottom at Oaf island. B. J. Baker, J. of American Chem. Soc., 107, 2976, 1985.

Also, published PCT Patent Application No. WO85-03706 (publication date: Aug. 29, 1985) disclosed punaglandins represented by the following formula:

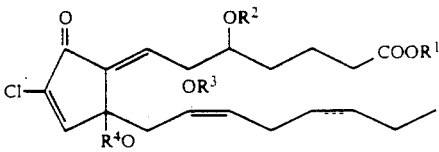

wherein $R^1$ resents a hydrogen atom, $C_1$–$C_{10}$ an alkyl group or one equivalent cation, $R^2$, $R^3$, $R^4$ may be the same or different, and each represents a hydrogen atom or $C_2$–$C_{10}$ acyl group, and the representation ⚌ denotes a single bond or double bond, and that these punaglandins are useful for the therapy of malignant tumors.

Masanori Fukushima et al reported that the compounds of the following formula included in the above formula:

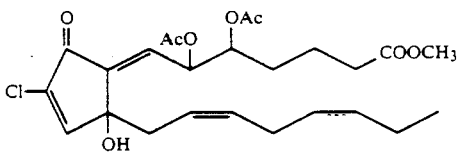

have an antitumor activity (see Masanori Fukushima et al collected abstracts of the 43rd Meeting of Japanese Society of Cancer, p. 258, 1984).

Further, Japanese Unexamined Patent Publication (Kokai) No. 62-96438 disclosed 4-hydroxy-2-cyclopentenones which are culavulon analogues and punaglandin analogues of the formula:

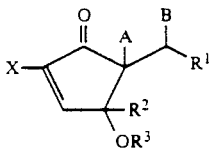

wherein X represents a hydrogen atom or a halogen atom; A and B represent a combination of A which is a hydrogen atom and B which is a hydroxyl group or A and B are bonded mutually to represent one bonding arm; $R^1$ represents a substituted or non-substituted alkyl group, and an alkenyl group or alkynyl group having 1 to 10 carbon atoms; $R^2$ represents a substituted or non-substituted alkyl, alkenyl or alkynyl group having 1 to 10 carbon atoms; and $R^3$ represents a hydrogen atom or a protective group for a hydroxyl group; with the proviso that $R^2$ cannot be 2-octenyl, 8-acetoxy-2-octenyl or 2,5-octadienyl and that these compounds are useful for the therapy of malignant tumors.

Furthermore, the bone metabolism of an average healthy human is considered to be valid when a good balance is maintained between repeated bone resorption with an osteoclast and bone formation with an osteoblast, and when this balance between bone resorption and bone formation is disturbed, diseases such as osteoporosis or osteomalacia may occur. As the therapeutical agents for such bone diseases, active type vitamin preparations, calcitonin preparations, diphosphonic acid preparations, estrogen preparations, and calcium preparations may be employed, but although many of these preparations have been reported to inhibit bone resorption, etc., none have clearly manifested an effect of accelerating bone formation. Further, the effects of these preparations are uncertain, and accordingly, there is a strong demand for the development of a drug which causes an acceleration of bone formation with osteoblast, without uncertainty about the effects thereof.

Koshihara et al. found that prostaglandin $D_2$ has a calcification accelerating activity on human osteoblast, as reported in the Biochemical Society of Japan (Collected abstracts, p. 767, 1988), thought to be caused by the activity of $\Delta^{12}$-prostaglandin $J_2$ formed by a decomposition of prostaglandin $D_2$. Nevertheless, a bone acceleration activity of the 2-substituted-2-cyclopentanones is not known.

SUMMARY OF THE INVENTION

Accordingly, an object of the present invention is to obviate the above-mentioned problems in the prior art and to provide novel 2-substituted-2-cyclopentenones, namely 2-cyclopentenones substituted at the 2-position with a sulfur atom.

Another object of the present invention is to provide 2-substituted-2-cyclopentenones having a remarkable antitumor activity.

A further object of the present invention is to provide 2-substituted-2-cyclopentenones having a remarkable bone formation accelerating activity.

A still further object of the present invention is to provide a process for producing 2-substituted-2-cyclopentenones of the present invention.

Other objects and advantages of the present invention will be apparent from the description set forth hereinbelow.

In accordance with the present invention, there is provided 2-substituted-2-cyclopentenones represented by the formula (I):

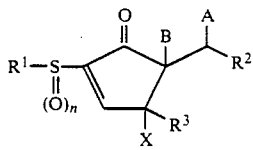

(I)

wherein A is a hydroxyl group or

and B is a hydrogen atom or A and B are bonded together to form one bonding arm;

$R^1$ represents a substituted or unsubstituted hydrocarbon group having 1 to 10 carbon atoms;

$R^2$ represents a substituted or unsubstituted aliphatic hydrocarbon group having 1 to 10 carbon atoms;

· $R^3$ represents a substituted or unsubstituted aliphatic hydrocarbon group having 1 to 10 carbon atoms; wherein, when $R^3$ is a single bond bonded to the cyclopentene skeleton, X represents a hydrogen atom, a hydroxyl group or a protected hydroxyl group; and when $R^3$ is a double bond bonded to the pentene skeleton, X represents a bonding arm constituting a part of said double bond; and m and n independently represent 0, 1 or 2.

DESCRIPTION OF THE PREFERRED EMBODIMENT

In the above formula (I), A and B represent a combination of A which is a hydroxyl group or

and B is a hydrogen atom or A and B are bonded together to represent one bonding arm. That is, when A is a hydroxyl group and B is a hydrogen group, the above formula (I) represents 2-substituted-2-cyclopentenones represented by the following formula (I-b'):

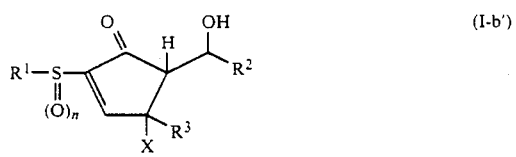

(I-b')

wherein $R^1$, $R^2$, $R^3$, X and n are as defined above; when A is

and B is a hydrogen atom, the above formula (I) represents 2-substituted-2-cyclopentanones represented by the following formula (I-b''):

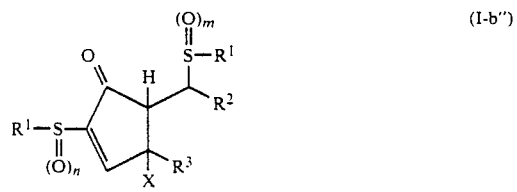

(I-b'')

wherein $R^1$, $R^2$, $R^3$, X, m and n are as defined above; when A and B are bonded together to represent one bonding arm, the above formula (I) represents 2-substituted-2-cyclopentenones represented by the following formula (I-a):

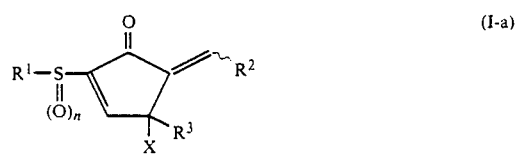

(I-a)

wherein $R^1$, $R^2$, $R^3$, X and n are as defined above, and the representation $\sim$ denotes that the substituent bonded to the double bond is in an E-configuration or a Z-configuration or a mixture thereof at any desired ratio.

In the above formula (I), $R^1$ represents a substituted or non-substituted hydrocarbon group having 1 to 10 carbon atoms. Examples of the non-substituted hydrocarbon group having 1 to 10 carbon atoms include alkyl groups such as methyl, ethyl, propyl, isopropyl butyl, isobutyl, s-butyl t-butyl, pentyl, isopentyl, neopentyl, hexyl, heptyl, octyl, nonyl, decyl and the like; aralkyl groups such as benzyl, phenetyl, phenylpropyl, phenyl-butyl and the like; or aryl groups such as phenyl, p-tolyl, 1-naphthyl, 2-naphthyl groups, and the like. The hyarocarbon group may be substituted with a plural different substitution groups. The substituents on such hydrocarbon groups include a hydroxyl group; tri(C$_1$-C$_7$)hydrocarbonsilyloxy groups such as trimethylsilyloxy, triethylsilyloxy, t-butyldimethylsilyloxy, t-butyldiphenylsilyloxy, and tribenzylsilyloxy groups; halogen atoms such as fluorine, chlorine, and bromine; alkoxy groups such as methoxy and ethoxy groups; acyloxy groups such as acetyloxy and propanoyl groups; and acyl groups such as acetyl and propionyl groups; alkoxycarbonyl groups such as methoxycarbonyl, ethoxycarbonyl, and propoxycarbonyl; and carboxyl group. Preferably R$^1$ represents alkyl groups having 1 to 5 carbon atoms such as methyl, ethyl, propyl, butyl, and pentyl groups, and phenyl groups, particularly preferably, a methyl group.

In the above formula (I), m and n are the same or different and represent 0, 1 or 2. The substituent

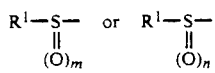

represents a hydrocarbonthio group when m or n is 0, a hydrocarbonsulfinyl group when m or n is 1, and a hydrocarbonsulfonyl group when m or n is 2.

In the above formula (I), R$^2$ represents a substituted or non-substituted aliphatic hydrocarbon group having 1 to 10 carbon atoms. Examples of the non-substituted aliphatic hydrocarbon group having 1 to 10 carbon atoms include alkyl groups such as methyl, ethyl, propyl, isopropyl, butyl, isobutyl, s-butyl, t-butyl, pentyl, isopentyl, neopentyl, hexyl, heptyl, octyl, 3,7-dimethyloctyl, nonyl or decyl groups; alkenyl groups such as vinyl, 1-propenyl 2-propenyl, 1-butenyl, 1,3-butadienyl, 2-butenyl, 1-pentenyl, 2-pentenyl, 1-hexenyl, 2-hexenyl, 1,5-hexadienyl, 3-hexenyl, 1-heptenyl, 1-octenyl, 1,7-octadienyl, 1-nonenyl or 1-decenyl groups; and alkynyl groups such as ethynyl, 1-propynyl, 2-propynyl, 1-butynyl, 3-buten-1-ynyl, 2-butynyl, 1-pentynyl, 2-pentynyl, 1-hexynyl, 2-hexynyl, 5-hexen-1-ynyl, 3-hexynyl, 1-heptynyl, 1-octynyl, 7-octen-1-ynyl, 1-nonynyl or 1-decynyl groups. The aliphatic hydrocarbon group may be substituted with plural different substitution groups. The substituent on such aliphatic hydrocarbon groups includes —COOR$^5$ (wherein R$^5$ represents a hydrogen atom, an alkyl group having 1 to 10 carbon atoms or one equivalent cation); —OR$^6$ (wherein R$^6$ represents a hydrogen atom; an acyl group having 2 to 7 carbon atoms; a tri(C$_1$-C$_7$)hydrocarbonsilyl group; a group which forms an acetal bond together with the oxygen atom to which R$^6$ is bonded; an aromatic hydrocarbon group which may be substituted with a halogen atom, a hydroxyl group, a tri(C$_1$-C$_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a hydroxyl group a tri(C$_1$-C$_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms; or an alicyclic group which may be substituted with a halogen atom, a hydroxyl group, a tri(C$_1$-C$_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, or an alkoxy group having 1 to 4 carbon atoms. Examples of R$^5$ in —COOR$^5$ include a hydrogen atom; alkyl groups having 1 to 10 carbon atoms such as methyl, ethyl, propyl, isopropyl, butyl, s-butyl, t-butyl, pentyl, neopentyl, hexyl, heptyl, octyl, nonyl or decyl groups; one equivalent cation such as cations of ammonium, tetramethyl ammonium, monomethyl ammonium, dimethyl ammonium, trimethyl ammonium, benzyl ammonium, and phenetyl ammonium, or a morpholinium cation, piperidinium cation or Na$^+$, K$^+$, ½Ca$^{2+}$, ½Mg$^{2+}$, ½Zn$^{2+}$, ⅓Al$^{3+}$. Preferably, R$^5$ represents a hydrogen atom, methyl group, and ethyl group.

Examples of R$^6$ in —OR$^6$ include a hydrogen atom; acyl groups having 2 to 7 carbon atoms such as acetyl, propionyl, butyryl, isobutyryl, valeryl, isovaleryl, hexanoyl, heptanoyl, and benzoyl groups; tri(C$_1$-C$_7$)hydrocarbonsilyl groups such as trimethylsilyl, triethylsilyl, t-butyldimethylsilyl, t-butyldiphenylsilyl, and tribenzylsilyl groups; and groups which form an acetal bond together with the oxygen atom to which R$^6$ is bonded such as methoxymethyl, 1-ethoxyethyl, 2-methoxy-2-propyl, 2-ethoxy-2-propyl, 2-methoxyethoxymethyl, tetrahydropyran-2-yl, tetrahydrofuran-2-yl, and 6,6-dimethyl-3-oxa-2-oxo-bicyclo[3.1.0]-hexan-4-yl groups. Examples of the aromatic hydrocarbons which may be substituted with a halogen atom, a hydroxyl group, a tri(C$_1$-C$_7$)hydrocarbonsilyloxy group, a carboxyl group, an acyloxy group having 2 to 7 carbon atoms, an acyl group having 2 to 7 carbon atoms an alkoxycarbonyl group having 2 to 5 carbon atoms, or an alkyl group having 1 to 4 carbon atoms are phenyl, 1-naphthyl, 2-naphthyl, and 1-anthranyl. Examples of the substituent are a halogen atom such as fluorine, chlorine, and bromine; a hydroxyl group; tri(C$_1$-C$_7$)hydrocarbonsilyloxy groups such as trimethylsilyloxy, triethylsililoxy, t-butyldimethylsilyloxy, t-butyldiphenylsililoxy, and tribenzylsilyloxy groups; a carboxyl group; an acyloxy groups such as acetoxy, propionyloxy, butyryloxy, isobutyryloxy, valeryloxy, isovaleryloxy, hexanoyloxy, heptanoyloxy, and benzoyloxy groups; acyl groups such as acetyl, propionyl, butyryl, isobutyryl, valeryl, isovaleryl, hexanoyl, heptanoyl, and benzoyl groups; alkoxycarbonyl groups such as methoxycarbonyl, ethoxycarbonyl, propoxycarbonyl, isopropoxycarbonyl, butoxycarbonyl, isobutoxycarbonyl, and s-butoxycarbonyl groups; alkyl groups such as methyl, ethyl, propyl, isopropyl, butyl, isobutyl, s-butyl, and t-butyl groups; and alkoxy groups such as methoxy, ethoxy, propoxy, isopropoxy, butoxy, isobutoxy, s-butoxy, and t-butoxy groups. Particularly preferably, R$^6$ represents a hydrogen atom, acetyl group, trimethylsilyl group, t-butyldimethylsilyl group, tetrahydropiran-2-yl group, and phenyl group.

Examples of the aromatic hydrocarbon group and the substituent, when the substituent group of R$^2$ is an aromatic hydrocarbon group which may be substituted with a halogen atom, a hydroxyl group, tri(C$_1$-C$_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, or an alkoxy group having 1 to 4 carbon atoms, are those as mentioned in the case of $R^6$. Preferable substituents are phenyl, 3,4-dimethoxyphenyl, and 4-methoxycarbonylphenyl.

When $R^2$ is an alicyclic hydrocarbon group having 4 to 10 carbon atoms which may be substituted with a halogen atom, a hydroxyl group, tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, or an alkoxy group having 1 to 4 carbon atoms, examples of such an alicyclic group are cyclobutyl, cyclopentyl, cyclohexyl, 1-cyclohexenyl, 3-cyclohexenyl, 4-cyclohexenyl, cycloheptyl, cyclooctyl, bicyclo[4.4.0]decane-2-yl groups and examples of the substituent are halogen atoms such as fluorine, chlorine, and bromine; a hydroxyl group; tri($C_1$-$C_7$)hydrocarbonsilyloxy groups such as trimethylsililoxy, triethylsililoxy, t-butyldimethylsilyloxy, t-butyldiphenylsililoxy, and tribenzylsilyloxy groups; a carboxyl group; acyloxy groups such as acetoxy, propionyloxy, butyryloxy, isobutyryloxy, valeryloxy, isovaleryloxy, hexanoyloxy, heptanoyloxy, and benzoyloxy groups; acyl groups such as acetyl, propionyl, butyryl, isobutyryl, valeryl, isovaleryl, hexanoyl, heptanoyl, and benzoyl groups; alkoxycarbonyl groups such as methoxycarbonyl, ethoxycarbonyl, propoxycarbonyl, isopropoxycarbonyl, butoxycarbonyl, isobutoxycarbonyl, and s-butoxycarbonyl groups; alkyl groups such as methyl, ethyl, propyl, isopropyl, butyl, isobutyl, s-butyl, t-butyl groups; and alkoxy groups such as methoxy, ethoxy, propoxy, isopropoxy, butoxy, isobutoxy, s-butoxy, and t-butoxy groups. Particularly preferably, 4-hydroxycyclohexyl, 3,5-diacetoxycyclohexyl, cyclopentyl, and 3-ethylcyclopentyl can be exemplified.

In the above formula (I), $R^3$ represents a substituted or non-substituted aliphatic hydrocarbon group having 1 to 10 carbon atoms, and when $R^3$ is bonded through a single bond to the cyclopentene skeleton, X represents a hydrogen atom, a hydroxyl group or a protected hydroxyl group, and when $R^3$ is bonded through a double bond to the cyclopentene skeleton, X represents a part of said double bond. More specifically, when $R^3$ is bonded through a single bond to the cyclopentene skeleton, the above formula (I) represents 2-substituted-2-cyclopentenones represented by the following formula (I'):

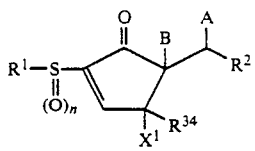

wherein A, B, $R^1$, $R^2$ and n are as defined above; $R^{34}$ represents a substituted or non-substituted aliphatic hydrocarbon group having 1 to 10 carbon atoms; $X^1$ represents a hydrogen atom, hydroxyl group or a protected hydroxyl group]; when $R^3$ is bonded through a double bond to the cyclopentene skeleton and X represents a bond in said double bond, the above formula (I) represents 2-substituted-2-cyclopentenones represented by the following formula (I''):

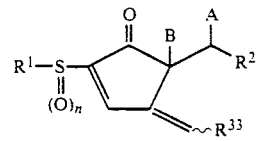

wherein A, B, $R^1$, $R^2$, n and the representation $\sim$ are as defined above; $R^{33}$ represents a hydrogen atom or a substituted or non-substituted aliphatic hydrocarbon group having 1 to 9 carbon atoms.

$R^{34}$ in the above formula (I') represents a substituted or non-substituted aliphatic hydrocarbon group having 1 to 10 carbon atoms, and examples of such $R^{34}$ include the same groups as mentioned above for $R^2$, also including the substituents.

$X^1$ in the above formula (I') represents a hydrogen atom, hydroxyl group or a protected hydroxyl group, and examples of the protected hydroxyl group include alkoxy groups such as methoxy, ethoxy, propoxy, and isopropoxy; tri($C_1$-$C_7$)hydrocarbonsilyloxy groups such as trimethylsilyloxy, triethylsilyloxy, t-butyldimethylsilyloxy, t-butyldiphenylsilyloxy, and tribenzylsilyloxy groups; acetal groups such as methoxymethoxy, 1-ethoxyethoxy, 2-methoxyethoxymethoxy, and tetrahydropyran-2-yloxy groups; and acyloxy groups such as acetoxy, propionyloxy, and butyryloxy groups. Preferably, $X^1$ represents a hydrogen atom, hydroxyl group, methoxy group, ethoxy group, trimethylsilyloxy group, and acetoxy group.

$R^{33}$ in the above formula (I'') represents a substituted or non-substituted aliphatic hydrocarbon group having 1 to 9 carbon atoms and examples of the substituent for such $R^{33}$ include the same substituents as mentioned above for $R^2$. Examples of the non-substituted aliphatic hydrocarbon group having 1 to 9 carbon atoms of $R^{33}$ include alkyl groups such as methyl, ethyl, propyl, isopropyl, butyl, isobutyl, s-butyl, t-butyl, pentyl, isopentyl, neopentyl, hexyl, heptyl, octyl or nonyl groups; alkenyl groups such as vinyl, 1-propenyl, 2-propenyl, 1-butenyl, 1,3-butadienyl, 2-butenyl, 1-pentenyl, 2-pentenyl, 1-hexenyl, 2-hexenyl, 1,5-hexadienyl, 3-hexenyl, 1-heptenyl, 2,6-dimethylheptenyl, 1-octenyl, 1,7-octadienyl or 1-nonenyl groups; and alkynyl groups such as ethynyl, 1-propynyl, 2-propynyl, 1-butynyl, 3-buten-1-ynyl, 2-butynyl, 1-pentynyl, 2-pentynyl, 1-hexynyl, 2-hexynyl, 5-hexen-1-ynyl, 3-hexynyl, 1-heptynyl, 1-octynyl, 7-octen-1-ynyl or 1-nonynyl groups.

Examples of 2-substituted-2-cyclopentenones of the present invention represented by the above-mentioned formula (I) include the compounds set forth below.
(1) 2-methylthio-5-(1-hydroxy-6-methoxycarbonylhexyl)-4-(3-t-butyldimethylsilyloxy-1-octenyl)-2-cyclopentenone
(2) 2-methylthio-5-(1-hydroxy-6-methoxycarbonyl)-4-(3-hydroxy-1-octenyl)-2-cyclopentenone
(3) 2-methylsulfinyl-5-(1-hydroxy-6-methoxycarbonylhexyl)-4-(3-hydroxy-1-octenyl)-2-cyclopentenone
(4) 2-methylsulfonyl-5-(1-hydroxy-6-methoxycarbonylhexyl)-4-(3-hydroxy-1-octenyl)-2-cyclopentenone
(5) 2-methylthio-5-(1-hydroxy-6-carboxyhexyl)-4-(3-hydroxy-1-octenyl)-2-cyclopentenone
(6) 2-methylthio-5-(6-methoxycarbonylhexylidene)-4-(3-t-butyldimethylsilyloxy-1-octenyl)-2-cyclopentenone
(7) 2-methylthio-5-(6-methoxycarbonylhexylidene)-4-(3-hydroxy-1-octenyl)-2-cyclopentenone (8) 2-methylsulfinyl-5-(6-methoxycarbonylhexylidene)-4-(3-hydroxy-1-octenyl)-2-cyclopentenone
(9) 2-methylsulfonyl-5-(6-methoxycarbonylhexylidene)-4-(3-hydroxy-1-octenyl)-2-cyclopentenone
(10) 2-methylthio-5-(6-methoxycarbonylhexylidene)-4-(3-acetoxy-1-octenyl)-)-2-cyclopentenone
(11) 2-methylthio-5-(6-carboxyhexylidene)-4-(3-hydroxy-1-octenyl)-2-cyclopentenone
(12) 2-methylthio-5-(6-methoxycarbonylhexylidene)-4-(1-octenyl)-2-cyclopentenone
(13) 2-methylsulfinyl-5-(6-methoxycarbonylhexylidene)-4-(1-octenyl)-2-cyclopentenone
(14) 2-methylsulfonyl-5-(6-methoxycarbonylhexylidene)-4-(1-octenyl)-2-cyclopentenone
(15) 2-methylthio-5-(6-carboxyhexylidene)-4-(1-octenyl)-2-cyclopentenone
(16) 2-methylthio-5-(1-methylthio-6-methoxycarbonylhexylidene)-4-(1-octenyl)-2-cyclopentenone
(17) 2-methylsulfinyl-5-(1-methylsulfinyl-6-methoxycarbonylhexylidene)-4-(1-octenyl)-2-cyclopentenone
(18) 2-methylsulfonyl-5-(1-methylsulfonyl-6-methoxycarbonylhexylidene)-4-(1-octenyl)-2-cyclopentenone
(19) 2-ethylthio-5-(1-hydroxy-6-methoxycarbonynlhexyl)-4-(3-t-butyldimethylsililoxy-1-octenyl)-2-cyclopentenone
(20) 2-ethylthio-5-(6-methoxycarbonylhexylidene)-4-(3-t-butyldimethylsilyloxy-1-octenyl)-2-cyclopentenone
(21) 2-ethylthio-5-(6-methoxycarbonylhexylidene)-4-(3-hydroxy-1-octenyl)-2-cyclopentenone
(22) 2-ethylsulfinyl-5-(6-methoxycarbonylhexylidene)-4-(3-hydroxy-1-octenyl)-2-cyclopentenone
(23) 2-ethylsulfonyl-5-(6-methoxycarbonylhexylidene)-4-(3-hydroxy-1-octenyl)-2-cyclopentenone
(24) 2-ethylthio-5-(6-carboxylhexylidene)-4-(3-hydroxy-1-octenyl)-2-cyclopentenone
(25) 2-phenylthio-5-(8-ethoxycarbonyloctylidene)-4-[3-(tetrahydropyran-2-yloxy)-1-octenyl]-2-cyclopentenone
(26) 2-phenylthio-5-(8-ethoxycarbonyloctylidene)-4-(3-hydroxy-1-octenyl)-2-cyclopentenone
(27) 2-phenylsulfinyl-5-(8-ethoxycarbonyloctylidene)-4-(3-hydroxy-1-octenyl)-2-cyclopentenone
(28) 2-phenylsulfonyl-5-(8-ethoxycarbonyloctylidene)-4-(3-hydroxy-1-octenyl)-2-cyclopentenone
(29) 2-phenylthio-5-(8-carboxyoctylidene)-4-(3-hydroxy-1-octenyl)-2-cyclopentenone
(30) 2-(5-methoxycarbonylpentylthio)-5-(1-hydroxy-6-methoxycarbonyl-2-hexynyl)-4-(3-t-butyldimethylsilyloxy-3-cyclopentyl-1-propenyl)-2-cyclopentenone
(31) 2-(5-methoxycarbonylpentylthio)-5-(1-hydroxy-6-methoxycarbonyl-2-hexynyl)-4-(3-hydroxy-3-cyclopentyl-1-propenyl)-2-cyclopentenone
(32) 2-(5-methoxycarbonylpentylthio)-5-(6-methoxycarbonyl-2-hexynylidene)-4-(3-t-butyldimethylsilyloxy-3-cyclopentyl-1-propenyl)-2-cyclopentenone
(33) 2-(5-methoxycarbonylpentylthio)-5-(6-methoxycarbonyl-2-hexynylidene)-4-(3-hydroxy-3-cyclopentyl-1-propenyl)-2-cyclopentenone
(34) 2-(5-methoxycarbonylpentylsulfinyl)-5-(6-methoxycarbonyl-2-hexynylidene)-4-(3-hydroxy-3-cyclopentyl-1-propenyl)-2-cyclopentenone
(35) 2-(5-methoxycarbonylpentylsulfonyl)-5-(6-methoxycarbonyl-2-hexynylidene)-4-(3-hydroxy-3-cyclopentyl-1-propenyl)-2-cyclopentenone
(36) 2-(3-phenylpropylthio)-5-(1-hydroxy-6-methoxycarbonyl-2-hexynyl)-4-(3-t-butyldimethylsilyloxy-3-cyclopentyl-1-propenyl)-2-cyclopentenone
(37) 2-(3-phenylpropylthio)-5-(1-hydroxy-6-methoxycarbonyl-2-hexynyl)-4-(3-t-butyldimethylsilyloxy-3-cyclopentyl-1-propenyl)-2-cyclopentenone
(38) 2-(3-phenylpropylthio)-5-(6-methoxycarbonyl-2-hexynylidene)-4-(3-t-butyldimethylsilyloxy-3-cyclopentyl-1-propenyl)-2-cyclopentenone
(39) 2-(3-phenylpropylthio)-5-(6-methoxycarbonyl-2-hexynylidene)-4-(3-hydroxy-3-cyclopentyl-1-propenyl)-2-cyclopentenone
(40) 2-(3-phenylpropylsulfinyl)-5-(6-methoxycarbonyl-2-hexynylidene)-4-(3-hydroxy-3-cyclopentyl-1-propenyl)-2-cyclopentenone
(41) 2-(3-phenylpropylsulfonyl)-5-(6-methoxycarbonyl-2-hexynylidene)-4-(3-hydroxy-3-cyclopentyl-1-propenyl)-2-cyclopentenone
(42) 2-phenylthio-5-(1-hydroxy-6-methoxycarbonyl-2-hexynyl)-4-(3-hydroxy-3-cyclopentyl-1-propenyl)-2-cyclopentenone
(43) 2-phenylthio-5-(6-methoxycarbonyl-2-hexynylidene)-4-(3-hydroxy-3-cyclopentyl-1-propenyl)-2-cyclopentenone
(44) 2-phenylsulfinyl-5-(6-methoxycarbonyl-2-hexynylidene)-4-(3-hydroxy-3-cyclopentyl-1-propenyl)-2-cyclopentenone
(45) 2-phenylsulfonyl-5-(6-methoxycarbonyl-2-hexynylidene)-4-(3-hydroxy-3-cyclopentyl-1-propenyl)-2-cyclopentenone
(46) 2-(6-methoxylnaphthyl-2-thio)-5-(1-hydroxy-6-methoxycarbonyl-2-hexynyl)-4-(3-hydroxy-3-cyclopentyl-1-propenyl)-2-cyclopentenone
(47) 2-(6-methoxynaphthyl-2-thio)-5-(6-methoxycarbonyl-2-hexynylidene)-4-(3-hydroxy-3-cyclopentyl-1-propenyl)-2-cyclopentenone
(48) 2-(6-methoxynaphthyl-2-sulfinyl)-5-(6-methoxycarbonyl-2-hexynylidene)-4-(3-hydroxy-3-cyclopentyl-1-propenyl)-2cyclopentenone
(49) 2-(6-methoxynaphthyl-2-sulfonyl)-5-(6-methoxycarbonyl-2-hexynylidene)-4-(3-hydroxy-3-cyclopentyl-1-propenyl)-2-cyclopentenone
(50) 2-(4-chlorophenylmethylthio)-5-(1-hydroxy-6-methoxycarbonyl-5-hexenyl)-4-(3-hydroxy-5-methyl-1-nonenyl)-2-cyclopentenone.
(51) 2-(4-chlorophenylmethylthio)-5-(6-methoxycarbonyl-5-hexenylidene-4-(3-hydroxy-5-methyl-1-nonenyl)-2-cyclopentenone
(52) 2-(4-chlorophenylmethylsulfinyl)-5-(6-methoxycarbonyl-5-hexenylidene)-4-(3-hydroxy-5-methyl-1-nonenyl)-2-cyclopentenone
(53) 2-(4-chlorophenylmethylsulfonyl)-5-(6-methoxycarbonyl-5-hexenylidene)-4-(3-hydroxy-5-methyl-1-nonenyl)-2-cyclopentenone
(54) 2-ethylthio-5-(1-hydroxy-6-methoxy(carbonylhexyl)-4-[3-(tetrahydropyran-2-yloxy)-3-cyclohexyl-1-propenyl]-2-cyclopentenone
(55) 2-ethylthio-5-(6-methoxycarbonylhexylidene)-4-[3-(tetrahydropyran-2-yloxy)-3-cyclohexyl-1-propenyl]-2-cyclopentenone
(56) 2-ethylthio-5-(6-methoxycarbonylhexylidene)-4-(3-hydroxy-3-cyclohexyl-1-propenyl)-2-cyclopentenone
(57) 2-(4-methylphenylthio)-5-(1-hydroxy-3-phenyl-2-propenyl)-4-butyl-2-cyclopentenone
(58) 2-(4-methylphenylthio)-5-(3-phenyl-2-propenylidene)-4-butyl-2-cyclopentenone
(59) 2-(4-methylphenylsulfinyl)-5-(3-phenyl-2-propenylidene)-4-butyl-2-cyclopentenone

(60) 2-(4-methylphenylsulfonyl)-5-(3-phenyl-2-propenylidene)-4-butyl-2-cyclopentenone
(61) 2-methylthio-5-(1,4,7-trihydroxy-2-heptenyl)-4-(4-phenoxybutyl)-4-trimethylsilyloxy-2-cyclopentenone
(62) 2-methylthio-5-(1,4,7-trihydroxy-2-heptenyl)-4-(4-phenoxybutyl)-4-hydroxy-2-cyclopentenone
(63) 2-methylsulfinyl-5-(1,4,7-trihydroxy-2-heptenyl)-4-(4-phenoxybutyl)-4-hydroxy-2-cyclopentenone
(64) 2-methylsulfonyl-5-(1,4,7-trihydroxy-2-heptenyl)-4-(4-phenoxybutyl)-4-hydroxy-2-cyclopentenone
(65) 2-methylthio-5-(1-hydroxy-4,7-diacetoxy-2-heptenyl)-4-(4-phenoxybutyl)-4-hydroxy-2-cyclopentenone
(66) 2-methylthio-5-(4,7-dihydroxy-2-heptenylidene)-4-(4-phenoxybutyl)-4-trimethylsilyloxy-2-cyclopentenone
(67) 2-methylthio-5-(4,7-dihydroxy-2-heptenylidene)-4-(4-phenoxybutyl)-4-methoxy-2-cyclopentenone
(68) 2-methylthio-5-(4,7-dihydroxy-2-heptenylidene)-4-(4-phenoxybutyl)-4-ethoxy-2-cyclopentenone
(69) 2-methylthio-5-(4,7-diacetoxy-2-heptenylidene)-4-(4-phenoxybutyl)-4-hydroxy-2-cyclopentenone
(70) 2-methylthio-5-(4,7-diacetoxy-2-heptenylidene)-4-(4-phenoxybutyl)-4-acetoxy-2-cyclopentenone
(71) 2-methylsulfinyl-5-(4,7-dihydroxy-2-heptenylidene)-4-(4-phenoxybutyl)-4-hydroxy-2-cyclopetenone
(72) 2-methylsulfonyl-5-(4,7-dihydroxy-2-heptenylidene)-4-(4-phenoxybutyl)-4-hydroxy-2-cyclopentenone
(73) 2-methylthio-5-(4,7-dihydroxy-2-heptenylidene)-4-(4-phenoxybutylidene)-2-cyclopentenone
(74) 2-methylsulfinyl-5-(4,7-dihydroxy-2-heptenylidene)-4-(4-phenoxybutylidene)-2-cyclopentenone
(75) 2-methylsulfonyl-5-(4,7-dihydroxy-2-heptenylidene)-4-(4-phenoxybutylidene)-2-cyclopentenone
(76) 2-methylthio-5-[1-hydroxy-3-(4-methoxycarbonylcyclohexyl)propyl]-4-(4-phenoxybutyl)-4-hydroxy-2-cyclopentenone
(77) 2-methylthio-5-[3-(4-methoxycarbonylcyclohexyl)propylidene]-4-(4-phenoxybutyl)-4-hydroxy-2-cyclopentenone
(78) 2-methylsulfinyl-5-[3-(4-methoxycarbonylcyclohexyl)propylidene]-4-(4-phenoxybutyl)-4-hydroxy-2-cyclopentenone
(79) 2-methylsulfonyl-5-[3-(4-methoxycarbonylcyclohexyl)propylidene]-4-(4-phenoxybutyl)-4-hydroxy-2-cyclopentenone
(80) 2-methylthio-5-[1-hydroxy-4-(4-methoxyphenyl)butyl]-4-(4-phenoxybutyl)-4-hydroxy-2-cyclopentenone
(81) 2-ethylthio-5-[4-(4-methoxyphenyl)butylidene]-4-(4-phenoxybutyl)-4-hydroxy-2-cyclopentenone
(82) 2-methylsulfinyl-5-[4-(4-methoxyphenyl)butylidene]-4-(4-phenoxybutyl)-4-hydroxy-2-cyclopentenone
(83) 2-methylsulfonyl-5-[4-(4-methoxyphenyl)butylidene]-4-(4-phenoxybutyl)-4-hydroxy-2-cyclopentenone
(84) 2-phenylthio-5-(1-hydroxyoctyl)-4-(4-phenoxybutyl)-4-hydroxy-2-cyclopentenone
(85) 2-phenylthio-5-octylidene-4-(4-phenoxybutyl)-4-hydroxy-2-cyclopentenone
(86) 2-phenylsulfinyl-5-octylidene-4-(4-phenoxybutyl)-4-hydroxy-2-cyclopentenone
(87) 2-phenylsulfonyl-5-octylidene-4-(4-phenoxybutyl)-4-hydroxy-2-cyclopentenone
(88) 2-methylthio-5-(1-hydroxy-6-methoxycarbonylhexyl)-4-[3-(3,4-dimethoxyphenyl)propyl]-4-hydroxy-2-cyclopentenone
(89) 2-methylthio-5-(6-methoxycarbonylhexylidene)-4-[3-(3,4-dimethoxyphenyl)propyl]-4-hydroxy-2-cyclopentenone
(90) 2-methylsulfinyl-5-(6-methoxycarbonylhexylidene)-4-[3-(3,4-dimethoxyphenyl)propyl]-4-hydroxy-2-cyclopentenone
(91) 2-methylsulfonyl-5-(6-methoxycarbonylhexylidene)-4-[3-(3,4-dimethoxyphenyl)propyl]-4-hydroxy-2-cyclopentenone
(92) 2-methylthio-5-(1-hydroxy-6-methoxycarbonylhexyl)-4-(3,7-dimethyloctyl)-4-hydroxy-2-cyclopentenone
(93) 2-methylthio-5-(6-methoxycarbonylhexylidene)-4-(3,7-dimethyloctyl)-4-hydroxy-2-cyclopentenone
(94) 2-methylsulfinyl-5-(6-methoxycarbonylhexylidene)-4-(3,7-dimethyloctyl)-4-hydroxy-2-cyclopentenone
(95) 2-methylsulfonyl-5-(6-methoxycarbonylhexylidene)-4-(3,7-dimethyloctyl)-4-hydroxy-2-cyclopentenone
(96) 2-methylthio-5-(1-hydroxy-6-methoxycarbonylhexyl)-4-(1-hexynyl)-4-hydroxy-2-cyclopentenone
(97) 2-methylthio-5-(6-methoxycarbonylhexylidene)-4-(1-hexynyl)-4-hydroxy-2-cyclopentenone
(98) 2-methylsulfinyl-5-(6-methoxycarbonylhexylidene)-4-(1-hexynyl)-4-hydroxy-2-cyclopentenone
(99) 2-methylsulfonyl-5-(6-methoxycarbonylhexylidene)-4-(1-hexynyl)-4-hydroxy-2-cyclopentenone
(100) 2-methylthio-5-(1-hydroxy-6-methoxycarbonyl-2-hexynyl)-4-(3-hydroxy-3-cyclohexyl-1-propenyl)-4-hydroxy-2-cyclopentenone
(101) 2-methylthio-5-(6-methoxycarbonyl-2-hexynylidene)-4-(3-hydroxy-3-cyclohexyl-1-propenyl)-4-hydroxy-2-cyclopentenone
(102) 2-methylsulfinyl-5-(6-methoxycarbonyl-2-hexynylidene)-4-(3-hydroxy-3-cyclohexyl-1-propenyl)-4-hydroxy-2-cyclopentenone
(103) 2-methylsulfonyl-5-(6-methoxycarbonyl-2-hexynylidene)-4-(3-hydroxy-3-cyclohexyl-1-propenyl)-4-hydroxy-2-cyclopentenone
(104) 2-methylthio-5-(1-hydroxy-6-methoxycarbonylhexyl)-4-methyl-4-hydroxyl-2-cyclopentenone
(105) 2-methylthio-5-(6-methoxycarbonylhexylidene)-4-methyl-4-hydroxyl-2-cyclopentenone
(106) 2-methylsulfinyl-5-(6-methoxycarbonylhexylidene)-4-methyl-4-hydroxy-2-cyclopentenone
(107) 2-methylsulfonyl-5-(6-methoxycarbonylhexylidene)-4-methyl-4-hydroxy-2-cyclopentenone
(108) 2-methylthio-5-(1-hydroxy-6-methoxycarbonyl)-4-octyl-4-hydroxy-2-cyclopentenone
(109) 2-methylthio-5-(6-methoxycarbonylhexylidene)-4-octyl-4-hydroxy-2-cyclopentenone
(110) 2-methylsulfinyl-5-(6-methoxycarbonylhexylidene)-4-octyl-4-hydroxy-2-cyclopentenone
(111) 2-methylsulfonyl-5-(6-methoxycarbonylhexylidene)-4-octyl-4-hydroxy-2-cyclopentenone
(112) 2-methylthio-5-(6-carboxyhexylidene)-4-octyl-4-hydroxy-2-cyclopentenone
(113) 2-(2-phenylethylthio)-5-[1-hydroxy-5-(acetoxymethyl)-6-acetoxyhexyl]-4-(6-nonynyl)-4-hydroxy-2-cyclopentenone (114) 2-(2-phenylethylthio)-5-[5-(acetoxymethyl)-6-acetoxyhexylidene]-4-(6-nonynyl)-4-hydroxy-2-cyclopentenone (115) 2-(2-acetoxyethylthio)-5-(1-hydroxy-10-methoxydecyl)-4-benzyl-4-hydroxy-2-cyclopentenone (116) 2-(2-acetoxyethylthio)-5-(10-methoxydecylidene)-4-benzyl-4-hydroxy-2-cyclopentenone (117) 2-(3-acetylphenylmethylthio)-5-[1-hydroxy-4-(4-chlorophenoxy)butyl]-4-(1-octenyl)-4-hydroxy-2-cyclopentenone (118) 2-(3-acetylphenylmethylthio)-5-[4-(4-chlorophenoxy)butyl]-4-(1-octenyl)-4-hydroxy-2-cyclopentenone Of the 2-substituted-2-cyclopentenones of the above formula (I), 2-substituted-2-cyclopentenones represented by the following formula (I-b-11):

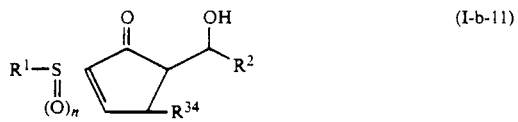

wherein $R^1$, $R^2$ and $R^{34}$ are as defined above, but preferably $R^2$ and $R^{34}$ are aliphatic hydrocarbon groups having 1 to 10 carbon atoms which also have as the substitutent —COOR$^5$ (where $R^5$ represents a hydrogen atom, an alkyl group having 1 to 10 carbon atoms or one equivalent cation); —OR$^6$ (where $R^6$ is a hydrogen atom; an acyl group having 2 to 7 carbon atoms; a tri(C$_1$-C$_7$)hydrocarbonsilyl group; a group which forms an acetal bond together with a oxygen atom to which $R^6$ is bonded; an aromatic hydrocarbon group which may be substituted with a halogen atom, a hydroxyl group, a tri(C$_1$-C$_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a hydroxyl group, a tri(C$_1$-C$_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms; or an alicyclic group which may be substituted with a halogen atom, an hydroxyl group, a tri(C$_1$-C$_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms and an alkoxy group having 1 to 4 carbon atoms; and n represents 0, 1 or 2; can be prepared by subjecting 2-cyclopentenones represented by the following formula (III-a):

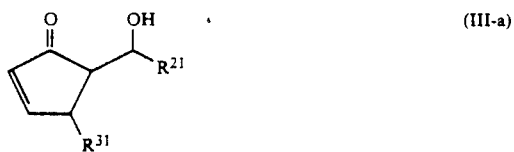

wherein $R^{21}$ and $R^{31}$ represent an aliphatic hydrocarbon group having 1 to 10 carbon atoms which may have as the substituent —COOR$^{51}$ (where $R^{51}$ is an alkyl group having 1 to 10 carbon atoms); —OR$^{61}$ (where $R^{61}$ is an acyl group having 2 to 7 carbon atoms; a tri(C$_1$-C$_7$)hydrocarbonsilyl group; a group which forms an acetal bond together with an oxygen atom to which $R^{61}$ is bonded; an aromatic hydrocarbon group also may be substituted with a halogen atom, a tri(C$_1$-C$_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a tri(C$_1$-C$_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms; or an alicyclic group which may be substituted with a halogen atom, a tri(C$_1$-C$_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms and an alkoxy group having 1 to 4 carbon atoms; to epoxydization reaction to obtain 2,3-epoxycyclopentanones of the following formula (IV-a-1):

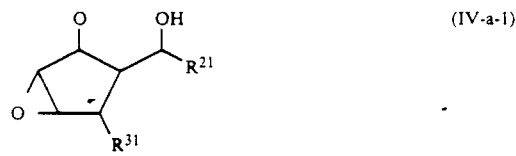

wherein $R^{21}$ and $R^{31}$ are as defined above, then reacting thiols represented by the following formula (V):

$$R^1—SH \qquad (V)$$

wherein $R^1$ represents a substituted or non-substituted hydrocarbon group having 1 to 10 carbon atoms with said 2,3-epoxycyclopentanones in the presence of a basic compound, a alumina or silica gel, and subsequently, subjecting the reaction product, if necessary, to oxidation reaction, deprotection reaction or protection reaction.

The starting material represented by the above formula (III-a) is known per se, and can be prepared by the method disclosed in Japanese Unexamined Patent Publication (Kokai) No. 59-164747.

In the above formula (III-a), $R^{21}$ and $R^{31}$ represent an aliphatic hydrocarbon group having 1 to 10 carbon atoms which may have as the substituent —COOR$^{51}$ (where $R^{51}$ is an alkyl group having 1 to 10 carbon atoms); —OR$^{61}$ (where $R^{61}$ represents an acyl group having 2 to 7 carbon atoms, a tri(C$_1$-C$_7$)hydrocarbonsilyl group; a group which forms an acetal bond together with the hydrogen atom to which $R^{61}$ is bonded; an aromatic hydrocarbon group which also may be substituted with a halogen atom, a tri(C$_1$-C$_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a tri(C$_1$-C$_7$)hydrocarbonsilyloxy group, an acyloxy group having 2 to 7 carbon atoms, an acyl group having 2 to 7 carbon atoms; an alkoxycarbonyl group having 2 to 5 carbon atoms, an alkyl group having 1 to 4 carbon atoms, and an alkoxy group having 1 to 4 carbon atoms; or an alicyclic group which may be substituted with a halogen atom, a tri($C_1$-$C_7$)hydrocarbonsilyloxy group, an acyloxy group having 2 to 7 carbon atoms, an acyl group having 2 to 7 carbon atoms an alkoxycarbonyl group having 2 to 5 carbon atoms, an alkyl group having 1 to 4 carbon atoms and an alkoxy group having 1 to 4 carbon atoms. As specific examples of $R^{21}$ and $R^{31}$, the same specific examples as described above for $R^2$ and $R^3$ in the above formula (I), respectively, can be included.

In the process of the present invention, the compounds of the above formula (III-a) are subjected to epoxydization reaction. As the reagent for the epoxydization reaction, an alkylhydroperoxide such as t-butylhydroperoxide or hydrogen peroxide may be used, but preferably hydrogen peroxide is used. Although anhydrous hydrogen peroxide may be used, a 90 to 5% aqueous hydrogen carbon, preferably 50 to 10% aqueous hydrogen peroxide is generally used. The amount of hydrogen peroxide used may be 1 to 50 equivalents, preferably 3 to 20 equivalents, relative to 2-cyclopentenones represented by the above formula (III-a).

Preferably the epoxydization reaction is carried out in the presence of a basic compound, and examples of such basic compounds include quaternary ammonium hydroxides such as tetramethyl ammonium hydroxide, and benzyltrimethyl ammonium hydroxide; hydroxides such as lithium hydroxide, sodium hydroxide, and potassium hydroxide; and carbonates such as sodium carbonate and potassium carbonate. Preferably, alkali metal hydroxides such as sodium hydroxide and potassium hydroxide; alkali metal carbonates such as sodium carbonates and potassium carbonate particularly preferably sodium hydroxide, are used. The amount of the basic compound used may be 0.01 to 5 equivalents, preferably 0.05 to 2 equivalents, relative to the 2-cyclopentenones represented by the above formula (III-a).

The reaction solvent may include alcohols such as methanol, ethanol, and t-butyl alcohol; ketones such as acetone and methyl ethyl ketone; ethers such as dioxane, and dimethoxyethane, which are inert to hydrogen peroxide, and can be mixed with water, preferably alcohols such as methanol, ethanol, and t-butyl alcohol, particularly preferably methanol or ethanol.

The reaction temperature of the epoxydization reaction is preferably within $-20°$ to $50°$ C., more preferably $-5°$ to $30°$ C.

The reaction time of the epoxydization reaction may differ depending on the starting compound, the reagent, the reaction solvent is and the reaction temperature employed, but preferably is within 5 minutes to 5 hours, more preferably 10 minutes to 1 hour.

After completion of the epoxydization reaction, the 2,3-epoxycyclopentanones represented by the above formula (IV-a-1) can be isolated and purified by a conventional means such as extraction, washing, drying, concentration, and chromatography, but the unpurified reaction mixture also can be provided as such for the subsequent reactions without isolation of said 2,3-epoxycyclopentanones.

The 2,3-epoxycyclopentanones represented by the above formula (IV-a-1) obtained in the above epoxydization reaction are novel compounds. The reaction between the compounds of the above for (IV-a-1) and the thiols represented by the above formula (V) is carried out in the presence of a basic compound, alumina or silica gel.

In the above formula (V), $R^1$ represents a substituted or non-substituted hydrocarbon having 1 to 10 carbon atoms. Specific examples of $R^1$ include those which are the same as the specific examples described for the above formula (I).

When a basic compound is used in carrying out the reaction between the 2,3-epoxycyclopentenones of the above formula (IV-a-1) and the thiols of the formula (V), such basic compounds are preferably alkali metal hydroxides or carbonates such as sodium hydroxide, potassium hydroxide, potassium carbonate, and sodium carbonate; or tertiary amines such as trimethylamine, triethylamine, and pyridine; bicyclo strong bases such as diazabicyclo[2.2.2]octane and diazabicyclo[3.4.0]-nonen; and quaternary ammonium salts such as benzyl trimethyl ammonium hydroxide.

Particularly preferably, the above tertiary amines such as triethylamine are used.

To allow a better reaction, preferably an inert solvent is used. As the solvent to be used, any inert solvent which can dissolve the starting compound may be used, but preferably alcohols such as methanol and ethanol; ethers such as ethyl ether and tetrahydrofuran; and hydrocarbons such as hexane and benzene, are used.

The amount of the solvent used should permit the reaction to proceed smoothly, and is preferably 1 to 100-fold volume of the starting material, more preferably 2 to 20-fold volume.

The amount of the thiols (V) to be used in the present invention is preferably stoichiometrically equimolar to the starting material (IV-a-1). The basic compound which catalyzes the reaction is preferably used in an amount of 0.001 to 20-fold mol, more preferably 0.1 to 2-fold mol, relative to the starting material (IV-a-1).

Preferably, the reaction temperature is within $-20°$ to $100°$ C., more preferably $0°$ to $30°$ C., and preferably the reaction time for completion of the reaction is 20 minutes to 2 hours.

After the reaction, the 2-substituted-2-cyclopentenones represented by the following formula (I-b-10):

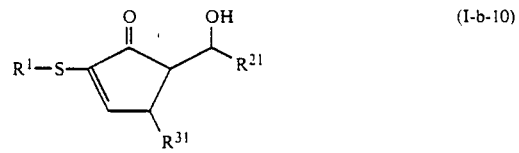

(I-b-10)

wherein $R^1$, $R^{21}$ and $R^{31}$ are as defined above can be isolated and purified by treating the reaction mixture by a customary procedure. For example, isolation and purification can be performed by extraction, washing, concentration, and chromatography, or combinations thereof, but the unpurified reaction mixture can be subjected as such to oxidation reaction, deprotection reaction and/or protection reaction without isolation of said 2-substituted-2-cyclopentenones, to produce the compounds of the above formula (I-b-11).

Preferably, such an oxidation reaction is carried out in an inert solvent in the presence of an oxidizing agent.

Examples of the oxidizing agent used when producing sulfoxide preferably include peracids such as hydrogen peroxide, peracetic acid, perbenzoic acid, and m-chloroperbenzoic acid; and sodium metaperiodate, selenium dioxide, chromic acid, iodosylbenzene, hypochlorous acid, and t-butyl hydroperoxide; and when producing sulfone, preferably include hydrogen peroxide, hydrogen peroxide and a tungsten oxide or vanadium oxide catalyst, peracetic acid, perbenzoic acid, m-chloroperbenzoic acid, ruthenium oxide, and osmium tetraoxide.

As the inert organic solvent, for example, preferably acetic acid, methylene chloride, chloroform, 1,2-dicycloroethane, benzene, and ethyl acetate are used.

Preferably the reaction temperature is within $-78°$ C. to 50° C., more preferably $-20°$ C. to 30° C.

The reaction time may differ depending on the starting compound, the reaction temperature, and the kind of oxidizing agent, but preferably is 30 minutes to 38 hours.

For example, when a sulfoxide is to be produced by using an oxidizing agent which can produce both sulfoxide and sulfone, preferably the amount of the oxidizing agent is not enough to produce sulfone, for example, an amount of about 1 to about 1.5 equivalents relative to the (I-b-10) used, and the reaction is monitored by thin layer chromatography (i.e., TLC).

After completion of the reaction, the desired compound can be isolated and purified by conventional methods such as extraction, washing, concentration, and chromatography.

Further, a desired compound having protective groups in the molecular can be subjected to deprotection reaction.

Elimination of the protective group, when the protective group is a group forming an acetal bond together with oxygen atom of hydroxyl group, is preferably carried out by using acetic acid, and a pyridinium salt of p-toluenesulfonic acid or cation ion exchange resin as the catalyst, and by using a reaction solvent such as water, tetrahydrofuran, ethyl ether, dioxane, acetone, and acetonitrile. Preferably the reaction is carried out at a temperature of from $-78°$ C. to $+30°$ C., for about 10 minutes to 3 days. When the protective group is a tri($C_1$–$C_7$)hydrocarbonsilyl group, the reaction may be practiced in the reaction solvent as mentioned above in the presence of, for example, acetic acid, hydrogen fluoride-pyridine, tetrabutylammonium fluoride, and cesium fluoride at the same temperature and for the same time. When the protective group is an acyl group, the reaction may be practiced by carrying out hydrolysis in, for example, an aqueous solution of sodium hydroxide, potassium hydroxyde, and calcium hydroxide, or a water-alcohol mixture or a methanol or ethanol solution containing sodium methoxide, potassium methoxide, and sodium ethoxide.

An ester group in the required compound can be subjected to hydrolysis, which can be carried out by using an enzyme such as lipase in water or a solvent containing water at a temperature of from $-10°$ C. to $+60°$ C., for about 10 minutes to 24 hours.

When the desired compound has a carboxyl group in the molecule, the compound can be further subjected to a salt forming reaction, to obtain a corresponding carboxylic acid salt. The salt forming reaction is known per se, and may be practiced by carrying out the neutralization reaction with a basic compound such as sodium hydroxide, potassium hydroxyde, sodium carbonate, or ammonia, trimethylamine, monoethanolamine, and morpholine, by a customary procedure, in an amount substantially equal to the carboxylic acid.

Further, a desired compound having a hydroxyl group in the molecule can be subjected to protection reaction.

Known methods can be employed for the protection reaction of the hydroxyl group. For example, when the protective group is an acyl group such as an acetyl group, propionyl group, or benzoyl group, the protective group can be easily introduced by reacting an acid halide or an acid anhydride with pyridine. When the protective group is a trihydrocarbonsilyl group such as a trimethylsilyl group or t-butyldimethylsilyl group, the protective group can be introduced by reacting a trihydrocarbonsilyl halide in the pressure of amines such as triethylamine and dimethylaminopyridine. When the protective group is a tetrahydropyran-2-yl group tetrahydrofuran-2-yl group, or 1-ethoxyethyl group, the protective group can be introduced by placing the compound in contact with dihydropyrane, dihydrofuran, or ethyl vinyl ether, which is a corresponding vinyl other compound, in the presence of an acidic catalyst such as p-toluenesulfonic acid, and thus novel 2-substituted-2-cyclopentenones represented by the above formula (I-b-11) are prepared.

When alumina or silica gel is used during the reaction between the 2,3-epoxycyclopentenones of the above formula (IV-a-1) and the thiols of the formula (V), such alumina or silica gel may be silica gel or alumina used generally during a separation and purification of an organic compound. For the silica gel, for example, Wakol Gel C-300, Wakol Gel C-200 may be employed. Similarly, for the alumina, for example, preferably basic alumina (basic alumina produced by Woelm Co.), acidic alumina (neutral alumina produced by Woelm Co.), and active alumina are used, more preferably, basic alumina.

To allow a better reaction, preferably an inert solvent is used. As the solvent, any inert solvent which can dissolve the starting compound may be used, but preferably alcohols such as methanol and ethanol, ethers such as ethyl ether and tetrahydrofuran, and hydrocarbons such as hexane and benzene are employed.

The amount of the solvent should permit the reaction to proceed smoothly, but preferably 1 to 100-fold volumes of the starting material, more preferably 2 to 20-fold volumes are employed.

The amount of the thiols (V) to be used in the present invention is preferably stoichiometrically equimolar to the starting material (IV-a-1). The silica gel and alumina which catalyse the reaction is preferably used in an amount of 0.1 to 20-fold weight, more preferably 0.5 to 5-fold weight, relative to the starting material (IV-a-1).

Preferably, the reaction temperature is within $-20°$ to 100° C., more preferably 0° to 30° C. The reaction time may differ depending on the catalyst amount and the solvent used, but preferably the reaction is completed within 10 minutes to 24 hours.

After the reaction, the 2-substituted-2-cyclopentenones represented by the above formula (I-b-10) can be obtained only by filtering the reaction mixture to remove alumina and silica gel, and evaporating the reaction solvent, but for a further purification, they also can be obtained by the methods of, for example, recrystallization and chromatography, or a combination thereof.

Of the 2-substituted-2-cyclopentenones of the above formula (I) of the present invention, the 2-substituted-2-cyclopentenones according to claim 1 represented by the following formula (I-a-1).

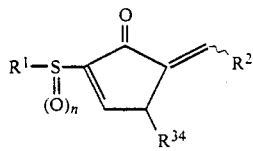

(I-a-1)

wherein $R^1$, $R^2$, $R^{34}$ and n are as defined above; the representation denotes that the substituent bonded to the double bond is in an E-configuration or a Z-configuration or mixtures thereof at any desired ratio; can be produced according to the present invention by dehydrating the 2-substituted-2-cyclopentenones represented by the following formula (I-b-10):

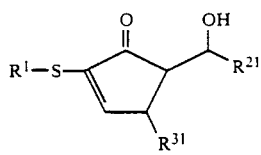

(I-b-10)

wherein $R^1$, $R^{21}$ and $R^{31}$ are as defined above, and subjecting the dehydrated product to oxidation, deprotection reaction and/or protection reaction.

In the above formula (I-b-10), $R^1$ represents a substituted or non-substituted hydrocarbon group having 1 to 10 carbon atoms. Specific examples of $R^1$ include the same specific examples as described above for the formula (I).

In the above formula (I-b-10), $R^{21}$ and $R^{31}$ represent an aliphatic hydrocarbon group having 1 to 10 carbon atoms which may have as the substituent $-COOR^{51}$ (where $R^{51}$ is an alkyl group having 1 to 10 carbon atoms) or $-OR^{61}$ (where $R^{61}$ is an acyl group having 2 to 7 carbon atoms; a tri($C_1$-$C_7$)hydrocarbonsilyl group, a group which forms an acetal bond together with the oxygen atom to which $R^{61}$ is bonded; an aromatic hydrocarbon group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms; or an alicyclic group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms and an alkoxy group having 1 to 4 carbon atoms. In the above formula (I-b-10), specific examples of $R^{21}$ and $R^{31}$ include the same specific examples as described for $R^2$ and $R^3$ in the above formula (I).

In the process of the present invention, the compounds of the above formula (I-b-10) are subjected to dehydration reaction. Dehydration reaction is preferably carried out by using a basic compound and a reactive derivative of an organic sulfuric acid. More specifically, the compound of the above formula (I-b-10) is preferably first treated with a basic compound and a reactive derivative of an organic sulfonic acid, and further treated with a basic compound. The dehydration reaction is completed by a sulfonylation of the hydroxyl group of the compound of the formula (I-b-11), and then elimination of an organic sulfonic acid.

Preferably, amines are used as the basic compound together with the derivative of an organic sulfonic acid, and examples of such amines include pyridine, 4-dimethylaminopyridine, triethylamine, diisopropylcyclohexylamine, 1,5-diazabicyclo[4.3.0]non-5-ene (hereinafter abbreviated as DBN), 1,8-diazabicyclo[5.4.0]undec-7-ene (hereinafter abbreviated as DBU), quinacridine, triethylenediamine, isopropyldimethylamine, and diisopropylethylamine. Particularly, preferably are pyridine, 4-dimethylaminopyridine, DBU, and DBN.

Examples of reactive derivatives of organic sulfonic acid include organic sulfonic acid halides such as methanesulfonylchloride, ethanesulfonylchloride, n-butanesulfonylchloride, t-butanesulfonylchloride, trifluoromethanesulfonylchloride, benzenesulfonylchloride, and p-toluenesulfonylchloride; and anhydrous organic sulfonic acids such as anhydrous methanesulfonic acid, anhydrous ethanesulfonic acid, anhydrous trifluoromethanesulfonic acid, anhydrous benzenesulfonic acid, and anhydrous p-toluenesulfonic acid.

The basic compound itself as mentioned above may be also used as the solvent, but preferably halogenated hydrocarbons such as dichloromethane, chloroform, carbon tetrachloride, and dichloroethane; ethers such as ether and tetrahydrofuran; and hydrocarbons such as benzene, toluene, pentane, hexane, and cyclohexane are used. Most preferably, pyridine and dichloromethane is used.

Preferably, the derivative of an organic sulfonic acid is used at a ratio of 1 to 10 equivalents relative to 1 mol of the compound of the above formula (I-b-10).

Preferably, the basic compound is used at a ratio of 1 equivalent or more, most preferably 2 or more equivalents, relative to the reactive derivatives of the organic sulfonic acid employed.

Preferably, the amount of the solvent used is 1 to 1000-fold volume, more preferably 5 to 100-fold volume, relative to the compound represented by the above formula (I-b-10). The reaction temperature may differ depending on the starting compound, the basic compound, and the solvent, etc. employed, but preferably is from $-40°$ C. to $100°$ C., more preferably from $0°$ C to $30°$ C. The reaction time depends on the conditions, but preferably is about 0.1 to 10 hours. The progress of the reaction is monitored by a method such as thin layer chromatography.

Therefore, according to the above reaction (hereinafter referred to as the first reaction), an organic sulfonyloxyoxy derivative is formed in which the hydroxyl group on the alkyl group at the 5-position of the 2-substituted-2-cyclopentenones of the above formula (I-b-10) is converted to an organic sulfonyloxy group, and the compound is subsequently treated with a basic compound (hereinafter referred to as the second reaction) to eliminate a corresponding organic sulfonic acid, thereby giving 2-substituted-2-cyclopentenones represented by the following formula (I-a-10):

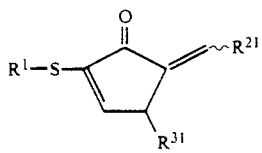

(I-a-10)

wherein $R^1$, $R^{21}$, $R^{31}$ and the representation $\sim$ are as defined above.

As the basic compound which can be used in the second reaction, the same basic compounds as mentioned in the above first reaction may be included, or the basic compound used in the second reaction may be different from that used in the first reaction.

The second reaction can be permitted to proceed within the same temperature range. Also, the organic sulfonyloxy derivative may be isolated and then subjected to the second reaction, or the first reaction and the second reaction may be carried out in the same reaction system. After completion of the reaction, the desired compound can be isolated and purified by conventional means such as extraction, washing, concentration, chromatography or combinations thereof, but if necessary, the unpurified reaction mixture can be subjected as such to oxidation, deprotection reaction and/or protection reaction without isolation of said 2-substituted-2-cyclopentenones, whereby 2-substituted-2-cyclopentenones of the above formula (I-a-1) can be prepared. Such oxidation reaction, deprotection reaction or protection reaction can be accomplished by the same methods as used for producing the 2-substituted-2-cyclopentenones represented by the above formula (I-b-11) from the 2-substituted-2-cyclopentenones represented by the above formula (I-b-10).

Of the 2-substituted-2-cyclopentenones of the above formula (I) of the present invention, the 2-substituted-2-cyclopentenones represented by the above formula (I-a-1) and the 2-substituted-2-cyclopentenones represented by the following formula (I-b-12):

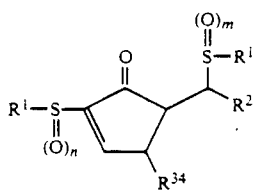

(I-b-12)

wherein $R^1$, $R^2$, $R^{34}$ and n are as defined above and m is 0, 1 or 2 can be produced according to the present invention by allowing 2,3-epoxycyclopentanones represented by the following formula (IV-a-2):

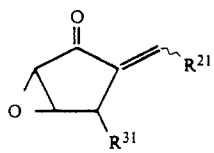

(IV-a-2)

wherein $R^{21}$, $R^{31}$ and the representation $\sim$ are as defined above to react with thiols represented by the following formula (V):

                          (V)

wherein $R^1$ is the same as defined above in the presence of a basic compound, alumina or silica gel, and then carrying out an oxidation reaction, deprotection reaction and/or protection reaction, if desired.

The starting material represented by the above formula (IV-a-2) is a material known per se, and can be prepared by, for example, the method described in Japanese Unexamined Patent Publication (Kokai) No. 61-47437.

In the above formula (IV-a-2), $R^{21}$ and $R^{31}$ represent an aliphatic hydrocarbon group having 1 to 10 carbon atoms which may have as the substituent —$COOR^{51}$ (where $R^{51}$ is an alkyl group having 1 to 10 carbon atoms); —$OR^{61}$ (where $R^{61}$ is an acyl group having 2 to 7 carbon atoms; a tri($C_1$-$C_7$)hydrocarbonsilyl group; a group which forms an acetal bond together with the oxygen atom to which $R^{61}$ is bonded; an aromatic hydrocarbon group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms; or an alicyclic group which may be substituted with a halogen atom, a tri($C_1$-$C_7$)hydrocarbonsilyloxy group, an acyloxy group having 2 to 7 carbon atoms, a acyl group having 2 to 7 carbon atoms, an alkoxycarbonyl group having 2 to 5 carbon atoms, an alkyl group having 1 to 4 carbon atoms and an alkoxy group having 1 to 4 carbon atoms. In the above formula (IV-a-2), specific examples of $R^{21}$ and $R^{31}$ include the same specific examples as mentioned above for $R^2$ and $R^3$ in the above formula (I).

In the above formula (V), $R^1$ represents a substituted or non-substituted hydrocarbon group having 1 to 10 carbon atoms, specific examples of $R^1$ may include the same specific examples as mentioned above for the above formula (I).

In the process of the present invention, the reaction is carried out between the 2,3-epoxycyclopentanones represented by the above formula (IV-a-2) and the thiols represented by the above formula (V) in the presence of a basic compound, alumina or silica gel, and then the reaction product is subjected to oxidation reaction, deprotection reaction and/or protection reaction, if desired, whereby the 2-substituted-2-cyclopentenones represented by the above formula (I-a-1) and (I-b-12) can be obtained. Such production processes can be accomplished by the same processes for producing 2-substituted-2-cyclopentenones represented by the above formula (I-b-11) from the 2,3-epoxycyclopentenones represented by the above formula (IV-a-1) and the thiols represented by the above formula (V).

Of the 2-substituted-2-cyclopentenones of the above formula (I) of the present invention, the 2-substituted-2-cyclopentenones represented by the following formula (I-b-2):

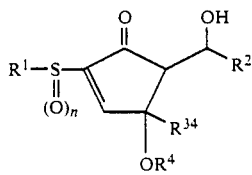 (I-b-2)

wherein $R^1$, $R^2$, $R^{34}$ and n are as defined above; and $R^4$ represents a hydrogen atom or a protected group of the protected hydroxyl group; can be prepared according to the present invention by subjecting the 2-substituted-2-cyclopentenones represented by the following formula (III-b):

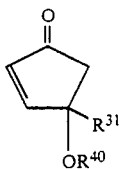 (III-b)

wherein $R^{31}$ represents an aliphatic hydrocarbon group having 1 to 10 carbon atoms which may be as the substituent —COOR$^{51}$ (where $R^{51}$ is an alkyl group having 1 to 10 carbon atoms); —OR$^{61}$ (where $R^{61}$ is an acyl group having 2 to 7 carbon atoms; a tri($C_1$-$C_7$)hydrocarbonsilyl group; a group which forms an acetal bond together with the oxygen atom to which $R^{61}$ is bonded; an aromatic hydrocarbon group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms; or an alicyclic group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms and an alkoxy group having 1 to 4 carbon atoms; and $R^{40}$ represents a hydrogen atom or a protected group of the protected hydroxyl group to epoxydization reaction to obtain the 2,3-epoxycyclopentanones represented by the following formula (IV-b-1):

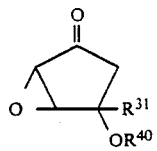 (IV-b-1)

wherein $R^{31}$ and $R^{40}$ are the same as defined above, which can be subjected to deprotection of $R^{31}$, if desired, to result in $R^{34}$, then reacting the 2,3-epoxycyclopentanones with the thiols represented by the following formula (V):

$$R^1—SH \qquad (V)$$

wherein $R^1$ is as defined above, further protecting the hydroxyl group, if desired, to obtain the 2-substituted-2-cyclopentenones represented by the following formula (I-c-1):

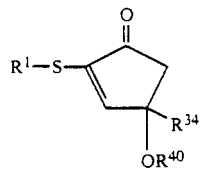 (I-c-1)

wherein $R^1$, $R^{34}$, and $R^{40}$ are the same as defined above; and for the further reaction, coverting $R^{34}$ to $R^{31}$ and $R^{40}$ to $R^{41}$ which represents a protective group of the protected hydroxyl group, subjecting this to aldol condensation reaction with aldehydes represented by the following formula (II):

$$OHC—R^{21} \qquad (II)$$

wherein $R^{21}$ is as defined above, and subsequently subjecting the reaction product to oxidation reaction, deprotection reaction and/or protection reaction, if desired.

The starting material represented by the above formula (III-b) is a material known per se, and may be prepared by the method described in Japanese Unexamined Patent Publication (Kokai) No. 62-96438. In the above formula (III-b), $R^{31}$ represents an aliphatic hydrocarbon group having 1 to 10 carbon atoms which may have as the substituent —COOR$^{51}$ (where $R^{51}$ is an alkyl group having 1 to 10 carbon atoms); —OR$^{61}$ (where $R^{61}$ is an acyl group having 2 to 7 carbon atoms; a tri($C_1$-$C_7$)hydrocarbonsilyl group; a group which forms an acetal bond together with the oxygen atom to which $R^{61}$ is bonded; an aromatic hydrocarbon group which may be substituted with a halogen atom, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms; or an alicyclic group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms and an alkoxy group having 1 to 4 carbon atoms. Specific examples of $R^{31}$ include the same specific examples as mentioned above for $R^3$ in the above formula (I). In the above formula (III-b), $R^{40}$ represents a hydrogen atom or a protected group of the protected hydroxyl group. Specific examples of $R^{40}$ include a hydrogen atom; alkyl groups such as methyl, ethyl, propyl, and isopropyl; tri($C_1$-$C_7$)hydrocarbonsilyloxy groups such as trimethylsilyl, triethylsilyl, t-butyldimethylsilyl, t-butyldiphenylsilyl, and tribenzylsilyl; groups which form an acetal bond together with the oxygen atom to which $R^{40}$ is bonded such as methoxymethyl, 1-ethoxyethyl, 2-methoxyethoxymethyl, and tetrahydropyran-2-yl; and acyl groups such as acetyl, propionyl, and butyryl.

In the process of the present invention, the compound of the above formula (III-b) is subjected to epoxydization reaction to obtain the 2,3-epoxycyclopentanones of the above formula (IV-b-1). The epoxydization reaction method can be the same method used for preparation of the 2,3-epoxycyclopentanones represented by the above formula (IV-a-1) by subjecting the 2-cyclopentenones represented by the above formula (III-a) to epoxydization reaction.

The 2,3-epoxycyclopentanones represented by the above formula (IV-b-1) obtained in the above epoxydization reaction are novel compounds. The reaction between the compounds of the above formula (IV-b-1) and the thiols represented by the above formula (V) is carried out in the presence of a basic compound, alumina or silica gel.

In the above formula (V), $R^1$ represents a substituted or non-substituted hydrocarbon group having 1 to 10 carbon atoms. Specific examples of $R^1$ include the same specific examples as mentioned above for the above formula (I).

In the process of the present invention, the reaction is carried out between the 2,3-epoxycyclopentanones represented by the above formula (IV-b-1) and the thiols represented by the above formula (V) in the presence of a basic compound, alumina or silica gel, and then the reaction product is subjected to protection reaction to obtain the 2-substituted-2-cyclopentenones represented by the above formula (I-c-1), if desired. This production process can be accomplished by the same process used for producing the 2-substituted-2-cyclopentenones represented by the above formula (I-b-10) from the 2,3-epoxycyclopentanones represented by the above formula (IV-a-1) and the thiols represented by the above formula (V).

The 2-substituted-2-cyclopentenones represented by the above formula (I-c-1) obtained in the above reaction are novel compounds. In the above formula (I-c-1), $R^{41}$ represents a protected group of the protected hydroxyl group. Specific examples of $R^{41}$ include alkyl groups such as methyl, ethyl, propyl, and isopropyl; tri($C_1$-$C_7$-)hydrocarbonsilyloxy groups such as trimethylsilyl, triethylsilyl, t-butyldimethylsilyl, t-butyldiphenylsilyl, and tribenzylsilyl; groups which form an acetal bond together with the oxygen atom to which $R^{41}$ is bonded such as methoxymethyl, 1-ethoxyethyl, 2-methoxyethoxymethyl, and tetrahydropyran-2-yl; and acyl groups such as acetyl, propionyl, and butyryl.

In the process of the present invention, the compounds represented by the above formula (I-c-1) and the aldehydes represented by the above formula (II) are subjected to aldol condensation reaction.

In the above formula (II), $R^{21}$ represents an aliphatic hydrocarbon group having 1 to 10 carbon atoms which may have as the substituent —$COOR^{51}$ (where $R^{51}$ is an alkyl group having 1 to 10 carbon atoms); —$OR^{61}$ (where $R^{61}$ is an acyl group having 2 to 7 carbon atoms; a tri($C_1$-$C_7$)hydrocarbonsilyl group; a group which forms an acetal bond together with the oxygen atom to which $R^{61}$ is bonded; an aromatic hydrocarbon group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms; or an alicyclic group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 2 to 5 carbon atoms, an alkyl group having 1 to 4 carbon atoms and an alkoxy group having 1 to 4 carbon atoms. Specific examples of $R^{21}$ include the same specific examples as mentioned above for $R^2$ in the above formula (I).

In the process of the present invention, the compounds represented by the above formula (I-c-1) and the aldehydes represented by the above formula (II) are subjected to aldol condensation reaction.

The aldol condensation reaction is carried out in the presence of a basic compound in a solvent. Examples of the basic compound and the reaction solvent include those described in: A. T. Nielsen, W. J. Haulihan, Organic Reaction (Org. React.), 16, 1 (1968); H. O. House, "Modern Synthetic Reactions" 2nd Ed., Benjamin (1972), p. 629; and New Experimental Chemistry Course 14, II736, III851, etc.

For the aldol condensation reaction, preferably metal amides such as lithium diisopropylamide, lithium diethylamide, and lithium bistrimethylsilylamide; or dialkylborontrifluoromethanesulfonic acids such as dibutylborontrifluoromethanesulfonic acid in the presence of a tertiary amine such as triethylamine, diisopropylethylamine, and tributylamine, are employed.

When the aldol condensation reaction is carried out by using a metal amide, preferably the amount thereof is 0.2 to 50 equivalents, more preferably 0.9 to 10 equivalents, relative to the compound of the above formula (I-c-1). As the reaction solvent, for example, ethers such as ether and tetrahydrofuran; and hydrocarbons such as petroleum ether, hexane, and pentane, may be employed. Preferably the reaction temperature is from $-150°$ C. to $100°$ C., more preferably from $-80°$ C. to $0°$ C.

When the aldol condensation reaction is carried out by using a tertiary amine and a dialkylboryl trifluoromethanesulfonate, preferably the amounts used thereof are, for example, 0.5 to 50 equivalents, more preferably 1 to 10 equivalents, relative to the compound of the above formula (I-c-1).

The aldehyde of the formula (II), which is the other starting material, preferably is used at a ratio of 0.5 to 10 equivalents, more preferably 0.8 to 2 equivalents, relative to the compound of the formula (I-c-1).

The reaction time depends on the starting compound, the reagents, and the reaction solvent employed, but preferably is from 5 minutes to 48 hours, more preferably from 10 minutes to 12 hours.

After completion of the reaction, the 2-substituted-2-cyclopentenones represented by the following formula (I-b-20):

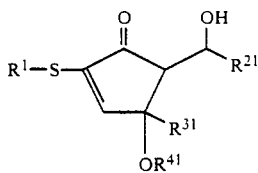

(I-b-20)

wherein $R^1$, $R^{21}$, $R^{31}$ and $R^{41}$ are as defined above can be obtained by isolating and purifying the reaction mixture by a conventional means such as extraction, water washing, drying, and chromatography, but the unpurified reaction mixture can be subjected to an oxidation reaction, deprotection reaction or protection reaction without isolation of said 2-substituted-2-cyclopentenones, whereby the compound of the above formula (I-b-2) can be prepared. Such an oxidation reaction, deprotection reaction or protection reaction can be carried out by the same methods as used in the preparation of the 2-substituted-2-cyclopentenones represented by the above formula (I-b-11) from the 2-substituted-2-cyclopentenones represented by the above formula (I-b-10).

Of the 2-substituted-2-cyclopentenones of the above formula (I) of the present invention, the 2-substituted-2-cyclopentenones represented by the following formula (I-a-2):

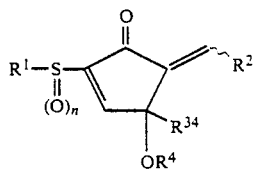

(I-a-2)

wherein $R^1$, $R^2$ $R^{34}$, $R^4$, n and the representation $\sim$ are as defined above can be prepared by dehydrating the 2-substituted-2-cyclopentenones represented by the following formula (I-b-20):

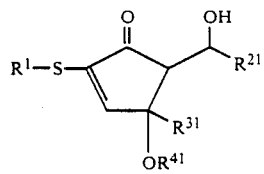

(I-b-20)

wherein $R^1$, $R^{21}$ $R^{31}$ and $R^{41}$ are as defined above, and subsequently subjecting the dehydrated product to an oxidation reaction, deprotection reaction and/or protection reaction, if desired.

In the above formula (I-b-20), $R^1$ represents a substituted or non-substituted hydrocarbon group having 1 to 10 carbon atoms, and specific examples of $R^1$ include the same specific examples as mentioned above for the above formula (I).

In the above formula (I-b-20), $R^{21}$ and $R^{31}$ represent an aliphatic hydrocarbon group having 1 to 10 carbon atoms which may have as the substituent $—COOR^{51}$ (where $R^{51}$ is an alkyl group having 1 to 10 carbon atoms) or $—OR^{61}$ (where $R^{61}$ is an acyl group having 2 to 7 carbon atoms; a tri($C_1$-$C_7$)hydrocarbonsilyl group; a group which forms an acetal bond together with the oxygen atom to which $R^{61}$ is bonded; an aromatic hydrocarbon group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms; or an alicyclic group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, or an alkoxy group having 1 to 4 carbon atoms. Specific examples of $R^{21}$ and $R^{31}$ in the above formula (I-b-20) include the same specific examples as mentioned above for $R^2$ and $R^3$, respectively for the above formula (I).

In the above formula (I-b-20), $R^{41}$ represents a protected group of the protected hydroxyl group. Specific examples of $R^{41}$ include alkyl groups such as methyl, ethyl, propyl, and isopropyl; tri($C_1$-$C_7$)hydrocarbonsilyl groups such as trimethylsilyl, triethylsilyl, t-butyldimethylsilyl, t-butyldiphenylsilyl, and tribenzylsilyl; groups which form an acetal bond together with the oxygen atom to which $R^{41}$ is bonded such as methoxymethyl, 1-ethoxyethyl, 2-methoxyethoxymethyl, and tetrahydropyran-2-yl; and acyl groups such as acetyl, propionyl, and butyryl.

In the process of the present invention, the compound of the above formula (I-b-20) is subjected to dehydration reaction. This dehydration reaction can be carried out by the same method as used in the preparation of the 2-substituted-2-cyclopentenones represented by the above formula (I-b-10) from the 2-substituted-2-cyclopentenones represented by the above formula (I-b-10), whereby 2-substituted-2-cyclopentenones represented by the following formula (I-a-20):

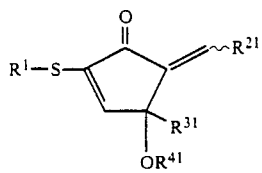

(I-a-20)

wherein $R^1$, $R^{21}$, $R^{31}$ $R^{41}$ and the representation $\sim$ are as defined above can be obtained.

The compound of the above formula (I-a-20) can be further subjected to oxidation reaction, deprotection reaction or protection reaction, if desired, to be converted to 2-substituted-2-cyclopentenones of the above formula (I-a-2). This oxidation reaction, deprotection reaction and/or protection reaction can be carried out by the same method as used in the preparation of the 2-substituted-2-cyclopentenones represented by the above formula (I-b-11) from the 2-substituted-2-cyclopentenones represented by the above formula (I-b-10).

Of the 2-substituted-2-cyclopentenones of the above formula (I) of the present invention, the 2-substituted-2-cyclopentenones represented by the following formula (I-a-3'), which are most preferably among the above formula (I-a-3):

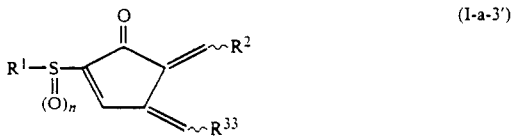

wherein $R^1$, $R^2$, n and the representation $\sim$ are as defined above; and $R^{33}$ represents a hydrogen atom or an aliphatic hydrocarbon group having 1 to 9 carbon atoms having as the substituent —COOR$^5$ (where $R^5$ represents hydrogen atom, an alkyl group having 1 to 10 carbon atoms or one equivalent cation); —OR$^6$ (where $R^6$ is an acyl group having 2 to 7 carbon atoms; a tri($C_1$-$C_7$)hydrocarbonsilyl group; a group which forms an acetal bond together with the oxygen atom to which $R^6$ is bonded; an aromatic hydrocarbon group which may be substituted with a halogen atom, a hydroxyl group, a tri($C_1$-$C_7$)hydrocarbonsilyloxy group, a caroboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a hydroxyl group, a tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms; or an alicyclic group which may be substituted with a halogen atom, a hydroxyl group, a tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms and an alkoxy group having 1 to 4 carbon atoms; can be prepared according to the present invention by subjecting the 2-substituted-2-cyclopentenones represented by the formula (I-a-21):

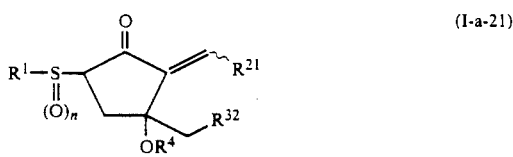

wherein $R^1$, $R^{21}$, $R^4$, n and the representation $\sim$ are as defined above; and $R^{32}$ represents a hydrogen atom or an aliphatic hydrocarbon group having 1 to 9 carbon atoms which may have as the substituent —COOR$^{51}$ (where $R^{51}$ is an alkyl group having 1 to 10 carbon atoms); —OR$^{61}$ (where $R^{61}$ is an acyl group having 2 to 7 carbon atoms; a tri($C_1$-$C_7$)hydrocarbonsilyl group; a group which forms an acetal bond together with the oxygen atom to which $R^{61}$ is bonded; an aromatic hydrocarbon group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms; or an alicyclic group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms and an alkoxy group having 1 to 4 carbon atoms; and subsequently subjecting the reaction product to an oxidation reaction, deprotection reaction and/or protection reaction, if desired.

In the above formula (I-a-21), $R^1$ is substituted or non-substituted hydrocarbon group having 1 to 10 carbon atoms, and specific examples of $R^1$ include the same specific examples as mentioned above for the above formula (I).

In the above formula (I-a-21), $R^{21}$ is an aliphatic hydrocarbon group having 1 to 10 carbon atoms which may have as the substituent —COOR$^{51}$ (where $R^{51}$ is an alkyl group having 1 to 10 carbon atoms); —OR$^{61}$ (where $R^{61}$ is an acyl group having 2 to 7 carbon atoms; a tri($C_1$-$C_7$)hydrocarbonsilyl group; a group which forms an acetal bond together with the oxygen atom to which $R^{61}$ is bonded; an aromatic hydrocarbon group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a hydroxyl group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms; or an aliphatic group which may be substituted with a halogen atom, a tri($C_1$-$C_7$)hydrocarbonsilyloxy group, an acyloxy group having 2 to 7 carbon atoms, an acyloxy group having 2 to 7 carbon atoms, an alkoxycarbonyl group having 2 to 5 carbon atoms, an alkyl group having 1 to 4 carbon atoms and an alkoxy group having 1 to 4 carbon atoms. Specific examples of $R^{21}$ include the same specific examples as mentioned for $R^1$ in the above formula (I).

In the above formula (I-a-21), $R^{32}$ represents a hydrogen atom or an aliphatic hydrocarbon group having 1 to 9 carbon atoms which may have as the substituent —COOR$^{51}$ (where $R^{51}$ is an alkyl group having 1 to 10 carbon atoms); —OR$^{61}$ (where $R^{61}$ is an acyl group having 2 to 7 carbon atoms; a tri($C_1$-$C_7$)hydrocarbonsilyl group; a group which forms an acetal bond together with the oxygen atom to which $R^{61}$ is bonded; an aromatic hydrocarbon group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a tri($C_1$-$C_7$)hydrocarbonsilyloxy group, an acyloxy group having 2 to 7 carbon atoms, an acyl groups having 2 to 7 carbon atoms, an alkoxycarbonyl group having 2 to 5 carbon atoms, an alkoxy group having 1 to 4 carbon atoms, and an alkoxy group having 1 to 4 carbon atoms; or an alicyclic group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms and an alkoxy group having 1 to 4 carbon atoms. Specific examples of $R^{32}$ include the same specific examples as mentioned for $R^{33}$ in the above formula (I'').

In the above formula (I-a-21), $R^4$ represents a hydrogen atom, or a protected group of protected hydroxyl group. Specific examples of $R^4$ include a hydrogen atom; alkyl groups such as methyl, ethyl, propyl, and isopropyl; tri($C_1$-$C_7$)hydrocarbonsilyl groups such as trimethylsilyl, triethylsilyl, t-butyldimethylsilyl, t-butyldiphenylsilyl, and tribenzylsilyl; groups which form an acetal bond together with the protective group of the protected hydroxyl group such as methoxymethyl, 1-ethoxyethyl, 2-methoxyethoxymethyl, and tetrahydropyran-2-yl and acyl groups such as acetyl, propionyl, and butylyl.

According to the present invention, the 2-substituted-2-cyclopentenones represented by the above formula (I-a-21) can be prepared by forming an alkylidene group at the 4-position of the cyclopentenone skeleton by an elimination reaction, carrying out the oxidation reaction when S bonded at the 2-position is to be converted to sulfoxide or sulfone, and further, subjecting the reaction product to a deprotection reaction of a hydroxyl group or carboxyl group, and/or a protection reaction.

In the process of the present invention, the compound of the above formula (I-a-21) is subjected to an elimination reaction, which is preferably practiced by using an acidic compound. As the acidic compound, there may be employed organic carboxylic acids such as acetic acid, propanoic acid, butanoic acid, oxalic acid, malonic acid, tartaric acid, and benzoic acid; inorganic acids such as hydrochloric acid, sulfuric acid, nitric acid, and hydrofluoric acid; organic sulfonic acids such as p-toluenesulfonic acid, methanesulfonic acid, and benzenesulfonic acid, but preferably, acetic acid is used.

The solvent to be used includes water; alcohols such as methanol and ethanol; ethers such as ether, tetrahydrofuran, dioxane, and dimethoxyethane; aprotic polar solvents such as hexamethylphosphoric triamide, dimethylformamide, and dimethylsulfoxide; halogenated hydrocarbons such as dichloromethane and chloroform; and acetonitrile and nitromethane, which may be used alone or as a mixture thereof.

The acidic compound may be be used at a ratio preferably of 0.001 to 1000 equivalents per 1 mol of the compound of the above formula (I-a-21).

Preferably, the amount of the solvent used is 1 to 1000-fold volume, more preferably 5 to 100-fold volume, relative to the compound represented by the above formula (I-a-21). The reaction temperature may differ depending on the starting compound, the acidic compound, and the amount of solvent employed, but preferably is from $-20°$ C. to $100°$ C., more preferably from $0°$ C. to $50°$ C. The reaction time, which is differs depending on the conditions, is about 0.1 to 100 hours. The progress of the reaction is monitored by a method such as chromatography.

After completion of the reaction, the desired compound may be purified by a conventional means such as extraction, washing, concentration, and chromatography, or combination thereof, but the unpurified reaction mixture can be subjected as such, without isolation of the desired compound, to an oxidation reaction, deprotection reaction or protection reaction, if desired, to prepare the 2-substituted-2-cyclopentenones represented by the above formula (I-a-3). This oxidation reaction, deprotection reaction and/or protection reaction can be carried out by the same method as used in the preparation of the 2-substituted-2-cyclopentenones represented by the above formula (I-b-11) from the 2-substituted-2-cyclopentenones represented by the above formula (I-b-10).

Of the 2-substituted-2-cyclopentenones of the above formula (I) of the present invention, the 2-substituted-2-cyclopentenones represented by the following formula (I-2):

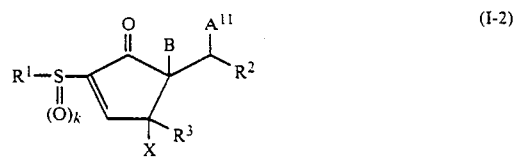
(I-2)

wherein $R^1$, $R^2$, $R^3$ and X are as defined above; $A^{11}$ and B are such that $A^{11}$ represents a hydroxyl group or

and B represents a hydrogen atom or $A^{11}$ and B together represent a single bond; k is 1 or 2; and i is 0, 1, or 2, can be prepared according to the present invention by subjecting the 2-substituted-2-cyclopentenones represented by the following formula (I-1):

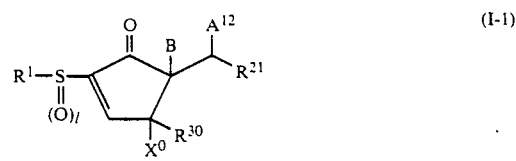
(I-1)

wherein $R^1$ and $R^{21}$ are as defined above; $A^{12}$ and B are such that $A^{12}$ represents a hydroxyl group or

and B represents a hydrogen atom or $A^{12}$ and B together represent a single bond; and $R^{30}$ represents a substituted or non-substituted aliphatic hydrocarbon group having 1 to 10 carbon atoms, when $R^{30}$ is a single bond and is bonded to the cyclopentene skeleton, $X^0$ represents a hydrogen atom, a hydroxyl group or a protected hydroxyl group, and when $R^{30}$ is a double bond and bonded to the cyclopentene skeleton, $X^0$ represents a bonding arm constituting a part of said double bond; l is 0 or 1; and j is 0, 1, or 2; to oxidation reaction, and then to deprotection reaction and/or protection reaction, if desired.

In the above formula (I-1), $A^{12}$ and B represent a combination in which B is a hydrogen atom when $A^{12}$ is a hydroxyl group or

or $A^{12}$ and B are mutually bonded together to represent one bonding arm. Specific examples of $A^{12}$ and B include the same specific examples as mentioned above for the above formula (I).

In the above formula (I-1), $R^1$ represents a substituted or non-substituted hydrocarbon group having 1 to 10 carbon atoms. Specific examples of $R^1$ include the same specific examples as mentioned above for the above formula (I).

In the above formula (I-1), $R^{21}$ represents an aliphatic hydrocarbon group having 1 to 10 carbon atoms which may have as the substituent —COOR$^{51}$ (where $R^{51}$ represents a hydrogen atom, an alkyl group having 1 to 10 carbon atoms or one equivalent cation); —OR$^{61}$ (where $R^{61}$ is an acyl group having 2 to 7 carbon atoms; a tri($C_1$-$C_7$)hydrocarbonsilyl group; a group which forms an acetal bond together with the oxygen atom to which $R^{61}$ is bonded; an aromatic hydrocarbon group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms; or an alicyclic group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms and an alkoxy group having 1 to 4 carbon atoms. Specific examples of $R^{21}$ include the same specific examples as mentioned above for $R^2$ in the above formula (I).

In the above formula (I-1), $R^{30}$ represents a substituted or non-substituted aliphatic hydrocarbon group having 1 to 10 carbon atoms. Where $R^{30}$ is a single bond and bonded to the cyclopentene skeleton, $X^0$ represents a hydrogen atom, a hydroxyl group or a protected hydroxyl group, and when $R^{30}$ is a double bond and bonded to the cyclopentene skeleton, $X^0$ represents a bond in said double bond. Specific examples of $R^{30}$ and $X^{30}$ include the same specific examples as mentioned above for $R^3$ and X, respectively, in the above formula (I).

In the above formula (I-1), l represents 0 or 1 and j represents 0, 1 or 2. In the process of the present invention, the 2-substituted-2-cyclopentenones represented by the above by subjecting the compound of the above formula (I-1) to and oxidation reaction, and further to a deprotection reaction and/or protection reaction, if necessary, formula (I-2) can be prepared. This oxidation reaction, deprotection reaction and/or protection reaction can be carried out by the same method as used in the preparation of the 2-substituted-2-cyclopentenones represented by the above formula (I-b-11) from the 2-substituted-2-cyclopentenones represented by the above formula (I-b-10).

In the present invention, the preparation processes according to the embodiments as shown below are applicable.

1. A process for preparing the 2-substituted-2-cyclopentenones represented by the following formula (I-b-11):

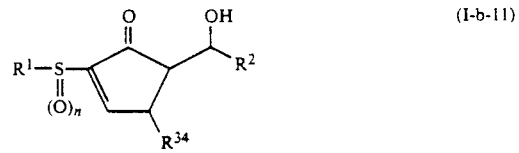

wherein $R^1$ is as defined above;

As defined above, $R^2$ and $R^{34}$ are preferably aliphatic hydrocarbon groups having 1 to 10 carbon atoms which may have as the substitutent —COOR$^5$ (where $R^5$ represents a hydrogen atom, an alkyl group having 1 to 10 carbon atoms or one equivalent cation); —OR$^6$ (where $R^6$ is a hydrogen atom; an acyl group having 2 to 7 carbon atoms; a tri($C_1$-$C_7$)hydrocarbonsilyl group; a group which forms an acetal bond together with a oxygen atom to which $R^6$ is bonded; an aromatic hydrocarbon group which may be also substituted with a halogen atom, a hydroxyl group, a tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a hydroxyl group, a tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms; or an alicyclic group which may be substituted with a halogen atom, a hydroxyl group, a tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms and an alkoxy group having 1 to 4 carbon atoms; and n represents 0, 1 or 2, which comprises subjecting the 2-cyclopentenones represented by the following formula (III-a):

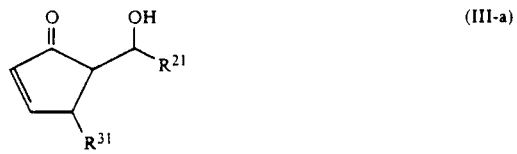

wherein $R^{21}$ and $R^{31}$ represent an aliphatic hydrocarbon group having 1 to 10 carbon atoms which may have as the substituent —COOR$^{51}$ (where $R^{51}$ is an alkyl group having 1 to 10 carbon atoms); —OR$^{61}$ (where $R^{61}$ is an acyl group having 2 to 7 carbon atoms; a tri($C_1$-$C_7$)hydrocarbonsilyl group; a group which forms an acetal bond together with a hydrogen atom to which $R^{61}$ is bonded; an aromatic hydrocarbon group may be also substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms; or an alicyclic group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms and an alkoxy group having 1 to 4 carbon atoms; to an epoxydization reaction to obtain the 2,3-epoxycyclopentanones of the following formula (IV-a-1):

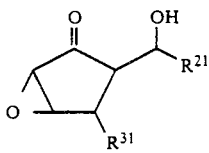

wherein $R^{21}$ and $R^{31}$ are as defined above, then reacting thiols represented by the following formula (V):

$R^1$—SH  (V)

wherein $R^1$ represents a substituted or non-substituted hydrocarbon group having 1 to 10 carbon atoms with said 2,3-epoxycyclopentanones in the presence of a basic compound, alumina and/or silica gel, and subsequently subjecting the reaction product, if necessary, to an oxidation reaction, deprotection reaction and/or protection reaction.

2. A process for preparing the 2-substituted-2-cyclopentenones represented by the following formula (I-a-1):

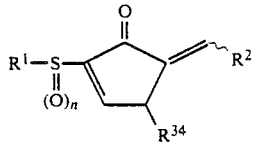

wherein $R^1$, $R^2$, $R^{34}$, and n are as defined above; and the representation ⁓ denotes that the substituent bonded to the double bond is in an E-configuration or a Z-configuration or mixtures thereof at any desired ratio which comprises dehydrating the 2-substituted-2-cyclopentenones represented by the following formula (I-b-10):

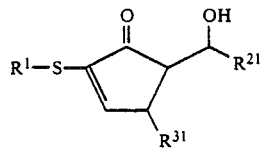

wherein $R^1$, $R^{21}$ and $R^{31}$ are as defined above, and subsequently subjecting the dehydrated product to oxidation reaction, deprotection reaction and/or protection reaction.

3. A process for preparing the 2-substituted-2-cyclopentenones represented by the following formula (I-a-1):

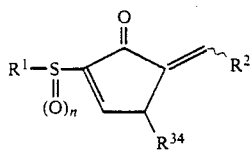

wherein $R^1$, $R^2$, $R^{34}$, n and the representation ⁓ are as defined above,
and the 2-substituted-2-cyclopentenones represented by the following formula (I-b-12):

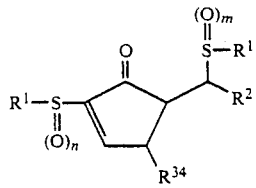

wherein $R^1$, $R^2$, $R^{34}$, and n are as defined above, and m represents 0, 1 or 2, which comprises allowing the 2,3-epoxycyclopentanones represented by the following formula (IV-a-2):

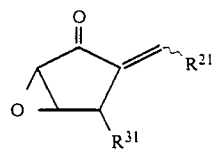

wherein $R^{21}$, $R^{31}$ and the representation ⁓ are as defined above, to react with thiols represented by the following formula (V):

$R^1$—SH  (V)

wherein $R^1$ is as defined above, in the presence of a basic compound, alumina and/or silica gel, and then carrying out an oxidation reaction, deprotection reaction and/or protection reaction, if desired.

4. A process for preparing the 2-substituted-2-cyclopentenones represented by the following formula (I-b-2):

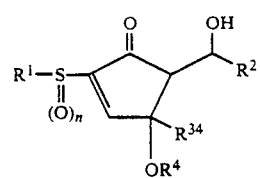

wherein $R^1$, $R^2$, $R^{34}$ and n are as defined above; and $R^4$ represents a hydrogen atom or a protected group of the protected hydroxyl group, which comprises subjecting the 2-substituted-2-cyclopentenones represented by the following formula (III-b):

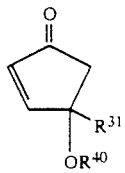

(III-b)

wherein $R^{31}$ represents an aliphatic hydrocarbon group having 1 to 10 carbon atoms which may have as the substituent —$COOR^{51}$ (where $R^{51}$ is an alkyl group having 1 to 10 carbon atoms); —$OR^{61}$ (where $R^{61}$ is an acyl group having 2 to 7 carbon atoms; a tri($C_1$–$C_7$)hydrocarbonsilyl group; a group which forms an acetal bond together with the oxygen atom to which $R^{61}$ is bonded; an aromatic hydrocarbon group which may be substituted with a halogen atom, a tri($C_1$–$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a tri($C_1$–$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms; or an alicyclic group which may be substituted with a halogen atom, a tri($C_1$–$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms and an alkoxy group having 1 to 4 carbon atoms; and $R^{40}$ represents a hydrogen atom or a protected group of the protected hydroxyl group, to an epoxydization reaction to obtain the 2,3-epoxycyclopentanones represented by the following formula (IV-b-1):

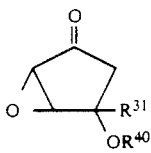

(IV-b-1)

wherein $R^{31}$ $R^{40}$ and are as defined above, then reacting the thiols represented by the following formula (V):

$R^1$—SH (V)

wherein $R^1$ is as defined above, with the 2,3-epoxycyclopentanones in the presence of a basic compound, alumina and/or silica gel, and further protecting the hydroxyl group, if desired, to obtain the 2-substituted-2-cyclopentenones represented by the following formula (I-c-1):

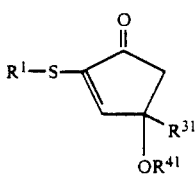

(I-c-1)

wherein $R^1$ and $R^{31}$ are as defined above; and $R^{41}$ represents a protected group of the protected hydroxyl group, and carrying out an aldol condensation reaction which aldehydes represented by the following formula (II):

OHC—$R^{21}$ (II)

wherein $R^{21}$ is as defined above, and subsequently, subjecting the reaction product to an oxidation reaction, deprotection reaction and/or protection reaction, if desired.

5. A process for preparing the 2-substituted-2-cyclopentenones represented by the following formula (I-a-2):

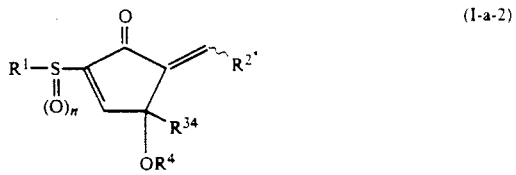

(I-a-2)

wherein $R^1$, $R^2$, $R^{34}$, $R^4$, n and the representation are as defined above, which comprises dehydrating the 2-substituted-2-cyclopentenones represented by the following formula (I-b-20):

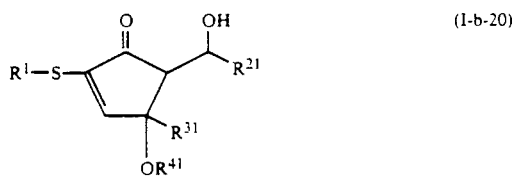

(I-b-20)

wherein $R^1$, $R^{21}$, $R^{31}$ and $R^{41}$ are as defined above, and subsequently subjecting the dehydrated product to oxidation reaction, deprotection reaction and/or protection reaction, if desired.

6. A process for preparing the 2-substituted-2-cyclopentenones represented by the following formula (I-a-3'):

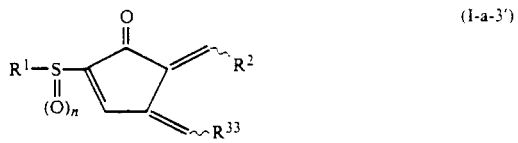

(I-a-3')

wherein $R^1$, $R^2$, n and the representation $\sim$ are as defined above; and $R^{33}$ represents a hydrogen atom or an aliphatic hydrocarbon group having 1 to 9 carbon atoms having as the substituent —$COOR^5$ (where $R^5$ represents hydrogen atom, an alkyl group having 1 to 10 carbon atoms or one equivalent cation); —$OR^6$ (where $R^6$ is an acyl group having 2 to 7 carbon atoms; a tri($C_1$–$C_7$)hydrocarbonsilyl group; a group which forms an acetal bond together with the oxygen atom to which $R^6$ is bonded; an aromatic hydrocarbon group which may be substituted with a halogen atom, a hydroxyl group, a tri($C_1$–$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a hydroxyl group, a tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms; or an alicyclic group which may be substituted with a halogen atom, a hydroxyl group, a tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms and an alkoxy group having 1 to 4 carbon atoms; which comprises subjecting the 2-substituted-2-cyclopentenones represented by the formula (I-a-21):

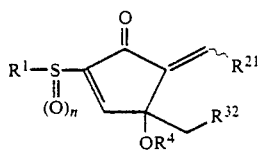

wherein $R^1$, $R^{21}$, $R^4$, n and the representation $\sim$ are as defined above; and $R^{32}$ represents a hydrogen atom or an aliphatic hydrocarbon group having 1 to 9 carbon atoms which may have as the substituent —$COOR^{51}$ (where $R^{51}$ is an alkyl group having 1 to 10 carbon atoms); —$OR^{61}$ (where $R^{61}$ is an acyl group having 2 to 7 carbon atoms; a tri($C_1$-$C_7$)hydrocarbonsilyl group; a group which forms an acetal bond together with the oxygen atom to which $R^{61}$ is bonded; an aromatic hydrocarbon group which may be substituted with a halogen atom, a tri($C_1$-$C_7$)hydrocarbonsilyloxy group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms); an aromatic hydrocarbon group which may be substituted with a halogen atom, a hydroxy group, a tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, and an alkoxy group having 1 to 4 carbon atoms; or an alicyclic group which may be substituted with a halogen atom, a hydroxyl group, a tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms and an alkoxy group having 1 to 4 carbon atoms, and subsequently subjecting the reaction product to oxidation reaction, deprotection reaction and/or protection reaction, if desired.

7. A process for preparing the 2-substituted-2-cyclopentenones represented by the following formula (I-2):

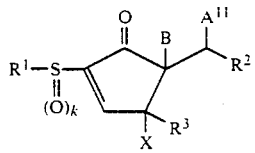

wherein $R^1$, $R^2$, $R^3$ and X are as defined above; $A^{11}$ and B are such that $A^{11}$ represents a hydroxyl group or

and B represents a hydrogen atom or $A^{11}$ and B together represent a single bond; k represents 1 to 2; and i represents 0, 1 or 2, which comprises subjecting the 2-substituted-2-cyclopentenones represented by the following formula (I-1):

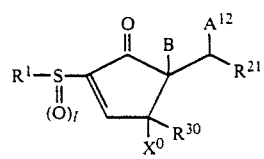

wherein $R^1$ and $R^{21}$ are as defined above: $A^{12}$ and B are such that $A^{12}$ represents a hydroxyl group or

and B represents a hydrogen atom or $A^{12}$ and B together represent a single bond, and $R^{30}$ represents a substituted or non-substituted aliphatic hydrocarbon group having 1 to 10 carbon atoms, when $R^{30}$ is a single bond and is bonded to the cyclopentene skeleton, $X^0$ represents a hydrogen atom, hydroxyl group or a protected hydroxyl group, and when $R^{30}$ is a double bond and bonded to the cyclopentene skeleton, $X^0$ represents a bonding arm constituting a part of said double bond; l represents 0 or 1; and j represents 0, 1, or 2, to an oxidation reaction, and then to a deprotection reaction and/or protection reaction, if desired.

8. A process for preparing 2-substituted-2-cyclopentenones according to the above items 1 or 4, wherein the epoxydization reaction is carried out by using hydrogen peroxide in the presence of an alkali metal hydroxide or carbonate.

9. A process for preparing 2-substituted-2-cyclopentenones according to the above items 1, 3, 4 or 8, wherein the basic compound to be used in the reaction with the thiols represented by the above formula (V) is an alkali metal hydroxide or carbonate, or an amine.

10. A process for preparing 2-substituted-2-cyclopentenones according to the above items 4, 8 or 9, wherein the aldol condensation reaction is carried out in the presence of a basic compound and dibutylborontrifluoremethanesulfonic acid.

11. A process for preparing 2-substituted-2-cyclopentenones according to the above items 4, 8 or 9, wherein the aldol condensation reaction is carried out in the presence of lithium diisopropylamide.

12. A process for preparing 2-substituted-2-cyclopentenones according to the above items 2 or 5, wherein the dehydration reaction of the above formula (I-b-10) or (I-b-20) is carried out by using a basic compound and a reactive derivative of an organic sulfonic acid.

13. A process for preparing 2-substituted-2-cyclopentenones according to the above items 1 to 12, wherein the oxidation reaction is carried out by using an organic peracid.

14. A process for preparing 2-substituted-2-cyclopentenones according to the above items 1 to 12, wherein the oxidation reaction is carried out by using an organic periodic acid salt.

The compound according to the present invention can be administered by oral, subcutaneous, intramuscular, intravenous, intraarterial, and suppository administration, etc., methods.

Solid preparations or liquid preparations can be formed for oral administration, and include, for example, tablets, pills, powders, granules, solutions, suspensions or capsules. When preparing tablets by a conventional method, excipients such as lactose, starch, calcium carbonate, crystalline cellulose or silicic acid; binders such as carboxymethyl cellulose, methyl cellulose, calcium phosphate or polyvinyl pyrrolidone; disintegrating agents such as sodium alginate, sodium hydrogen carbonate, sodium lauryl sulfate or stearic acid monoglyceride; humectants such as glycerine; absorbers such as kaolin, and colloidal silica; and lubricants such as talc and granular boric acid may be employed.

Pills, powders or granules also can be prepared by conventional methods using the same additives as mentioned above.

Liquid preparations such as solutions and suspensions also can be prepared by conventional methods. As the carrier, for example, glycerol esters such as tricaprin, triacetin, iodated poppy seed oil fatty acid esters; water; alcohols such as ethanol; and oily bases such as fluid paraffin, coconut oil, soybean oil, sesame oil, and corn oil may be employed.

The powders, granules, liquid preparations as described above also can be enclosed within capsules of, for example, gelatin.

The pharmaceutically acceptable carrier in the present specification also includes other auxiliary agents, aromatic agents, stabilizers or preservatives conventionally used as optional components.

The preparation for parental administration may be a sterile aqueous or nonaqueous solution, suspension or emulsion. The nonaqueous solution or suspension may employ propylene glycol and polyethylene glycol, or a vegetable oil such as olive oil, an injectable organic ester such as ethyl oleate, and iodated poppy seed fatty acid esters as the carrier. The preparation also can contain auxiliary agents such as preservatives, humectants, emulsifiers, dispersing agents, and stabilizers. These solutions, suspensions and emulsions can be sterilized by a treatment such as filtration through bacteria-retaining filter, formulation with a sterilizer, or irradiation. It is also possible to prepare a sterile solid preparation, which is dissolved in sterile water or a sterile solvent for injection immediately before use.

The compounds of the present invention also can be used by forming inclusion compounds together with α, β or γ-cyclodextrin or methylated cyclodextrin, and may be injectable preparations in the lipogenated form.

The effective dose of the compounds of the present invention depends on the age, sex, and condition of the patient, but generally may be administered at $10^2$ to $10^5$ μg/Kg/day, preferably $5 \times 10^2$ to $10^4$ μg/Kg/day.

The 2-substituted-2-cyclopentenones of the present invention have a potent growth inhibitory effect against L1210 leukemia cells even at a low concentration, are useful as antitumor agents.

Furthermore, the present compounds have the activities of enhancing the alkali phosphatase activity of human osteoblast, and further, enhancing the calcium and phosphorus contents in osteoblast. Accordingly, the present compounds are also useful as a bone formation accelerator, and are effective for the therapy or prophylaxis of osteoporosis or osteomalacia.

Furthermore, the present compounds are expected to exhibit an antiviral activity or antibacterial activity and are very useful components as the pharmaceutical products.

EXAMPLES

The present invention is described in detail below with reference to Examples.

EXAMPLE 1

Synthesis of 2,3-epoxy-5-(1-hydroxy-6-methoxycarbonylhexyl-4-(3-t-butyldimethylsilyloxy-1-octenyl)cyclopentanone

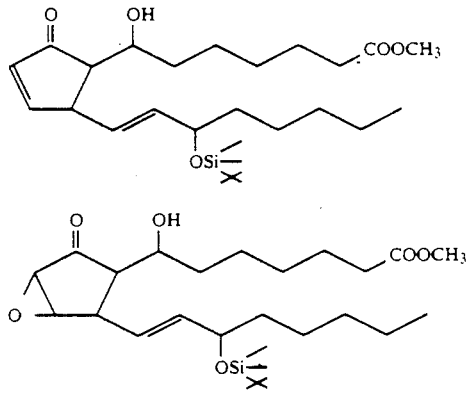

A solution of 3.30 g of 5-(1-hydroxy-6-methoxycarbonylhexyl)-4-(3-t-butyldimethylsilyloxy-1-octenyl)-2-cyclopentenone in methanol (25 ml) was cooled to 0° C., and 48 ml of an aqueous 30% hydrogen peroxide and 0.48 ml of an aqueous 1N sodium hydroxide were dropwise added thereto. After stirring at 0° C. for 3 hours, the reaction mixture was extracted with an addition of ethyl acetate and saturated aqueous ammonium chloride, and the extract was washed with saturated aqueous sodium chloride, dried over anhydrous magnesium sulfate and filtered, followed by concentration. The concentrate was subjected to silica gel chromatography to give 2.54 g (yield 74%) of 2,3-epoxy-5-(1-hydroxy-6-methoxycarbonylhexyl)-4-(3-t-butyldimethylsilyloxy-1-octenyl)cyclopentanone.

Spectrum data
$^1$H-HMR CDCl$_3$ δ
−0.03 (3H, s), 0.00 (3H, s), 0.84 (9H, s), 0.7–1.1 (3H, brt), 1.1–2.3 (20H, m), 3.4–3.5 (1H,m), 3.61 (3H, s), 3.68 (1H, brs), 4.0–4.1 (1H,m), 5.5–5.7 (2H, m)

EXAMPLES 2 TO 5

The 2,3-epoxycyclopentanones listed in Table 1 were obtained in the same manner as in Example 1.

TABLE 1

| Example No. | Starting compound 2-cyclopentanones | 2,3-epoxy cyclopentanones | Yield (%) | NMR (δ CDCl₃) |
|---|---|---|---|---|
| 2 | 5-(1-hydroxy-6-methoxycarbonyl-2-hexynyl)-4-(3-t-butyldimethylsilyloxy-3-cyclopentyl-1-propenyl)-2-cyclopentenone | 2,3-epoxy-5-(1-hydroxycarbonyl-2-hexynyl)-4-(3-t-butyldimethylsilyloxy-3-cyclopentyl-1-propenyl)cyclopentanone | 51 | 0.00(3H, s), 0.05 (3H, s), 0.89(9H, s), 1.2-2.0(11H, m), 2.0-2.6(5H, m), 3.1-3.3 (1H, m), 3.50(1H, d, $J=2.5Hz$), 3.69 (3H, s), 3.77(1H, d, $J=2.5Hz$), 3.8-4.05 (1H, m), 4.4-4.9 (2H, m), 5.3-5.9 (2H, m) |
| 3 | 5-(1-hydroxy-6-methoxycarbonyl-5-hexenyl)-4-(3-t-butyldimethylsilyloxy-5-methyl-1-nonenyl)-2-cyclopentenone | 2,3-epoxy-5-(1-hydroxycarbonyl-6-methoxycarbonyl-5-hexenyl)-4-(3-t-butyldimethylsilyloxy-5-methyl-1-nonenyl)cyclopentanone | 63 | 0.01(3H, s), 0.06 (3H, s), 0.89(9H, s), 0.7-1.1(6H, m), 1.1-2.7 (17H, m), 3.0-3.3 (1H, m), 3.49(1H, d, $J=2.5Hz$), 3.68 (3H, s), 3.79(1H, d, $J=2.5Hz$), 3.6-4.6 (2H, m), 5.4-5.9 (2H, m), 5.87(1H, d, $J=16.0Hz$), 7.03(1H, dt, $J=16.0, 7.2Hz$) |
| 4 | 5-(1-hydroxy-6-methoxycarbonylhexyl)-4-[3-(tetrahydropyran-2-yloxy)-3-cyclohexyl-1-propenyl]-2-cyclopentenone | 2,3-epoxy-5-(1-hydroxycarbonyl-6-methoxyhexyl)-4-[3-(tetrahydropyran-2-yloxy)-3-cyclohexyl-1-propenyl]cyclopentanone | 43 | 1.1-2.7(29H, m), 2.9-3.3(1H, m), 3.3-4.4 (5H, m), 3.69(3H, s), 4.5-5.0(2H, m), 5.3-5.8 (2H, m) |

TABLE 1-continued
| Example No. | Starting compound 2-cyclopentanones | 2,3-epoxy cyclopentanones | Yield (%) | NMR (δ CDCl₃) |
|---|---|---|---|---|
| 5 | 5-(1-hydroxy-3-phenyl-2-propenyl)-4-butyl-2-cyclopentenone 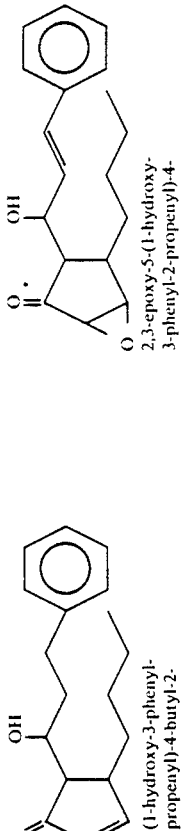 | 2,3-epoxy-5-(1-hydroxy-3-phenyl-2-propenyl)-4-butylcyclopentanone 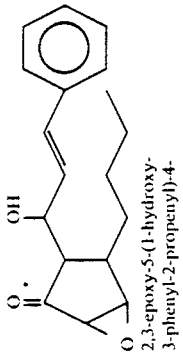 | 69 | 0.7–1.1(3H, m), 1.1–3.1 (9H, m), 3.3–3.6 (1H, m), 3.49(1H, d, J=2.6Hz), 3.76(1H, d, J=2.6Hz), 4.3–4.7 (1H, m), 6.4–6.8 (1H, m), 7.0–8.0 (5H, m) |

EXAMPLE 6

Synthesis of 2-methylthio-5-(1-hydroxy-6-methoxycarbonylhexyl)-4-(3-t-butyldimethylsilyloxy-1-octenyl)-2-cyclopentenone

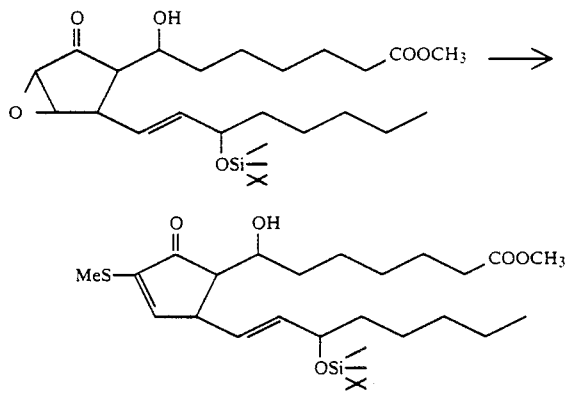

A solution of sodium thiomethoxide (2.30 g) in methanol (100 ml) was cooled to 0° C., acetic acid (2.82 ml) was added, the mixture was stirred for 5 minutes, Triethylamine (915 ml) was added, and a solution of 2,3-epoxy-5-(1-hydroxy-6-methoxycarbonylhexyl)-4-(3-t-butyldimethylsilyloxy-1-octenyl)cyclopentanone (3.26 g) in methanol (40 ml) was added. After stirring at room temperature for 12 hours, water was added to the mixture, and the mixture extracted with ethyl acetate. The extract was washed with a saturated aqueous sodium chloride solution, dried over anhydrous magnesium sulfate and filtered, followed by concentration. The concentrate was subjected to silica gel chromatography to give 3.47 g (yield 96%) of 2-methylthio-5-(1-hydroxy-6-methoxycarbonylhexyl)-4-(3-t-butyldimethylsilyloxy-1-octenyl)-2-cyclopentenone.

Spectrum data
$^1$H-NMR CDCl$_3$ δ
0.00 (3H, s), 0.03 (3H, s), 0.87 (9H, s), 0.7–1.1 (3H, brt), 1.1–2.3 (20H, m), 2.33 (3H, s), 3.1–3.3 (1H, m), 3.63 (3H, s), 3.6–3.8 (1H, brs), 3.9–4.2 (1H, m), 5.4–5.6 (2H, m), 6.78 (1H, d, J=3 Hz).

EXAMPLES 7–9

The 2-substituted-2-cyclopentenes listed in Table 2 were obtained in the same manner as in Example 6.

TABLE 2

| Example No. | Starting compound | 2-Substituted-2-cyclopentenones | Yield (%) | NMR (δ CDCl$_3$) |
|---|---|---|---|---|
| 7 | 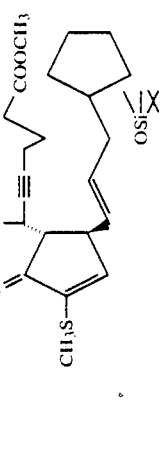<br>2,3-epoxy-5-(1-hydroxy-6-methoxycarbonyl-2-hexynyl)-4-(3-t-butyldimethylsilyloxy-3-cyclopentyl-1-propenyl)cyclopentanone | 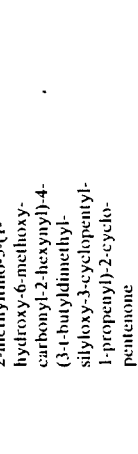<br>2-methylthio-5-(1-hydroxy-6-methoxycarbonyl-2-hexynyl)-4-(3-t-butyldimethylsilyloxy-3-cyclopentyl-1-propenyl)-2-cyclopentenone | 54 | 0.04(6H, s), 0.89 (9H, s), 1.1–2.1 (11H, m), 2.1–3.1 (6H, m), 2.32(3H, s), 3.1–3.5(1H, m), 3.68 (3H, s), 3.8–4.0 (1H, m), 4.6–4.85 (1H, m), 5.3–5.9 (2H, m), 6.90(1H, d, J = 3.0Hz) |
| 8 | 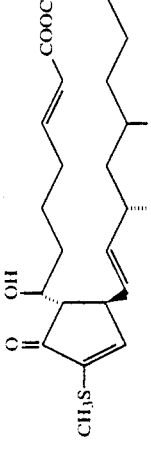<br>2,3-epoxy-5-(1-hydroxy-6-methoxycarbonyl-5-hexenyl)-4-(3-t-butyldimethylsilyloxy-5-methyl-1-nonenyl)cyclopentanone | 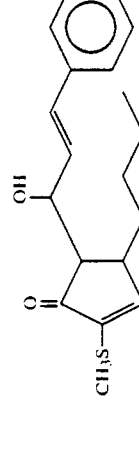<br>2-methylthio-5-(1-hydroxy-6-methoxycarbonyl-5-hexenyl)-4-(3-t-butyldimethylsilyloxy-5-methyl-1-nonenyl)-2-cyclopentenone | 60 | 0.01(3H, s), 0.04 (3H, s), 0.89(9H, s), 0.7–1.1(6H, m), 1.1–2.7 (17H, m), 2.33(3H, s), 3.1–3.3(1H, m), 3.68 (3H, s), 3.6–3.9 (3H, m), 3.8–4.3 (1H, m), 5.4–5.8 (2H, m), 5.89(1H, d, J = 16.0Hz), 6.82(1H, d, J = 2.5Hz), 7.02 (1H, dt, J = 16.0, 7.4Hz) |
| 9 | 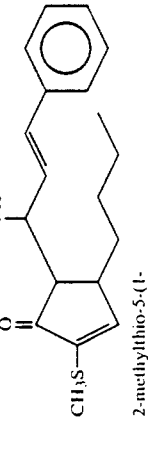<br>2,3-epoxy-5-(1-hydroxy-3-phenyl-2-propenyl)-4-butylcyclopentanone | 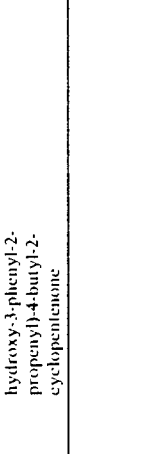<br>2-methylthio-5-(1-hydroxy-3-phenyl-2-propenyl)-4-butyl-2-cyclopentenone | 72 | 0.7–1.1(3H, m), 1.1–3.3 (9H, m), 2.34(3H, s), 3.3–3.6(1H, m), 4.3–4.7 (1H, m), 6.4–6.9 (2H, m), 7.0–8.0 (5H, m) |

EXAMPLE 10

Synthesis of 2-(2,3-dihydroxypropylthio)-5-(1-hydroxy-6-methoxycarbonyl-2-hexynyl)-4-(3-t-butyldimethylsilyloxy-3-cyclopentyl-1-propenyl)-2-cyclopentenone

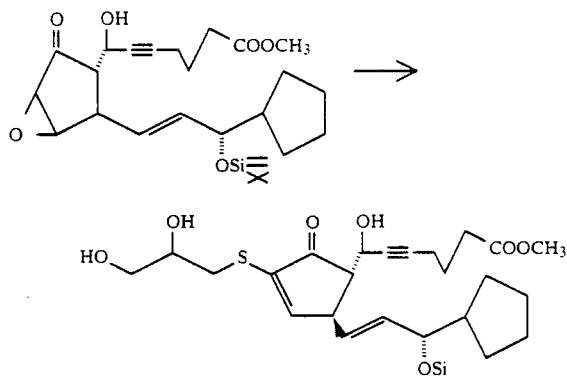

A 49 mg amount of 2,3-epoxy-5-(1-hydroxy-6-methoxycarbonyl-2-hexynyl)-4-(3-t-butyldimethylsilyloxy-3-cyclopentyl-1-propenyl)cyclopentanone was dissolved in 1 ml of methanol and 21 μl of triethylamine was added. Then, 12 mg of 2,3-dihydroxypropanethiol was added thereto, followed by stirring for 2 hours. The reaction mixture was poured on an aqueous saturated solution of potassium hydrogen sulfate, followed by extracting with ethyl acetate. The extracted solution was washed with a saturated sodium chloride solution and dried over anhydrous magnesium sulfate. After filtering and concentrating, the concentrate was subjected to silica gel chromatography to give 36 mg (yield 62%) of 2-(2,3-dihydroxypropylthio)-5-(1-hydroxy-6-methoxycarbonyl-2-hexynyl)-4-(3-t-butyldimethylsilyloxy-3-cyclopentyl-1-propenyl)-2-cyclopentenone.

Spectrum data
$^1$H-NMR CDCl$_3$ δ
0.05 (3H, s), 0.09 (3H, s), 0.89 (9H, s), 1.1–2.0 (11H, m), 2.0–2.7 (5H, m), 2.7–3.4 (6H, m), 3.67 (3H, s), 3.4–4.0 (4H, m), 4.5–4.9 (1H, m), 5.4–5.8 (2H, m), 7.1–7.3 (1H, m)

EXAMPLES 11–18

The 2-substituted-2-cyclopentenes listed in Table 3 were obtained in the same manner as in Example 10.

TABLE 3

| Example No. | Starting compound | | 2-Substituted-2-cyclopentenones | Yield (%) | NMR (δCDCl₃) |
|---|---|---|---|---|---|
| | 2,3-epoxycyclopentanones | Thiols | | | |
| 11 | 2,3-epoxy-5-(1-hydroxy-6-methoxycarbonyl-2-hexynyl)-4-(3-t-butyldimethylsilyloxy-1-propenyl)cyclopentanone | 5-methoxycarbonyl-pentane-1-thiol | 2-(5-methoxycarbonylpentylthio)-5-(1-hydroxy-6-methoxycarbonyl-2-hexynyl)-4-(3-t-butyldimethylsilyloxy-1-propenyl)-2-cyclopentenone | 71 | 0.04(6H, s), 0.89 (9H, s), 1.1–2.1 (17H, m), 2.1–3.1 (10H, m), 3.4–3.8 (1H, m), 3.67 (6H, s), 3.8–4.0 (1H, m), 4.6–4.85 (1H, m), 5.4–5.8 (2H, m), 6.92(1H, d, J = 3.2 Hz) |
| 12 | | 3-phenylpropane-1-thiol | 2-(3-phenylpropylthio)-5-(1-hydroxy-6-methoxycarbonyl-2-hexynyl)-4-(3-t-butyldimethylsilyloxy-1-propenyl)-2-cyclopentenone | 74 | 0.04(6H, s), 0.90 (9H, s), 1.0–3.0 (23H, m), 3.35–3.7 (1H, m), 3.68 (3H, s), 3.8–4.0 (1H, m), 4.6–4.8 (1H, m), 5.4–5.7 (2H, m), 6.89(1H, d, J = 2.8 Hz), 7.0–7.4(5H, m) |
| 13 | | Thiophenol | 2-phenylthio-5-(1-hydroxy-6-methoxycarbonyl-2-hexynyl)-4-(3-t-butyldimethylsilyloxy-1- | 91 | 0.07(6H, s), 0.89 (9H, s), 1.1–2.0 (11H, m), 2.0–2.7 (5H, m), 3.0–3.3 (1H, m), 3.4–3.6 (1H, m), 3.70 (3H, s), 3.8–4.0 (1H, m), 4.7–4.9 (1H, m), 5.4–5.8 (2H, m), 6.85(1H, d, J = 2.7 Hz), 7.2–7.7(5H, m) |

TABLE 3-continued

| Example No. | Starting compound | | 2-Substituted-2-cyclo-pentenones | Yield (%) | NMR (δCDCl₃) |
|---|---|---|---|---|---|
| | 2,3-epoxycyclopentanones | Thiols | | | |
| 14 | | 6-methoxynaphthalene-2-thiol | 2-(6-methoxynaphthyl-2-thio)-5-(1-hydroxy-6-methoxy-carbonyl-2-hexynyl)-4-(3-t-butyldimethylsilyloxy-3-cyclopentyl-1-propenyl)-2-cyclopentenone | 85 | 0.08(6H, s), 0.89 (9H, s), 1.1–2.0 (11H, m), 2.0–2.7(5H, m), 3.3–3.5(1H, m), 3.69(3H, s), 3.8–4.1(2H, m), 3.97(3H, s), 4.6–4.8(1H, m), 5.4–5.8(2H, m), 6.74(1H, d, J=2.7 Hz), 7.0–8.1(6H, m) |
| 15 | 2,3-epoxy-5-(1-hydroxy-6-methoxycarbonylhexyl)-4-(3-t-butyldimethylsilyloxy-1-octenyl)cyclopentanone | CH₃CH₂SH ethanethiol | 2-ethylthio-5-(1-hydroxy-6-methoxycarbonylhexyl)-4-(3-t-butyldimethylsilyloxy-1-octenyl)-2-cyclopentenone | 75 | 0.04(3H, s), 0.09 (3H, s), 0.89 (9H, s), 0.7–1.1 (6H, m), 1.1–2.7 (22H, m), 3.1–3.3 (1H, m), 3.68 (3H, s), 3.6–3.8 (1H, brs), 3.9–4.2 (1H, m), 5.3–5.7 (2H, m), 6.79(1H, d, J=2.9 Hz) |

TABLE 3-continued

| Example No. | Starting compound | | 2-Substituted-2-cyclopentenones | Yield (%) | NMR (δCDCl₃) |
|---|---|---|---|---|---|
| | 2,3-epoxycyclopentanones | Thiols | | | |
| 16 | 2,3-epoxy-5-(1-hydroxy-6-methoxycarbonyl)-4-(3-1-butyldimethylsilyloxy-5-methyl-1-nonenyl)cyclopentanone | 4-chlorophenyl-methanethiol | 2-(4-chlorophenylmethylthio)-5-(1-hydroxy-6-methoxycarbonyl-5-hexenyl)-4-(3-1-butyldimethylsilyloxy-5-methyl-1-nonenyl)-2-cyclopentenone | 62 | 0.01(3H, s), 0.05 (3H, s), 0.89 (9H, s), 0.7-1.1 (6H, m), 1.1-2.7 (17H, m), 3.1-3.3 (1H, m), 3.69 (3H, s), 3.6-3.9 (3H, m), 3.9-4.3 (1H, m), 5.3-5.9 (2H, m), 5.88(1H, d, J = 16.0 Hz), 6.85(1H, d, J = 2.7 Hz), 7.04 (1H, d, J = 16.0, 7.2 Hz), 7.26 (4H, s) |
| 17 | 2,3-epoxy-5-(1-hydroxy-6-methoxycarbonylhexyl)-4-[3-(tetrahydropyran-2-yloxy)-1-propenyl]cyclopentanone | CH₃CH₂SH | 2-ethylthio-5-(1-hydroxy-6-methoxycarbonylhexyl)-4-[3-(tetrahydropyran-2-yloxy)-1-propenyl]-2-cyclopentenone | 57 | 0.7-1.1(1H, m), 1.1-2.7(3H, m), 3.0-3.3(1H, m), 3.69(3H, s), 3.3-4.3(3H, m), 4.5-5.0(2H, m), 5.3-5.7(2H, m), 6.80(1H, d, J = 2.8 Hz) |
| 18 | 2,3-epoxy-5-(1-hydroxy-6-methoxycarbonylhexyl)-4-[3-(tetrahydropyran-2-yloxy)-3-cyclohexyl-1-propenyl]cyclopentanone | | 2-ethylthio-5-(1-hydroxy-6-methoxycarbonylhexyl)-4-[3-(tetrahydropyran-2-yloxy)-3-cyclohexyl-1-propenyl]-2-cyclopentenone | 82 | 0.7-1.1(3H, m), 1.1-3.3(9H, m), 2.30(3H, s), 3.3-3.6(1H, m), 4.3-4.7(1H, m), 6.4-6.9(2H, m), 6.9-8.0(9H, m) |

TABLE 3-continued

| Example No. | Starting compound | | 2-Substituted-2-cyclo-pentenones | Yield (%) | NMR (δCDCl₃) |
|---|---|---|---|---|---|
| | 2,3-epoxycyclopentanones | Thiols | | | |
| | 2,3-epoxy-5-(1-hydroxy-3-phenyl-2-propenyl)-4-butyl-cyclopentanone | 4-methylbenzene-thiol | 2-(4-methylphenylthio)-5-(1-hydroxy-3-phenyl-2-propenyl)-4-butyl-2-cyclopentenone | | |

EXAMPLE 19

Syntheses of
5-(6-methoxycarbonyl-1-methylthiohexyl)-2-methylthio-4-(1-octenyl)-2-cyclopentenone and
5-(6-methoxycarbonylhexylidene)-2-methylthio-4-(1-octenyl)-2-cyclopentenone

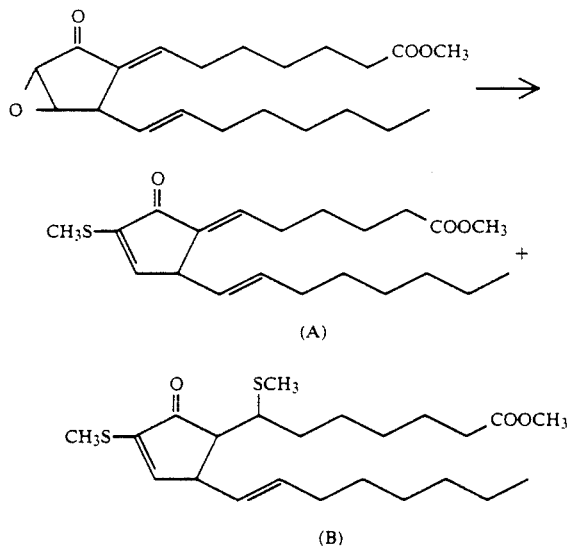

To a solution of 16.9 mg of sodium thiomethoxide dissolved in 1 ml of methanol, 39 μl of acetic acid was added under ice-cooling and stirring. A solution of 60 mg of 2,3-epoxy-4-(1-octenyl)-5-(6-methoxycarbonylhexylidene)cyclopentanone in 1 ml of methanol was added, then triethylamine (144 μl) was added, and the mixture was stirred at 0° C. for 4 hours. The reaction mixture was diluted with saturated aqueous ammonium chloride and extracted with ethyl acetate. The organic layer was washed with saturated aqueous sodium chloride, dried over anhydrous magnesium sulfate, filtered, concentrated and then provided for silica gel column chromatography to give 16.7 mg (yield 20%) of 5-(6-methoxycarbonyl-1-methylthiohexyl)-2-methylthio-4-(1-octenyl)-2-cyclopentenone and 9.0 mg (yield 13%) of 5-(6-methoxycarbonylhexyl)-2-methylthio-4-(1-octenyl)-2-cyclopentenone.

Spectrum data
(A) 1H-NMR (CDCl$_3$) δ
0.89 (3H, brt, J=5.5 Hz), 1.0–2.5 (20H, m), 2.37 (3H, s), 3.68 (3H, s), 3.96 (1H, brd, J=4.0 Hz), 4.20 (1H, dd, J=15.0, 8.5 Hz), 4.67 (1H, dt, J=15.0, 6.4 Hz), 6.5–6.8 (2H, m).

(B) 1H-NMR (CDCl$_3$) δ
0.89 (3H, brt, J=5.0 Hz), 1.1–1.9 (16H, m), 2.06 and 2.08 (3H, s), 1.9–2.7 (5H, m), 2.37 (3H, s), 3.0–3.3 (1H, m), 3.4–3.6 (1H, m), 3.69 (3H, s), 5.36 (1H, dd, J=15.5, 7.8 Hz), 5.61 (1H, dt, J=15.5, 7.8 Hz), 6.87 and 6.90 (1H, d, J=3.0 Hz).

EXAMPLE 20

Synthesis of
2-methylthio-5-(1-hydroxy-6-methoxycarbonylhexyl)-4-(3-hydroxy-1-octenyl)-2-cyclopentenone

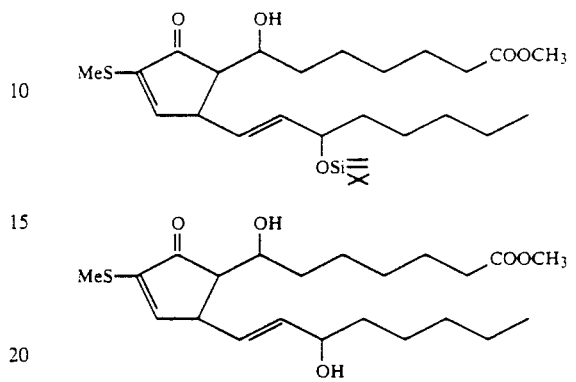

To 350 mg of 2-methylthio-5-(1-hydroxy-6-methoxycarbonylhexyl)-4-(3-t-butyldimethylsilyloxy-1-octenyl)-2-cyclopentenone obtained in Example 6 was added a solvent mixture of 10 ml of acetic acid, 5 ml of tetrahydrofuran, and 5 ml of water, and the mixture was stirred for 24 hours. Toluene was then added, and after concentration, the concentrate was diluted with saturated aqueous sodium hydrogencarbonate and extracted with ethyl acetate. Subsequently, the extract was washed with saturated aqueous sodium chloride, dried over anhydrous magnesium sulfate, filtered and concentrated, followed by silica gel chromatography to give 178 mg (yield 65%) of 2-methylthio-5-(1-methoxycarbonylhexyl)-4-(3-hydroxy-1-octenyl)-2-cyclopentenone.

Spectrum data
1H-NMR CDCl$_3$ δ
0.89 (3H, brt), 1.1–2.4 (21H, m), 2.34 (3H, s), 3.1–3.4 (1H, m), 3.65 (3H, s), 3.6–3.9 (1H, m), 3.9–4.2 (1H, m), 5.2–5.9 (2H, m), 6.79 (1H, d, J=3 Hz).

EXAMPLE 21

Synthesis of
2-methylsulfinyl-5-(1-hydroxy-6-methoxycarbonylhexyl)-4-(3-hydroxy-1-octenyl)-2-cyclopetenone

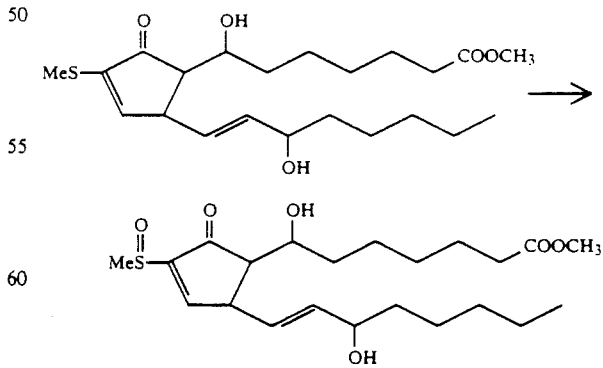

To a solution of 35 mg of 2-methylthio-5-(1-hydroxy-6-methoxycarbonylhexyl)-4-(3-hydroxy-1-octenyl)-2-cyclopentenone obtained in Example 20 dissolved in 5 ml of dichloromethane was added 17 mg of 3- chloroperbenzoic acid, and the mixture was stirred for 1 hour. Saturated aqueous sodium hydrogencarbonate was added, and the mixture was extracted with ethyl acetate. An organic layer was added, and the mixture was washed with saturated aqueous sodium chloride, dried over anhydrous sodium sulfate, filtered and concentrated, followed by silica gel chromatography to give 7.3 mg (yield 21%) of 2-methylsulfinyl-5-(1-hydroxy-6-methoxycarbonylhexyl)-4-(3-hydroxy-1-octenyl)-2-cyclopentenone.

Spectrum data
$^1$H-NMR CDCl$_3$ δ
0.88 (3H, brt, J=5.7 Hz), 1.1–2.4 (21H, m),
2.34 (3H, s), 3.1–3.5 (1H, m), 3.66 (3H, s),
3.7–4.1 (1H, m), 3.9–4.2 (1H, m), 5.2–5.9
(2H, m), 7.80 (1H, d, J=3 Hz).

EXAMPLE 22

Synthesis of
2-methylthio-5-(6-methoxycarbonylhexylidene)-4-(3-t-butyldimethylsilyloxy-1-octenyl)-2-cyclopentenone

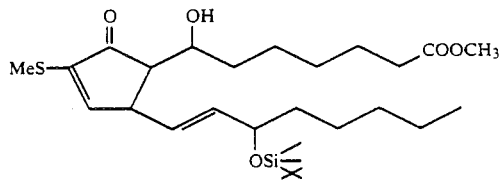

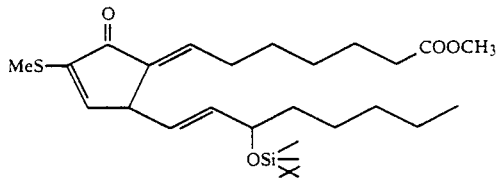

To a solution of 3.47 g of 2-methylthio-5-(1-hydroxy-6-methoxycarbonylhexyl)-4-(3-t-butyldimethylsilyloxy-1-octenyl)-2-cyclopentenone obtained in Example 6 in dichloromethane (30 ml) was added dimethylaminopyridine (1.54 g) and the mixture was cooled to 0° C. To the solution was dropwise added 0.59 ml of methanesulfonyl chloride, and the mixture was stirred at room temperature for 15 hours. To the reaction mixture were added ethyl acetate and an aqueous potassium hydrogensulfate, and the product was extracted into an organic layer. The extract was washed with saturated aqueous sodium hydrogencarbonate and saturated sodium chloride, dried over anhydrous magnesium sulfate, and filtered, followed by concentration. The concentrate was subjected to silica gel chromatography to give 2.15 g (yield 64%) of 2-methylthio-5-(6-methoxycarbonylhexylidene)-4-(3-t-butyldimethylsilyloxy-1-octenyl)-2-cyclopentenone.

Spectrum data
$^1$H-NMR CDCl$_3$ δ
0.00 (3H, s), 0.02 (3H, s), 0.87 (9H, s),
0.7–1.1 (3H, brt), 1.1–2.3 (18H, m), 2.33
(3H, s), 3.65 (3H, s), 3.9–4.1 (2H, m), 5.38
(1H, dd, J=7.5 Hz), 5.65 (1H, dd, J=15,
6 Hz, 6.5–6.8 (2H, m).

EXAMPLES 23–33

2-Substituted-2-cyclopentenones listed in Table 4 were obtained in the same manner as in Example 12.

TABLE 4

| Example No. | Starting compound | 2-Substituted-2-cyclopentanones | Yield (%) | NMR (δCDCl₃) |
|---|---|---|---|---|
| 23 | 2-ethylthio-5-(1-hydroxy-6-methoxycarbonylhexyl)-4-(3-t-butyldimethylsilyloxy-1-octenyl)-2-cyclopentenone | 2-ethylthio-5-(6-methoxycarbonylhexylidene)-4-(3-t-butyldimethylsilyloxy-1-octenyl)-2-cyclopentenone | 33 | 0.00(3H, s), 0.03(3H, s), 0.88(9H, s), 0.7-1.1(6H, m), 1.1-2.7(20H, m), 3.69(3H, s), 3.9-4.1(2H, m), 5.3-5.8(2H, m), 6.5-6.9(2H, m) |
| 24 | 2-methylthio-5-(1-hydroxy-6-methoxycarbonyl)-2-hexynyl)-4-(3-t-butyldimethylsilyloxy-3-cyclopentyl-1-propenyl)-2-cyclopentenone | 2-methylthio-5-(6-methoxycarbonyl-2-hexynylidene)-4-(3-t-butyldimethylsilyloxy-3-cyclopentyl-1-propenyl)-2-cyclopentenone | 23 | 0.01(3H, s), 0.03(3H, s), 0.89(9H, s), 1.1-2.0(11H, m), 2.0-3.0(4H, m), 2.34(3H, s), 3.68(3H, s), 3.8-4.1(2H, m), 5.3-5.8(2H, m), 6.5-6.9(2H, m) |
| 25 | 2-(5-methoxycarbonylpentylthio)-5-(1-hydroxy-6-methoxycarbonyl-2-hexynyl)-4-(3-t-butyldimethylsilyloxy-3-cyclopentyl-1-propenyl)-2-cyclopentenone | 2(5-methoxycarbonylpentylthio)-5-(6-methoxycarbonyl-2-hexynylidene)-4-(3-t-butyldimethylsilyloxy-3-cyclopentyl-1-propenyl)-2-cyclopentenone | 35 | 0.01-0.04(6H, m), 0.89(9H, s), 1.1-2.1(17H, m), 2.1-3.1(8H, s), 3.8-4.1(6H, s), 3.69, 5.3-5.8(2H, m), 6.5-6.9(2H, m) |

TABLE 4-continued

| Example No. | Starting compound | 2-Substituted-2-cyclopentanones | Yield (%) | NMR (δCDCl₃) |
|---|---|---|---|---|
| 26 |   2-(3-phenylpropylthio)-5-(1-hydroxy-6-methoxycarbonyl-2-hexynyl)-4-(3-t-butyldimethylsilyloxy-3-cyclopentyl-1-propenyl)-2-cyclopentenone | 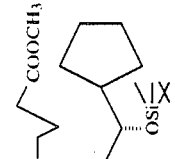  2-(3-phenylpropylthio)-5-(6-methoxycarbonyl-2-hexynylidene)-4-(3-t-butyldimethylsilyloxy-1-propenyl)-2-cyclopentenone | 29 | 0.04(6H, s), 0.90 (9H, s), 1.0-3.0 (2H, m), 3.69 (3H, s), 3.8-4.1 (2H, m), 5.3-5.8 (2H, m), 6.5-6.9 (2H, m), 7.0-7.4(5H, m) |
| 27 | 2-phenylthio-5-(1-hydroxy-6-methoxycarbonyl-2-hexynyl)-4-(3-t-butyldimethylsilyloxy-3-cyclopentyl-1-propenyl)-2-cyclopentenone | 2-phenylthio-5-(6-methoxycarbonyl-2-hexylidene)-4-(3-t-butyldimethylsilyloxy-3-cyclopentyl-1-propenyl)-2-cyclopentenone | 24 | 0.05(6H, s), 0.89 (9H, s), 1.1-2.1 (11H, m), 2.1-2.6 (4H, m), 3.68 (3H, s), 3.7-4.2 (2H, m), 5.4-5.9 (2H, m), 6.5-6.9 (2H, m), 7.0-7.7(5H, m) |
| 28 | 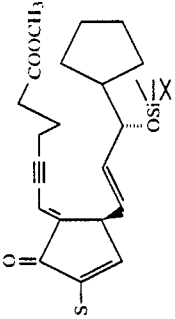  2-(6-methoxynaphthyl-2-thio)-5-(1-hydroxy-6-methoxycarbonyl-2-hexynyl)-4-(3-t-butyldimethylsilyloxy-3-cyclopentyl-1-propenyl)-2-cyclopentenone | 2-(6-methoxynaphthyl-2-thio)-5-(6-methoxycarbonyl-2-hexynylidene)-4-(3-t-butyldimethylsilyloxy-3-cyclopentyl-1-propenyl)-2-cyclopentenone | 21 | 0.08(6H, s), 0.89 (9H, s), 1.1-2.1 (11H, m), 2.1-2.6 (4H, m), 3.69(3H, s), 3.7-4.2(2H, m), 3.97 (3H, m), 5.4-5.8(2H, m), 6.5-6.9(2H, m), 7.0-8.1(6H, m) |

TABLE 4-continued

| Example No. | Starting compound | 2-Substituted-2-cyclopentanones | Yield (%) | NMR (δCDCl₃) |
|---|---|---|---|---|
| 29 | 2-methylthio-5-(1-hydroxy-6-methoxycarbonyl-5-hexenyl)-4-(3-t-butyldimethylsilyloxy-5-methyl-1-nonenyl)-2-cyclopentenone | 2-methylthio-5-(6-methoxycarbonyl-5-hexenylidene)-4-(3-t-butyldimethylsilyloxy-5-methyl-1-nonenyl)-2-cyclopentenone | 41 | 0.01–0.05(6H, m), 0.89(9H, s), 0.7–1.0 (6H, m), 1.0–1.9 (11H, m), 1.9–2.5 (4H, m), 2.35(3H, s), 3.70(3H, s), 3.8–4.4 (2H, m), 5.1–6.0 (3H, m), 6.5–7.3(3H, m) |
| 30 | 2-(4-chlorophenylmethylthio)-5-(1-hydroxy-6-methoxycarbonyl-5-hexenyl)-4-(3-t-butyldimethylsilyloxy-5-methyl-1-nonenyl)-2-cyclopentenone | 2-(4-chlorophenylmethylthio)-5-(6-methoxycarbonyl-5-hexenylidene)-4-(3-t-butyldimethylsilyloxy-5-methyl-1-nonenyl)-2-cyclopentenone | 39 | 0.01(3H, s), 0.04 (3H, s), 0.89 (9H, s), 0.7–1.0 (6H, m), 1.0–2.7 (15H, m), 3.68 (3H, s), 3.6–3.9 (4H, m), 5.3–6.1 (3H, m), 6.5–7.4(7H, m) |
| 31 | 2-ethylthio-5-(1-hydroxy-6-methoxycarbonylhexyl)-4-[3-(tetrahydropyran-2-yloxy)-3-cyclohexyl-1-propenyl]-2-cyclopentenone | 2-ethylthio-5-(6-methoxycarbonylhexylidene)-4-[3-(tetrahydropyran-2-yloxy)-3-cyclohexyl-1-propenyl]-2-cyclopentenone | 39 | 0.7–1.1(3H, m), 1.1–2.7(29H, m), 3.68(3H, s), 3.6–4.0 (3H, m), 4.5–5.1 (2H, m), 5.3–5.8 (2H, m), 6.5–7.0 (2H, m) |

TABLE 4-continued

| Example No. | Starting compound | 2-Substituted-2-cyclopentanones | Yield (%) | NMR (δCDCl₃) |
|---|---|---|---|---|
| 32 | 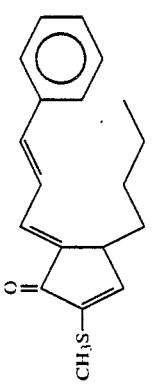<br>2-methylthio-5-(1-hydroxy-3-phenyl-2-propenyl)-4-butyl-2-cyclopentenone | 2-methylthio-5-(3-phenyl-2-propenylidene)-4-butyl-2-cyclopentenone | 63 | 0.7–1.0(3H, m), 1.1–1.9(6H, m), 2.33 (3H, s), 3.3–3.8 (1H, m), 6.0–7.7 (9H, m) |
| 33 | 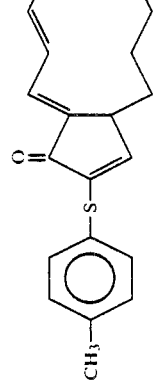<br>2-(4-methylphenylthio)-5-(1-hydroxy-3-phenyl-2-propenyl)-4-butyl-2-cyclopentenone | 2-(4-methylphenylthio)-5-(3-phenyl-2-propenylidene)-4-butyl-2-cyclopentenone | 57 | 0.7–1.0(3H, m), 1.1–1.9(6H, m), 2.30 (3H, s), 3.3–3.8 (1H, m), 6.0–7.9 (13H, m) |

EXAMPLE 34

Synthesis of 2-methylthio-5-(6-methoxycarbonylhexylidene)-4-(3-hydroxy-1-octenyl)-2-cyclopentenone

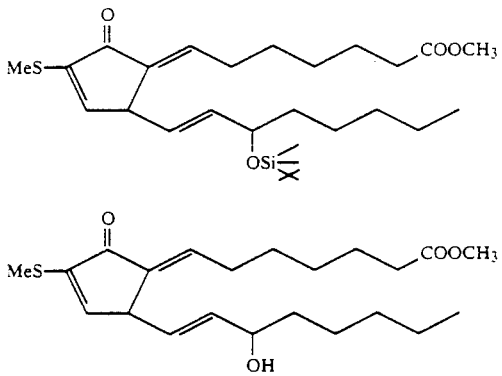

An amount of 1.42 g of 2-methylthio-5-(6-methoxycarbonylhexylidene-4-(3-t-butyldimethylsilyloxy-1-octenyl)-2-cyclopentenone obtained in Example 22 was added to a mixture of acetic acid (2.1 ml), tetrahydrofuran (1.4 ml) and water (0.7 ml), and the mixture was stirred at room temperature for 2 days. To the reaction mixture saturated aqueous sodium hydrogencarbonate and ethyl acetate were added, and the product was extracted into the organic layer. The extract was washed with saturated aqueous sodium chloride, then dried over anhydrous magnesium sulfate and filtered, followed by concentration. The concentrate was subjected to silica gel chromatography to give 0.93 g (yield 85%) of 2-methylthio-5-(6-methoxycarbonylhexylidene)-4-(3-hydroxy-1-octenyl)-2-cyclopentenone.

Spectrum data
$^1$H-NMR CDCl$_3$ δ
0.89 (3H, brt), 1.1–2.4 (19H, m), 2.35 (3H, s), 3.66 (3H, s), 3.9–4.2 (2H, m), 5.2–5.9 (2H, m), 6.6–6.8 (2H, m).

EXAMPLES 35–44

2-Substituted-2-cyclopentenones listed in Table 5 were obtained in the same manner as in Example 34.

TABLE 5

| Example No. | Starting compound | 2-Substituted-2-cyclopentanones | Yield (%) | NMR (δCDCl₃) |
|---|---|---|---|---|
| 36 | 2-ethylthio-5-(6-methoxycarbonylhexylidene)-4-(3-t-butyldimethylsilyloxy-1-octenyl)-2-cyclopentenone | 2-ethylthio-5-(6-methoxycarbonylhexylidene)-4-(3-hydroxy-1-octenyl)-2-cyclopentenone | 77 | 0.7–1.1(6H, m), 1.1–2.7(21H, m), 3.69(3H, s), 3.9–4.1 (2H, m), 5.3–5.8 (2H, m), 6.5–6.9 (2H, m) |
| 37 | 2-methylthio-5-(6-methoxycarbonyl-2-hexynylidene)-4-(3-t-butyldimethylsilyloxy-3-cyclopentyl-1-propenyl)-2-cyclopentenone | 2-methylthio-5-(6-methoxycarbonyl-2-hexynylidene)-4-(3-hydroxy-3-cyclopentyl-1-propenyl)-2-cyclopentenone | 62 | 1.1–2.0(11H, m), 2.0–3.0(5H, m), 2.35 (3H, s), 3.67 (3H, s), 3.8–4.1 (2H, m), 5.3–5.8 (2H, m), 6.5–6.9 (2H, m) |
| 38 | 2-(5-methoxycarbonylpentylthio)-5-(6-methoxycarbonyl-2-hexynylidene)-4-(3-t-butyldimethylsilyloxy-3-cyclopentyl-1-propenyl)-2-cyclopentenone | 2-(5-methoxycarbonylpentylthio)-5-(6-methoxycarbonyl-2-hexynylidene)-4-(3-hydroxy-3-cyclopentyl-1-propenyl)-2-cyclopentenone | 60 | 1.1–2.1(17H, m), 2.1–3.1(9H, m), 3.69 (6H, s), 3.8–4.1 (2H, m), 5.3–5.8 (2H, m), 6.5–6.9 (2H, m) |
| 39 | 2-(3-phenylpropylthio)-5-(6-methoxycarbonyl-2-hexynylidene)-4-(3-t-butyldimethylsilyloxy-3-cyclopentyl-1-propenyl)-2-cyclopentenone | 2-(3-phenylpropylthio)-5-(6-methoxycarbonyl-2-hexynylidene)-4-(3-hydroxy-3-cyclopentyl-1-propenyl)-2-cyclopentenone | 71 | 1.0–3.0(22H, m), 3.68(3H, s), 3.8–4.2 (2H, m), 5.3–5.8 (2H, m), 6.5–6.9 (2H, m), 7.0–7.4 (5H, m) |

TABLE 5-continued

| Example No. | Starting compound | 2-Substituted-2-cyclopentanones | Yield (%) | NMR (δCDCl₃) |
|---|---|---|---|---|
| 40 |  2-phenylthio-5-(6-methoxycarbonyl-2-hexynylidene)-4-(3-t-butyldimethylsilyloxy-3-cyclopentyl-1-propenyl)-2-cyclopentenone | 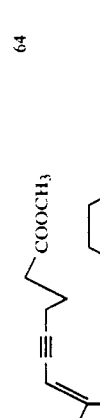 2-phenylthio-5-(6-methoxycarbonyl-2-hexynylidene)-4-(3-hydroxy-3-cyclopentyl-1-propenyl)-2-cyclopentenone | 58 | 1.1–2.1(11H, m), 2.1–2.9(5H, m), 3.68 (3H, s), 3.7–4.2 (2H, m), 5.4–5.9 (2H, m), 6.5–6.9 7.0–7.7 (5H, m) |
| 41 |  2-(6-methoxynaphthyl-2-thio)-5-(6-methoxycarbonyl-2-hexynylidene)-4-(3-t-butyldimethylsilyloxy-3-cyclopentyl-1-propenyl)-2-cyclopentenone |  2-(6-methoxynaphthyl-2-thio)-5-(6-methoxycarbonyl-2-hexynylidene)-4-(3-hydroxy-3-cyclopentyl-1-propenyl)-2-cyclopentenone | 64 | 1.1–2.1(11H, m), 2.1–2.8(5H, m), 3.69 (3H, s), 3.7–4.2 (2H, m), 3.98 (3H, s), 5.4–5.8 (2H, m), 6.5–6.9 (2H, m), 7.0–8.1 (6H, m) |
| 42 | 2-methylthio-5-(6-methoxycarbonyl-5-hexenylidene)-4-(3-t-butyldimethylsilyloxy-5-methyl-1-nonenyl)-2-cyclopentenone | 2-methylthio-5-(6-methoxycarbonyl-5-hexenylidene)-4-(3-hydroxy-5-methyl-1-nonenyl)-2-cyclopentenone | 69 | 0.7–1.0(6H, m), 1.0–1.9(11H, m), 1.9 2.8(5H, m), 2.33 (3H, s), 3.68 (3H, s), 3.8–4.4 (2H, m), 5.1–6.0 (3H, m), 6.5–7.3 (3H, m) |
| 43 | 2-(4-chlorophenylmethylthio)-5-(6-methoxycarbonyl-5-hexenylidene)-4-(3-t-butyldimethylsilyloxy-5-methyl-1-nonenyl)-2-cyclopentenone | 2-(4-chlorophenylmethylthio)-5-(6-methoxycarbonyl-5-hexenylidene)-4-(3-hydroxy-5-methyl-1-nonenyl)-2-cyclopentenone | 43 | 0.7–1.0(6H, m), 1.0–2.9(16H, m), 3.68(3H, s), 3.6–3.9 (4H, m), 5.3 6.1 (3H, m), 6.5 7.4 (7H, m) |

TABLE 5-continued

| Example No. | Starting compound | 2-Substituted-2-cyclopentanones | Yield (%) | NMR (δCDCl₃) |
|---|---|---|---|---|
| 44 | 2-ethylthio-5-(6-methoxycarbonylhexylidene)-4-[3-(tetrahydropyran-2-yloxy)-3-cyclohexyl-1-propenyl]-2-cyclopentenone | 2-ethylthio-5-(6-methoxycarbonylhexylidene)-4-(3-hydroxy)-3-cyclohexyl-1-propenyl]-2-cyclopentenone | 61 | 0.7-1.1(3H, m), 1.1-2.9(24H, m), 3.68(3H, s), 3.8-4.3 (2H, m), 5.3-5.9 (2H, m), 6.5-7.0 (2H, m) |

EXAMPLE 45

Synthesis of
2-methylthio-5-(6-carboxyhexylidene)-4-(3-hydroxyl-octenyl)-2-cyclopentenone

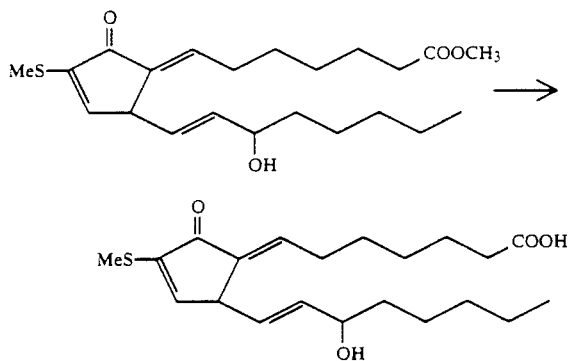

To a solution of 345 mg of 2-methylthio-5-(6-methoxycarbonylhexylidene)-4-(3-hydroxy-1-octenyl)-2-cyclopentenone obtained in Example 34 dissolved in 20 ml of acetone was added 220 ml of 0.1M phosphate buffer of pH 8. While the mixture was stirred, 24 mg of pig liver esterase was added thereto, and the mixture was stirred at 30–35° C. for 150 hours. After the pH was adjusted to 4 with 0.1N hydrochloric acid, ammonium sulfate was added to saturation and ethyl acetate was added, followed by filtration. The filtrate was extracted with ethyl acetate, and the organic layers were combined and washed with saturated aqueous sodium chloride. The product was dried over anhydrous magnesium sulfate, filtered and concentrated, followed by silica gel chromatography to give 193 mg (yield 58%) of 2-methylthio-5-(6-carboxyhexylidene)-4-(3-hydroxy-1-octenyl)-2-cyclopentenone.

Spectrum data
$^1$H-NMR CDCl$_3$ δ
0.86 (3H, brt, J=5.6 Hz), 1.1–2.5 (20H, m),
2.34 (3H, s), 3.9–4.2 (2H, m), 5.2–5.9
(2H, m), 6.6–6.8 (2H, m).

EXAMPLE 46

Synthesis of
2-methylsulfinyl-5-(6-methoxycarbonylhexylidene)-4-(3-hydroxy-1-octenyl)-2-cyclopentenone

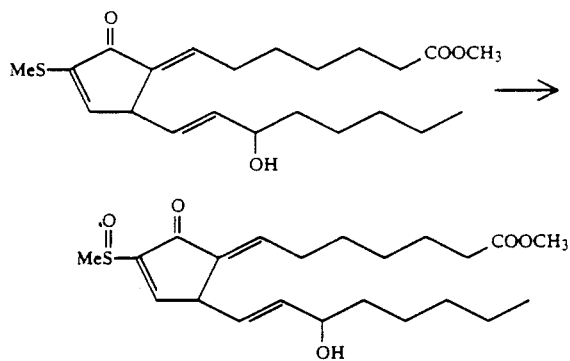

A solution of 252.2 mg of 2-methylthio-5-(6-methoxycarbonylhexylidene)-4-(3-hydroxy-1-octenyl)-2-cyclopentenone obtained in Example 34 in dichloromethane (20 ml) was cooled to 0° C., and a solution of 3-chloroperbenzoic acid (129.8 mg) in dichloromethane (10 ml) was added dropwise thereto. After the mixture was stirred at 0° C. for 1 hour, ethyl acetate and saturated aqueous sodium hydrogencarbonate was added, and the product was extracted into the organic layer. The extract was successively washed with saturated aqueous sodium chloride, saturated aqueous ammonium chloride and saturated aqueous sodium chloride, then dried over anhydrous magnesium sulfate, and filtered, followed by concentration. The concentrate was subjected to silica gel chromatography to give 186.8 mg (yield 71%) of a mixture of isomers of 2-methylsulfinyl-5-(6-methoxycarbonylhexylidene)-4-(3-hydroxy-1-octenyl)-2-cyclopentenone.

Spectrum data
$^1$H-NMR CDCl$_3$ δ
0.89 (3H, brt), 1.1–2.4 (19H, m), 2.86 and
2.88 (3H, s), 3.67 (3H, s), 4.0–4.3 (2H, m),
5.3–6.0 (2H, m), 6.72 (1H, t, J=7 Hz),
7.7–7.8 (1H, m).

EXAMPLE 47

Synthesis of
2-methylsulfinyl-5-(6-methoxycarbonylhexylidene)-4-(3-hydroxy-1-octenyl)-2-cyclopentenone

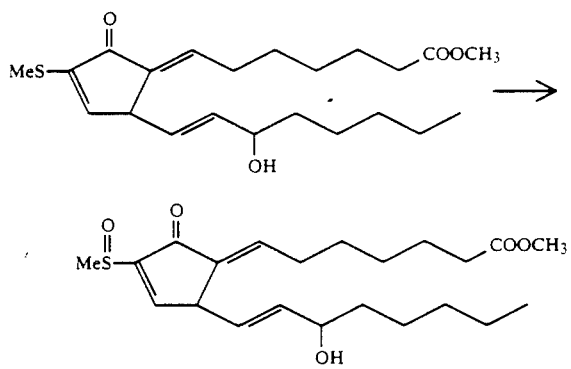

To a solution of 21.9 mg of 2-methylthio-5-(6-methoxycarbonylhexylidene)-4-(3-hydroxy-1-octenyl)-2-cyclopentenone obtained in Example 34 in methanol (3 ml) was added a solution of sodium metaperiodide (118.7 mg) in water (0.5 ml), and the mixture was stirred for 18 hours. To the reaction mixture were added ethyl acetate and saturated aqueous sodium chloride, and the product was extracted into the organic layer. The extract was washed with saturated aqueous sodium chloride, dried over anhydrous magnesium sulfate and filtered, followed by concentration. The concentrate was subjected to silica gel chromatography to give 9.6 mg (yield 42%) of 2-methylsulfinyl-5-(6-methoxycarbonylhexylidene)-4-(3-hydroxy-1-octenyl)-2-cyclopentenone.

EXAMPLE 48

Synthesis of
2-methylsulfinyl-5-(6-methoxycarbonylhexylidene)-4-(3-hydroxy-1-octenyl)-2-cyclopentenone

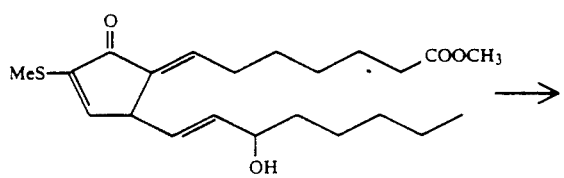

-continued

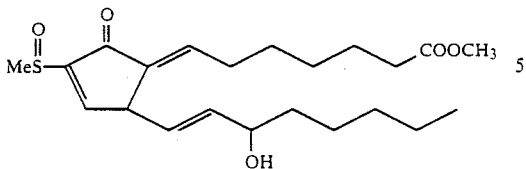

To a solution of 17.6 mg of 2-methylthio-5-(6-methoxycarbonylhexylidene)-4-(3-hydroxy-1-octenyl)-2-cyclopentenone obtained in Example 34 in methanol (0.5 ml) was added a solution of 2KHSO$_5$·KHSO$_4$·K$_2$SO$_4$ (27.4 mg) in water (0.2 ml) at 0° C., and the mixture was stirred for 30 minutes. To the reaction mixture were added ethyl acetate and saturated aqueous sodium hydrogencarbonate, and the product was extracted into the organic layer. The extract was washed with saturated aqueous sodium chloride, dried over anhydrous magnesium sulfate and filtered, followed by concentration. The concentrate was subjected to silica gel chromatography to obtain 3 mg (yield 16%) of 2-methylsulfinyl-5-(6-methoxycarbonylhexylidene)-4-(3-hydroxy-1-octenyl)-2-cyclopentenone.

EXAMPLE 49

Synthesis of 2-methylsulfonyl-5-(6-methoxycarbonylhexylidene)-4-(3-hydroxy-1-octenyl)-2-cyclopentenone

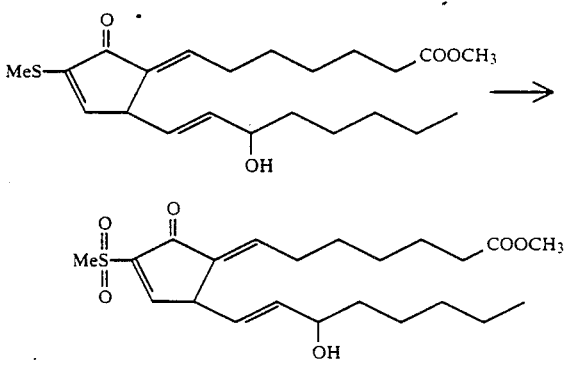

A solution of 18 mg of 2-methylthio-5-(6-methoxycarbonylhexylidene)-4-(3-hydroxy-1-octenyl)-2-cyclopentenone obtained in Example 34 in dichloromethane (1.5 ml) was cooled to 0° C., and a solution of 3-chloroperbenzoic acid (15.7 mg) in dichloromethane (1 ml) was added dropwise thereto. After the mixture was stirred at 0° C. for 2 hours, ethyl acetate and saturated aqueous sodium hydrogencarbonate were added and the product was extracted into the organic layer. The extract was successively washed with saturated aqueous sodium chloride, saturated aqueous ammonium chloride and saturated aqueous sodium chloride, then dried over anhydrous magnesium sulfate and filtered, followed by concentration. The concentrate was subjected to silica gel chromatography to give 16.6 mg (yield 85%) of 2-methylsulfonyl-5-(6-methoxycarbonylhexylidene)-4-(3-hydroxy-1-octenyl)-2-cyclopentenone.

Spectrum data
$^1$H-NMR CDCl$_3$ δ
0.7–1.0 (m 3H), 1.1–2.4 (m, 18H), 3.16 (s, 3H), 3.66 (s, 3H), 4.0–4.5 (m, 2H), 5.3–6.0 (m, 2H), 6.82 (t, J=7 Hz, 1H), 8.06 (d, J=3 Hz, 1H).

EXAMPLE 50

Synthesis of 5-(6-methoxycarbonylhexylidene)-2-methylsulfinyl-4-(1-octenyl)-2-cyclopentenone

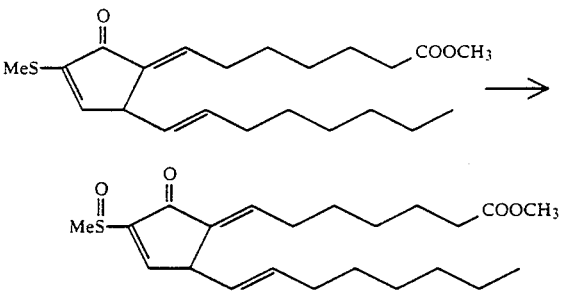

A solution of 9 mg of 5-(6-methoxycarbonylhexylidene-2-methylthio-4-(1-octenyl)-2-cyclopentenone obtained in Example 19 dissolved in 2 ml of methanol, and 500 μl of an aqueous solution of 150 mg of sodium periodate was added, and the mixture was stirred for 5 hours. Saturated aqueous sodium chloride was added, and the mixture was extracted with ethyl acetate. The organic layer was washed with saturated aqueous sodium chloride and dried over anhydrous magnesium sulfate. After filtration and concentration, the concentrate was subjected to silica gel column chromatography to give 4.3 mg (yield 48%) of a mixture of isomers of 5-(6-methoxycarbonylhexylidene)-2-methylsulfinyl-4-(1-octenyl)-2-cyclopentenone.

Spectrum data
$^1$H-NMR (CDCl$_3$) δ
0.88 (3H, brt, J=6.0 Hz), 1.0–2.5 (20H, m),
2.86 and 2.88 (3H, s), 3.67 (3H, s), 3.9–4.3 (1H, m), 5.0–6.0 (2H, m), 6.6–6.9 (1H, m), 7.80 (1H, d, J=3 Hz)

EXAMPLE 51

Syntheses of 2,3-epoxy-4-trimethylsilyloxy-4-(4-phenoxybutyl)cyclopentanone and 2,3-epoxy-4-hydroxy-4-(4-phenoxybutyl)cyclopentanone

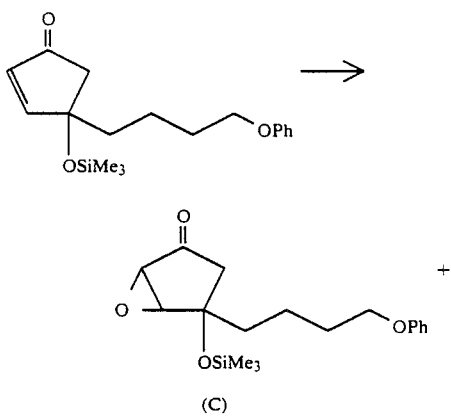

(C)

-continued

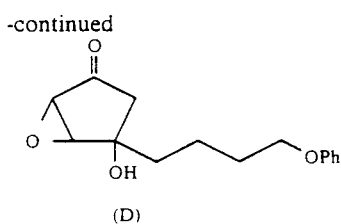
(D)

To a solution of 2.49 g of 4-trimethylsilyloxy-4-(4-phenoxybutyl)-2-cyclopentenone dissolved in 50 ml of methanol was added 3.9 ml of an aqueous 30% hydrogen peroxide under ice-cooling and stirring. An amount of 390 µl of 1N aqueous sodium hydroxide was added, and the mixture was stirred for 2 hours. Then saturated aqueous ammonium chloride was added, and the mixture was extracted with ethyl acetate. The organic layer was washed with saturated aqueous sodium chloride and dried over anhydrous magnesium sulfate. After filtration and concentration, the concentrate was subjected to silica gel column chromatography to give 892 mg (yield 34%) of 2,3-epoxy-4-trimethylsilyloxy-4-(4-phenoxybutyl)cyclopentanone and 1.38 g (yield 53%) of 2,3-epoxy-4-hydroxy-4-(4-phenoxybutyl)cyclopentanone.

Spectrum data
(C) $^1$H-NMR (CDCl$_3$) δ
0.20 (9H, s), 1.4–2.1 (6H, m), 2.16 (1H, d, J=17.5 Hz), 2.57 (1H, d, J=17.5 Hz), 3.45 (1H, d, J=2.5 Hz), 3.77 (1H, d, J=2.5 Hz), 3.8–4.1 (2H, m), 6.8–7.1 (3H, m), 7.15–7.45 (2H, m).

(D) $^1$H-NMR (CDCl$_3$) δ
1.4–2.1 (6H, m), 2.31 (1H, d, J=16.3 Hz), 2.4 (1H, d, 16.3 Hz), 2.4–2.8 (1H, m), 3.35–3.6 (1H, m), 3.65–4.2 (3H, m), 6.7–7.05 (3H, m), 7.1–7.45 (2H, m).

EXAMPLE 52

Synthesis of 2-methylthio-4-hydroxy-4-(4-phenoxybutyl)-2-cyclopentenone

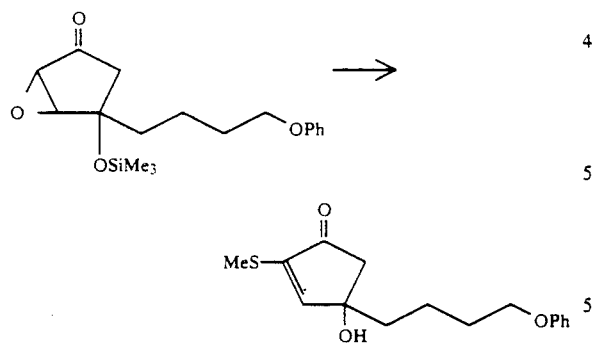

To a solution of 25 mg of sodium thiomethoxide dissolved in methanol, 51 µl of acetic acid was added, and the mixture was stirred for 10 minutes. Triethylamine (170 µl) was then added, and after the mixture was stirred for 10 minutes, a solution of 16 mg of 2,3-epoxy-4-trimethylsilyloxy-4-(4-phenoxybutyl)cyclopentanone obtained in Example 51 in 3 ml of methanol was added and the mixture was stirred for 5 hours. Then saturated aqueous ammonium chloride was added, and the mixture was extracted with ethyl acetate. The organic layer was washed with saturated aqueous sodium chloride and dried over anhydrous sodium sulfate. After filtration and concentration, the concentrate was subjected to silica gel column chromatography to obtain 7.1 mg (yield 51%) of 2-methylthio-4-hydroxy-4-(4-phenoxybutyl)-2-cyclopentenone.

Spectrum data
$^1$H-NMR (CDCl$_3$) δ
1.4–2.0 (6H, m), 2.18 (1H, s), 2.34 (3H, s), 2.63 (1H, d, J=17.5 Hz), 2.72 (1H, d, J=17.5 Hz), 4.0 (2H, brt, J=6.0 Hz), 6.76 (1H, s), 6.8–7.1 (3H, m), 7.15–7.45 (2H, m).

EXAMPLE 53

Synthesis of 2-methylthio-4-hydroxy-4-(4-phenoxybutyl)-2-cyclopentenone

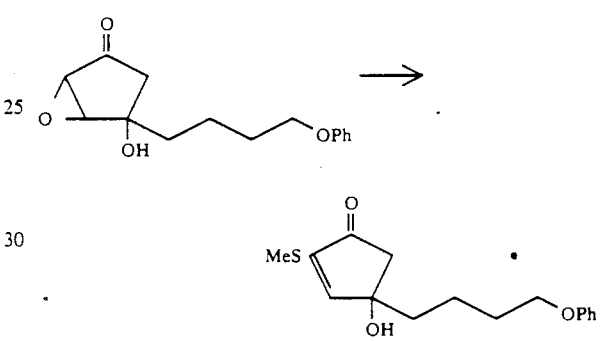

To a solution of 1.5 g of sodium thiomethoxide dissolved in 80 ml of methanol was added 1.8 ml of acetic acid under ice-cooling and stirring. After the mixture was stirred for 5 minutes, 4.8 ml of triethylamine was added, and the solution of 1.38 g of 2,3-epoxy-4-hydroxy-4-(4-phenoxybutyl)cyclopentánone obtained in Example 51 dissolved in 20 ml of methanol was added. After the mixture was stirred for 4 hours, water was added and the mixture was extracted with ethyl acetate. The organic layers were combined, washed with saturated aqueous sodium chloride and dried over anhydrous magnesium sulfate. After filtration and concentration, the concentrate was subjected to silica gel column chromatography to give 1.39 g (yield 83%) of 2-methylthio-4-hydroxy-4-(4-phenoxybutyl)-2-cyclopentenone.

EXAMPLE 54

Synthesis of 2-methylthio-4-(4-phenoxybutyl)-4-trimethylsilyloxy-2-cyclopentenone

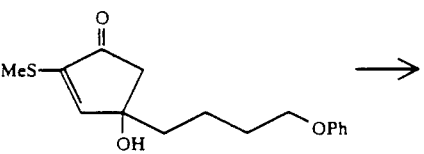

-continued

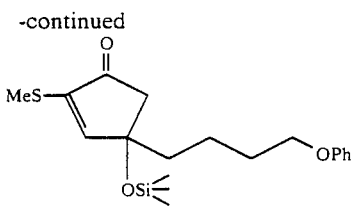

To a solution of 400 mg of 2-methylthio-4-hydroxy-4-(4-phenoxybutyl)-2-cyclopentenone obtained in Example 52 or Example 53 dissolved in 4 ml of dimethylformamide were added 279 mg of imidazole and 260 μl of chlorotrimethylsilane, under ice-cooling and stirring, and the mixture was stirred at 0° C. for 3 hours. The reaction mixture was extracted with an addition of water and hexane. The organic layer was washed with saturated aqueous sodium chloride, and the product dried over anhydrous sodium sulfate, filtered and concentrated, followed by silica gel column chromatography, to give 445 mg (yield 89%) of 2-methylthio-4-(4-phenoxybutyl)-4-trimethylsilyloxy-2-cyclopentenone.

Spectrum data
$^1$H-NMR (CDCl$_3$) δ
0.11 (9H, s), 1.3–1.9 (6H, m), 2.35 (3H, s),
2.66 (2H, s), 3.95 (2H, t, J=5.9 Hz), 6.80
(1H, s), 6.8–7.45 (5H, m).

EXAMPLE 55

Synthesis of 2-methylthio-4-octyl-4-trimethylsilyloxy-2-cyclopentenone

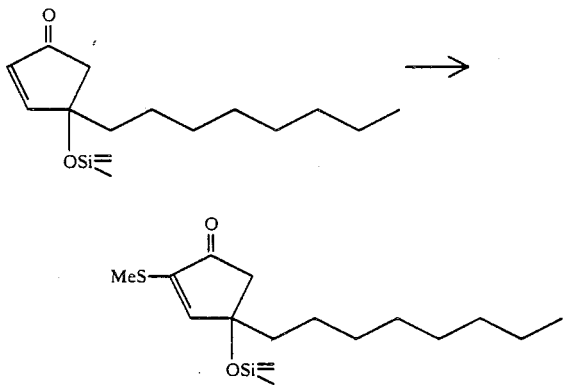

To a solution of 3.3 g of 4-octyl-4-trimethylsilyloxy-2-cyclopentenone dissolved in 50 ml of methanol was added, under ice-cooling and stirring, 5.0 ml of an aqueous 30% hydrogen peroxide, and 500 μl of an aqueous 1N sodium hydroxide was added. After the mixture was stirred for 3.5 hours, saturated aqueous ammonium chloride was added, and the mixture was extracted with ethyl acetate The organic layer was washed with saturated aqueous sodium chloride and dried over anhydrous magnesium sulfate. The product was filtered and concentrated to give a crude oil of 2,3-epoxy-4-octyl-4-trimethylsilyloxycyclopentanone.

A solution of 910 mg of sodium thiomethoxide dissolved in 100 ml of methanol was stirred under ice-cooling and stirring for 15 minutes. Triethylamine (6 ml) was added, and after the mixture was stirred for 10 minutes, a solution of the above crude oil of 2,3-epoxy-4-octyl-4-trimethylsilyloxycyclopentanone in 15 ml of methanol was added dropwise. After the mixture was stirred for 6 hours, the reaction mixture was poured onto saturated aqueous ammonium chloride, and the mixture was extracted with ethyl acetate. The organic layer was washed with saturated aqueous sodium chloride, dried over anhydrous sodium sulfate, filtered and concentrated to give a crude oil of 2-methylthio-4-hydroxy-4-octyl-2-cyclopentenone.

To a solution of the crude oil dissolved in 80 ml of dimethylformamide was added 2.2 g of imidazole, under ice-cooling and stirring, and then 2.0 g of chlorotrimethylsilane was added, followed by stirring at 0° C. for 4.5 hours. The mixture was extracted with addition of water and hexane, and the organic layer was washed with saturated aqueous sodium chloride. After drying over anhydrous sodium sulfate, filtration and concentration, the concentrate was subjected to silica gel column chromatography to give 1.41 g (yield 37%) of 2-methylthio-4-octyl-4-trimethylsilyloxy-2-cyclopentenone.

Spectrum data
$^1$H-NMR CDCl$_3$ δ
0.06 (9H, s), 0.89 (3H, brt), 1.1–1.9
(14H, m), 2.34 (3H, s), 2.64 (2H, s), 6.85
(1H, s).

EXAMPLES 56–60

2-Substituted-2-cyclopentenones listed in Table 6 were obtained in the same manner a in Example 55.

TABLE 6

| Example No. | Starting compound | 2-Substituted-2-cyclopentanones | Yield (%) | NMR (δCDCl$_3$) |
|---|---|---|---|---|
| 56 | 4-[3-(3,4-dimethoxy-phenyl)propyl]-4-hydroxy-2-cyclopentenone | 2-methylthio-4-[3-(3,4-dimethoxyphenyl)propyl]-4-trimethylsilyloxy-2-cyclo-pentenone | 41 | 0.09(9H, s), 1.4–1.9 (4H, m), 2.3–2.9 (4H, m), 2.35 (3H, s), 3.82 (6H, s), 6.6–7.1 (4H, m) |

TABLE 6-continued

| Example No. | Starting compound | 2-Substituted-2-cyclopentanones | Yield (%) | NMR (δCDCl₃) |
|---|---|---|---|---|
| 57 | 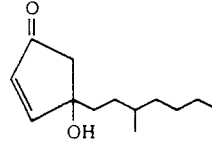 4-(3,7-dimethyloctyl)-4-hydroxy-2-cyclopentenone | 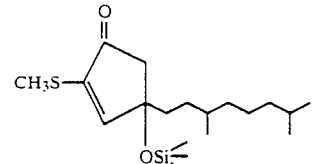 2-methylthio-4-(3,7-dimethyl-octyl-4-trimethylsilyloxy-2-cyclopentenone | 37 | 0.08(9H, s), 0.83 (9H, d, J=4.4 Hz), 0.9–2.1(12H, m), 2.34(3H, s), 2.65 (2H, s), 6.87(1H, s) |
| 58 | 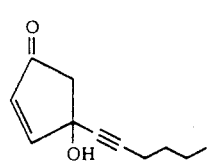 4-(1-hexynyl)-4-hydroxy-2-cyclopentenone | 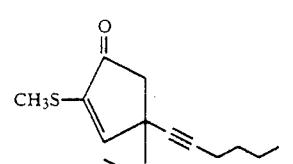 2-methylthio-4-(1-hexynyl)-4-trimethylsilyloxy-2-cyclopentenone | 33 | 0.05(9H, s), 0.7–1.1 (3H, m), 1.1–2.0 (6H, m), 2.34 (3H, s), 2.66 (2H, s), 6.83 (1H, s) |
| 59 | 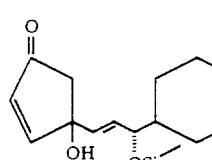 4-(3-t-butyldimethylsilyloxy-3-cyclohexyl-1-propenyl)-4-hydroxy-2-cyclopentenone | 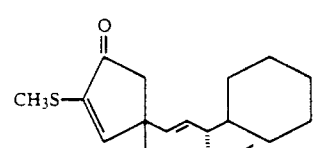 2-methylthio-4-(3-t-butyldimethylsilyloxy-3-cyclohexyl-1-propenyl)-4-trimethylsilyloxy-2-cyclopentenone | 26 | 0.01–0.08(15H, m), 0.89(9H, s), 1.0–2.0 (11H, m), 2.36 (3H, s), 2.68 (2H, s), 4.6–4.85 (1H, m), 5.4–5.8 (2H, m), 6.85(1H, s) |
| 60 | 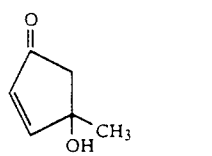 4-methyl-4-hydroxy-2-cyclopentenone | 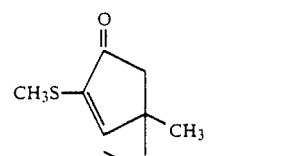 2-methylthio-4-methyl-4-trimethylsilyloxy-2-cyclopentenone | 56 | 0.07(9H, s), 0.85 (3H, s), 2.35 (3H, s), 2.68 (2H, s), 6.84(1H, s) |

EXAMPLE 61

Synthesis of 2-phenylthio-4-trimethylsilyloxy-4-(4-phenoxylbutyl)-2-cyclopentenone

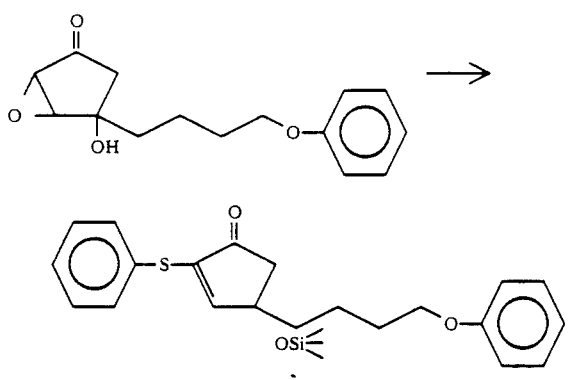

A 1.8 g amount of 2,3-epoxy-4-hydroxy-4-(4-phenoxybutyl)cyclopentanone obtained in Example 51 was dissolved in 15 ml of methanol, followed by adding 1.0 ml of triethylamine. Then, 790 mg of thiophenol was added, followed by stirring for 1.5 hours. The reaction mixture was poured on an aqueous saturated potassium hydrogensulfate solution, followed by extracting with ethyl acetate. The organic layer was washed with a saturated aqueous sodium chloride solution, followed by drying on anhydrous magnesium sulfate. After filtering and concentrating, the resultant crude oily product of 2-phenylthio-4-hydroxy-4-(4-phenoxybutyl)-2-cyclopentenone was dissolved in 20 ml of dimethylformamide and, while water cooling with stirring 1.5 g of imidazole was added. Thereafter, 1.4 g of chlorotrimethyl silane was added. The mixture was stirred at 0° C. for 5 hours, water and hexane was added to extract. The organic layer was washed with a saturated aqueous sodium chloride solution, dried over anhydrous sodium sulfate, and, after filtering and concentrating, the concentrate was subjected to silica gel column chromatography. Thus, 0.89 g (yield 37%) of 2-phenylthio-4-timethylsilyloxy-4-(4-phenoxylbutyl)-2-cyclopentenone was obtained.

Spectrum data
¹H-NMR CDCl₃ δ

0.05 (9H, S), 1.1-1.9 (6H, m), 2.63 (2H, S), 3.95 (2H, t, J=6.0 Hz), 6.8-7.7 (11H, m)

EXAMPLE 62

Synthesis of 5-[4,7-bis(t-butyldimethylsilyloxy)-1-hydroxy-2-heptenyl]-2-methylthio-4-(4-phenoxybutyl)-4-trimethylsilyloxy-2-cyclopentenone

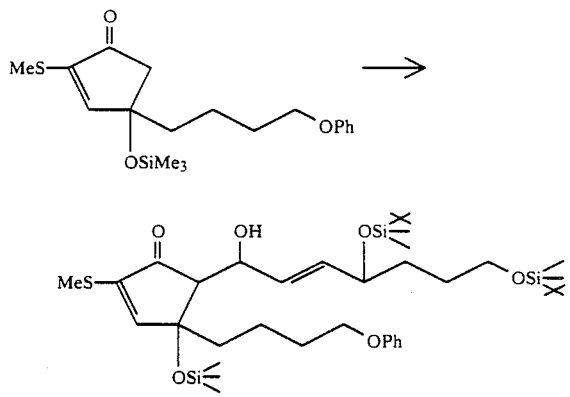

An amount of 1.195 g of 2-methylthio-4-(phenoxybutyl)-4-trimethylsilyloxy-2-cyclopentenone obtained in Example 54 was taken up, and after nitrogen replacement, 7.0 ml of dry ether and 7.0 ml of dry hexane was added. After 857 μl of diisopropylethylamine was added, the mixture was cooled to −70° C. A 1.0M dibutylborontrifrate dichloromethane solution (4.57 ml) was added, and the mixture was stirred at −70° C. for 1 hour. A solution of 1.47 g of 4,7-bis(t-butyldimethylsilyloxy)-2-heptenal in 10 ml of dry ether was cooled and added, followed by stirring at −70° C. for 3 hours. Saturated aqueous ammonium chloride was added, and the mixture was extracted with ether. The organic layers were combined, washed with saturated aqueous sodium chloride and dried over anhydrous magnesium sulfate. After filtration and concentration, the concentrate was subjected to silica gel column chromatography to give 1.81 g (yield 75%) of a mixture of isomers of 5-[4,7-bis(t-butyldimethylsilyloxy)-1-hydroxy-2-heptenyl]-2-methylthio-4-(4-phenoxybutyl)-4-trimethylsilyloxy-2-cyclopentenone.

Spectrum data
Less polar isomer
$^1$H-NMR CDCl$_3$ δ
0–0.2 (m, 21H), 0.90 (s, 18H), 1.0–2.1 (m, 10H), 2.34 (s, 3H), 2.74 (d, 1H, J=7.0 Hz), 3.5–3.7 (m, 2H), 3.98 (t, 2H, J=5.4 Hz), 4.05–4.35 (m, 1H), 4.35–4.7 (m, 1H), 5.5–6.2 (m, 2H), 6.7–7.1 (m, 4H), 7.1–7.5 (m, 2H).

More polar isomer
$^1$H-NMR CDCl$_3$ δ
0–0.2 (m, 21H), 0.90 (s, 18H), 1.1–2.1 (m, 10H), 2.34 (s, 3H), 2.77 (d, 1H, J=6.3 Hz), 3.45–3.7 (m, 2H), 3.97 (t, 2H, J=5.3 Hz), 4.05–4.3 (m, 1H), 4.4–4.8 (m, 1H), 5.5–6.2 (m, 2H), 6.7–7.1 (m, 4H), 7.1–7.5 (m, 2H).

EXAMPLES 63–71

2-Substituted-2-cyclopentenones listed in Table 7 were obtained in the same manner as in Example 62.

TABLE 7

| Example No. | Starting compound — 2-Substituted-2-cyclopentenones | Aldehydes | 2-Substituted-2-cyclopentenones | Yield (%) | NMR (δCDCl$_3$) |
|---|---|---|---|---|---|
| 63 | 2-methylthio-4-(4-phenoxybutyl)-4-trimethylsilyloxy-2-cyclopentenone | 3-(4-methoxycarbonylcyclohexyl)propanal | 2-methylthio-5-[1-hydroxy-3-(4-methoxycarbonylcyclohexyl)propyl]-4-(4-phenoxybutyl)-4-trimethylsilyl-2-cyclopentenone | 65 | 0.07(9H, s), 1.1–2.8(22H, m), 2.35(3H, s), 3.67(3H, s), 3.8–4.3 (3H, m), 6.7–7.5 (6H, m) |
| 64 | | 4-(4-methoxyphenyl)butanal | 2-methylthio-5-[1-hydroxy-4-(4-methoxyphenyl)butyl]-4-(4-phenoxybutyl)-4-trimethylsilyloxy-2-cyclopentenone | 47 | 0.06(9H, s), 1.1–2.9(14H, m), 2.35(3H, s), 3.75(3H, s), 3.7–4.3 (3H, m), 6.6–7.5 (10H, m) |

TABLE 7-continued

| Example No. | Starting compound 2-Substituted-2-cyclopentenones | Aldehydes | 2-Substituted-2-cyclopentenones | Yield (%) | NMR (δCDCl₃) |
|---|---|---|---|---|---|
| 65 | 2-phenylthio-4-(4-phenoxybutyl)-4-trimethylsilyloxy 2-cyclopentenone | Octanal | 2-phenylthio-5-(1-hydroxyoctyl)-4-(4-phenoxybutyl)-4-trimethylsilyloxy-2-cyclopentenone | 55 | 0.07(9H, s), 0.7–1.0(3H, brt), 1.0–2.0 (18H, m), 2.5–2.9(2H, m), 3.7–4.0 (1H, m), 4.0 (2H, brt, J=6.0Hz), 6.7–7.5 (11H, m) |
| 66 | 2-methylthio-4-[3-(3,4-dimethoxyphenyl)propyl]-4-trimethylsilyloxy-2-cyclopentenone | methyl 7-oxoheptanoate | 2-methylthio-5-(1-hydroxy-6-methoxycarbonylhexyl)-4-[3-(3,4-dimethoxyphenyl)propyl]-4-trimethylsilyloxy-2-cyclopentenone | 37 | 0.17(9H, s), 1.0–2.1(12H, m), 2.1–2.8 (6H, m), 2.35 (3H, s), 3.65 (3H, s), 3.7–4.3(1H, m), 3.86(6H, s), 6.6–7.1 (4H, m) |
| 67 | 2-methylthio-4-(3,7-dimethyloctyl)-4-trimethylsilyloxy-2-cyclopentenone | methyl 7-oxoheptanoate | 2-methylthio-5-(1-hydroxy-6-methylcarbonylhexyl)-4-(3,7-dimethyloctyl)-4-trimethylsilyloxy-2-cyclopentenone | 48 | 0.08(9H, s), 0.83(9H, d, J=4.5Hz), 0.9–2.9(24H, m), 2.35(3H, s), 3.68(3H, s), 3.71–4.1 (1H, m), 6.86 (1H, s) |
| 68 | 2-methylthio-4-(1-hexynyl)-4-trimethylsilyloxy-2-cyclopentenone | methyl 7-oxoheptanoate | 2-methylthio-5-(1-hydroxy-6-methoxycarbonylhexyl)-4-(1-hexynyl)-4-trimethylsilyloxy-2-cyclopentenone | 42 | 0.05(9H, s), 0.7–1.0(3H, brt), 1.0–2.9 (18H, m), 2.36(3H, s), 3.69(3H, s), 3.7–4.0(1H, m), 6.87 (1H, s) |
| 69 | 2-methylthio-4-(3-t-butyldimethylsilyloxy-3-cyclohexyl-1-propenyl)-4-trimethylsilyloxy-2-cyclopentenone | methyl 7-oxo-5-heptynoate | 2-methylthio-5-(1-hydroxy-6-methoxycarbonyl-2-hexynyl)-4-(3-t-butyldimethylsilyloxy-3-cyclohexyl-1-propenyl)-4-trimethylsilyloxy-2-cyclopentenone | 38 | 0.01–0.09 (15H, m), 0.89(9H, s), 1.0–2.9(19H, m), 2.36(3H, s), 3.68 (3H, s), 3.8–4.0 (1H, m), 4.6–4.8(1H, m), 5.3–5.9 (2H, m), 6.89 (1H, s) |
| 70 | 2-methylthio-4-methyl-4-trimethylsilyloxy-2-cyclopentenone | methyl 7-oxoheptanoate | 2-methylthio-5-(1-hydroxy-6-methoxycarbonylhexyl)-4-methyl-4-trimethylsilyloxy-2-cyclopentenone | 51 | 0.06(9H, s), 1.25(3H, s), 1.1–2.8(12H, m), 2.36(3H, s), 3.68(3H, s), 3.7–4.0 (1H, m), 6.87 (1H, s) |

TABLE 7-continued

| Example No. | Starting compound 2-Substituted-2-cyclopentenones | Aldehydes | 2-Substituted-2-cyclopentenones | Yield (%) | NMR (δCDCl₃) |
|---|---|---|---|---|---|
| 71 | ![structure] 2-methylthio-4-octyl-4-trimethylsilyloxy-2-cyclopentenone | ![structure] methyl 7-oxoheptanoate | ![structure] 2-methylthio-5-(1-hydroxy-6-methoxycarbonylhexyl)-4-octyl-4-trimethylsilyloxy-2-cyclopentenone | 76 | 0.19(9H, s), 0.7–1.0(3H, brt), 1.0–2.2 (23H, m), 2.31(2H, t, J=7.2 Hz), 2.35(3H, s), 2.45(1H, d), 3.67(3H, s), 3.8–4.1(1H, m), 6.75(1H, (1H, s) |

EXAMPLE 72

Synthesis of 5-(1,4,7-trihydroxy-2-heptenyl)-4-hydroxy-2-methylthio-4-(4-phenoxybutyl)-2-cyclopentenone

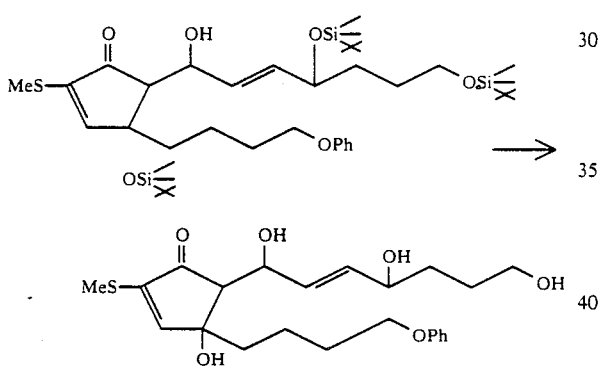

To a solution of 270 mg of 5-[4,7-bis(t-butyldimethylsilyloxy)-1-hydroxy-2-heptenyl]-2-methylthio-4-(4-phenoxybutyl)-4-trimethylsilyloxy-2-cyclopentenone obtained in Example 62 dissolved in 15 ml of acetonitrile, 2 ml of pyridine was added. While stirring the mixture under ice-cooling, 1 ml of a hydrogen fluoride-pyridine solution was added and the mixture was stirred at 0° C.-room temperature for 16 hours. The mixture was poured onto saturated aqueous sodium hydrogencarbonate, and the mixture was extracted with ethyl acetate. The organic layers were combined, washed with saturated aqueous sodium chloride and dried over anhydrous magnesium sulfate. After filtration and concentration, the concentrate was subjected to silica gel chromatography to give 114 mg (yield 71%) of 5-(1,4,7-trihydroxy-2-heptenyl)-4-hydroxy-2-methylthio-4-(4-phenoxybutyl)-2-cyclopentenone.

Spectrum data
¹H-NMR CDCl₃ δ
1.1–2.2 (15H, m), 2.35 (3H, s), 2.6–2.9 (1H, m), 3.5–3.7 (2H, m), 3.97 (2H, t, J=5.3 Hz), 4.0–4.3 (1H, m), 4.4–4.8 (1H, m), 5.5–6.2 (2H, m), 6.7–7.1 (4H, m), 7.1–7.5 (2H, m).

EXAMPLE 73

Synthesis of 2-methylthio-5-(1-hydroxy-6-methoxycarbonylhexyl)-4-hydroxy-4-octyl-2-cyclopentenone

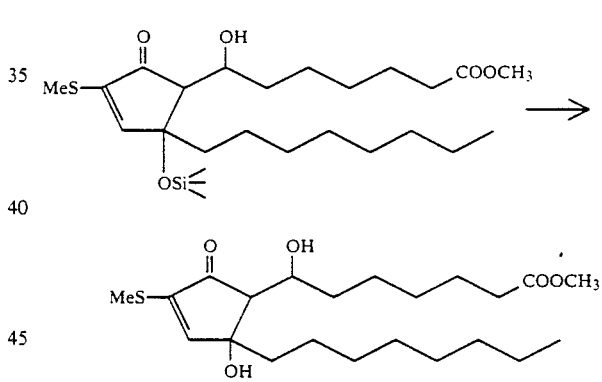

To a solution of 63 mg of 2-methylthio-5-(1-hydroxy-6-methoxycarbonylhexyl)-4-octyl-4-trimethylsilyloxy-2-cyclopentenone obtained in Example 71 dissolved in 6 ml of acetonitrile was added 130 μl of pyridine. A hydrogen fluoride-pyridine solution (260 μl) was added, and the mixture was stirred for 18 hours. The reaction mixture was poured onto saturated aqueous sodium hydrogencarbonate, and the mixture was extracted with ethyl acetate. The organic layers were combined, washed with saturated aqueous sodium chloride and dried over anhydrous magnesium sulfate. After filtration and concentration, the concentrate was subjected to silica gel column chromatography to give 22 mg (yield 41%) of 2-methylthio-5-(1-hydroxy-6-methoxycarbonylhexyl)-4-hydroxy-4-octyl-2-cyclopentenone.

Spectrum data
¹H-NMR CDCl₃ δ
0.86 (3H, t, J=5.7 Hz), 1.1–2.1 (24H, m), 2.2–2.5 (2H, m), 2.35 (3H, s), 2.45 (1H, d), 3.67 (3H, s), 3.8–4.1 (1H, m), 6.75 (1H, s).

EXAMPLE 74

Synthesis of 5-(1,4,7-trihydroxy-2-heptenyl)-4-hydroxy-2-methylsulfinyl-4-(4-phenoxybutyl)- 2-cyclopentenone

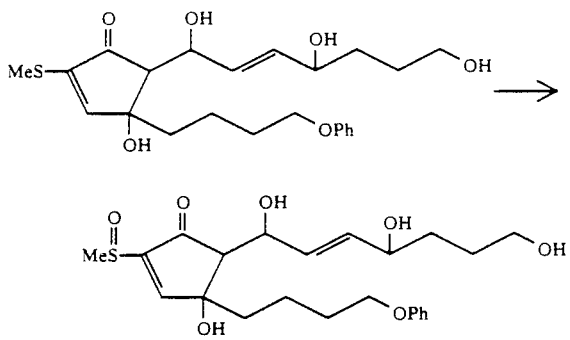

To a solution of 35 mg of 5-(1,4,7-trihydroxy-2-heptenyl)-4-hydroxy-2-methylthio-4-(4-phenoxybutyl)-2-cyclopentenone obtained in Example 72 dissolved in 2 ml of dichloromethane was added 16 mg of 3-chloroperbenzoic acid, and the mixture was stirred for 3 hours. Saturated aqueous sodium hydrogencarbonate was added, and the mixture was extracted with ethyl acetate. The organic layers were combined, washed with saturated aqueous sodium chloride, dried over anhydrous magnesium sulfate, filtered and concentrated, followed by silica gel column chromatography to give 7.3 mg (yield 46%) of 5-(1,4,7-trihydroxy-2-heptenyl)-4-hydroxy-2-methylsulfinyl-4-(4-phenoxybutyl)-2-cyclopentenone.

Spectrum data
$^1$H-NMR CDCl$_3$ δ
1.2–2.3 (15H, m), 2.84 (3H, s), 2.6–3.0 (1H, m), 3.5–3.7 (2H, m), 3.95 (2H, t, J=5.7 Hz), 4.0–4.3 (1H, m), 4.4–4.8 (1H, m), 5.5–6.2 (2H, m), 6.7–7.1 (3H, m), 7.1–7.5 (3H, m).

EXAMPLE 75

Synthesis of 5-[4,7-bis(t-butyldimethylsilyloxy)-2-heptenylidene]-2-methylthio-4-(4-phenoxybutyl)-4-trimethylsilyloxy-2-cyclopentenone

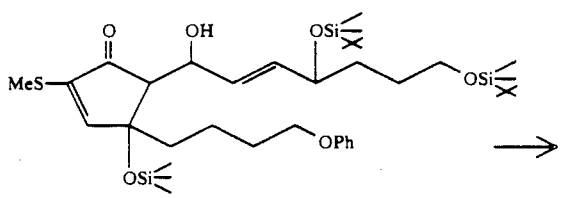

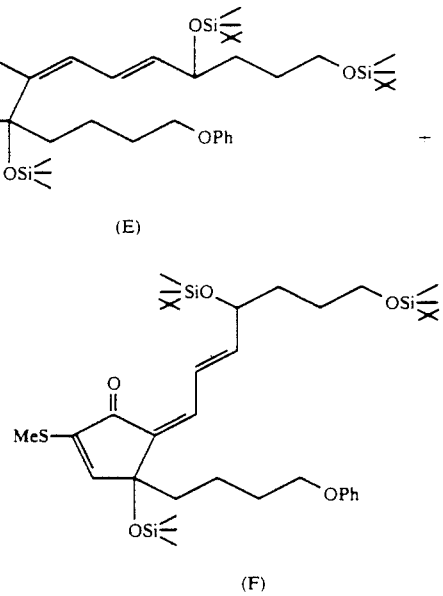

To a solution of 1.00 g of 5-[4,7-bis(t-butyldimethylsilyloxy)-1-hydroxy-2-heptenyl]-2-methylthio-4-(4-phenoxybutyl)-4-trimethylsilyloxy-2-cyclopentenone obtained in Example 62 dissolved in 10 ml of dichloromethane was added under ice-cooling and stirring 497 mg of dimethylaminopyridene, and then 147 μl of methanesulfonyl chloride was added dropwise. The temperature of the mixture was gradually elevated to room temperature, and then stirred for 6 hours. Saturated aqueous potassium hydrogensulfate was added, and the mixture was extracted with ethyl acetate. The organic layers were combined, washed with saturated aqueous sodium hydrogencarbonate and with saturated aqueous sodium chloride in the order mentioned, and dried over anhydrous sodium sulfate. After filtration and concentration, the concentrate was subjected to silica gel chromatography to give 644 mg (yield 66%) of low polarity isomer and 255 mg (yield 26%) of high polarity isomer of 5-[4,7-bis(t-butyldimethylsilyloxy)-2-heptenylidene]-2-methylthio-4-(4-phenoxybutyl)-4-trimethylsilyloxy-2-cyclopentenone.

Spectrum data
Less polar isomer (F)
$^1$H-NMR CDCl$_3$ δ
0–0.1 (m, 21H), 0.90 (s, 9H), 0.93 (s, 9H), 1.1–2.1 (m, 10H), 2.36 (s, 3H), 3.4–3.75 (m, 2H), 3.98 (t, 2H, J=6.3 Hz), 4.1–4.5 (m, 1H), 6.13 (dd, 1H, J=15.0, 6.0 Hz), 6.54 (d, 1H, J=12.5 Hz), 6.63 (s, 1H), 6.75–7.10 (m, 3H), 7.15–7.45 (m, 2H), 7.68 (dd, 1H, J=15.0, 12.5 (Hz).
More polar isomer (E)
$^1$H-NMR CDCl$_3$ δ
0–0.1 (m, 21H), 0.89 (s, 18H), 1.1–2.2 (m, 10H), 2.37 (s, 3H), 3.4–3.75 (m, 2H), 3.93 (t, 2H, J=6.3 Hz), 4.15–4.55 (m, 1H), 5.9–6.5 (m, 1H), 6.67 (s, 1H), 6.5–7.1 (m, 5H), 7.15–7.45 (m, 2H).

EXAMPLES 76–84

2-Substituted-2-cyclopentenones listed in Table 8 were obtained in the same manner as in Example 75.

TABLE 8

| Example No. | Starting compound | 2-Substituted-2-cyclopentenone | Yield (%) | NMR (δCDCl₃) |
|---|---|---|---|---|
| 76 | 2-methylthio-5-[1-hydroxy-3-(4-methoxycarbonylcyclohexyl)-propyl]-4-(4-phenoxybutyl)-4-trimethylsilyloxy-2-cyclopentenone | 2-methylthio-5-[3-(4-methoxycarbonylcyclohexyl)propylidene]-4-(4-phenoxybutyl)-4-trimethylsilyloxy-2-cyclopentenone | 72 | 0.07(9H, s), 1.1–2.8(20H, m), 2.36(3H, s), 3.68(3H, s), 3.9–4.3(2H, m), 6.7–7.5(7H, m) |
| 77 | 2-methylthio-5-[1-hydroxy-4-(4-methoxyphenyl)butyl]-4-(4-phenoxybutyl)-4-trimethylsilyloxy-2-cyclopentenone | 2-methylthio-5-[4-(4-methoxyphenyl)butylidene]-4-(4-phenoxybutyl)-4-trimethylsilyloxy-2-cyclopentenone | 39 | 0.05(9H, s), 1.1–2.9(12H, m), 2.35(3H, s), 3.75(3H, s), 3.8–4.2(2H, m), 6.6–7.5(7H, m) |
| 78 | 2-phenylthio-5-(1-hydroxyoctyl)-4-(4-phenoxybutyl)-4-trimethylsilyloxy-2-cyclopentenone | 2-phenylthio-5-octenylidene-4-(4-phenoxybutyl)-4-trimethylsilyloxy-2-cyclopentenone | 44 | 0.06(9H, s), 0.7–1.0(3H, br t), 1.0–2.2(18H, m), 4.0 (2H, br t, J=5.8Hz), 6.7–7.5 (12H, m) |

TABLE 8-continued

| Example No. | Starting compound | 2-Substituted-2-cyclopentenone | Yield (%) | NMR (δCDCl₃) |
|---|---|---|---|---|
| 79 | 2-methylthio-5-(1-hydroxy-6-methoxycarbonylhexyl)-4-[3-(3,4-dimethoxyphenyl)propyl]-4-trimethylsilyloxy-2-cyclopentenone | 2-methylthio-5-(6-methoxy-carbonylhexylidene)-4-[3-(3,4-dimethoxyphenyl)propyl]-4-trimethylsilyloxy-2-cyclopentenone | 71 | 0.09(9H, s), 1.0–2.0(10H, m), 2.0–2.8(5H, m), 2.35(3H, s), 3.63(3H, s), 3.84(6H, s), 4.8–5.2(1H, m), 6.7–7.1(4H, m) |
| 80 | 2-methylthio-5-(1-hydroxy-6-methoxycarbonylhexyl)-4-(3,7-dimethyloctyl)-4-trimethylsilyloxy-2-cyclopentenone | 2-methylthio-5-(6-methoxy-carbonylhexylidene)-4-(3,7-dimethyloctyl)-4-trimethylsilyloxy-2-cyclopentenone | 54 | 0.09(9H, s), 0.83(9H, d, J=4.5Hz), 0.9–2.5(22H, m), 2.35(3H, s), 3.67(3H, s), 6.6–7.0(2H, m) |
| 81 | 2-methylthio-5-(1-hydroxy-6-methoxycarbonylhexyl)-4-(1-hexynyl)-4-trimethylsilyloxy-2-cyclopentenone | 2-methylthio-5-(6-methoxy-carbonylhexylidene)-4-(1-hexynyl)-4-trimethylsilyloxy-2-cyclopentenone | 62 | 0.06(9H, s), 0.7–1.0(3H, br), 1.0–2.4(16H, m), 2.35(3H, s), 3.68(3H, s), 6.6–7.0(2H, m) |
| 82 | | | 49 | 0.01–0.10(15H, m), 0.89(9H, s), 1.0–2.4(17H, m), 2.36(3H, s), 3.67(3H, s), 4.6–4.8(1H, m), 5.3–5.9(2H, m), 6.6–7.1(2H, m) |

TABLE 8-continued

2-Substituted-2-cyclopentenone

| Example No. | Starting compound | 2-Substituted-2-cyclopentenone | Yield (%) | NMR (δCDCl₃) |
|---|---|---|---|---|
| 83 | 2-methylthio-5-(1-hydroxy-6-methoxycarbonyl-2-hexynyl)-4-(3-t-butyldimethylsilyloxy-3-cyclohexyl-1-propenyl)-4-trimethylsilyloxy-2-cyclopentenone | 2-methylthio-5-(6-methoxycarbonyl-2-hexynylidene)-4-(3-t-butyldimethylsilyloxy-3-cyclohexyl-1-propenyl)-4-trimethylsilyloxy-2-cyclopentenone | 51 | 0.07(9H, s), 1.29(3H, s), 1.1–2.4(10H, m), 2.36(3H, s), 3.69(3H, s), 6.6–7.1(2H, m) |
| 84 | 2-methylthio-5-(1-hydroxy-6-methoxycarbonylhexyl)-4-methyl-4-trimethylsilyloxy-2-cyclopentenone | 2-methylthio-5-(6-methoxycarbonylhexylidene)-4-methyl-4-trimethylsilyloxy-2-cyclopentenone | 40 | 0.03(9H, s), 0.7–1.0(3H, brt), 1.0–2.0(20H, m), 2.1–2.5(4H, m), 2.34(3H, s), 3.68(3H, s), 6.5–6.9(2H, m) |
|  | 2-methylthio-5-(1-hydroxy-6-methoxycarbonylhexyl)-4-octyl-4-trimethylsilyloxy-2-cyclopentenone | 2-methylthio-5-(6-methoxycarbonylhexylidene)-4-octyl-4-trimethylsilyloxy-2-cyclopentenone |  |  |

EXAMPLE 85

Syntheses of
5-](Z)-4,7-dihydroxy-2-heptenylidene]-2-methylthio-4-4-trimethylsilyloxy-(4-phenoxybutylidene)-2-cyclopentenone and
5-[(Z)-4,7-dihydroxy-2-heptenylidene]-4-hydroxy-2-methylthio-4-(4-phenoxybutyl)-2-cyclopentenone

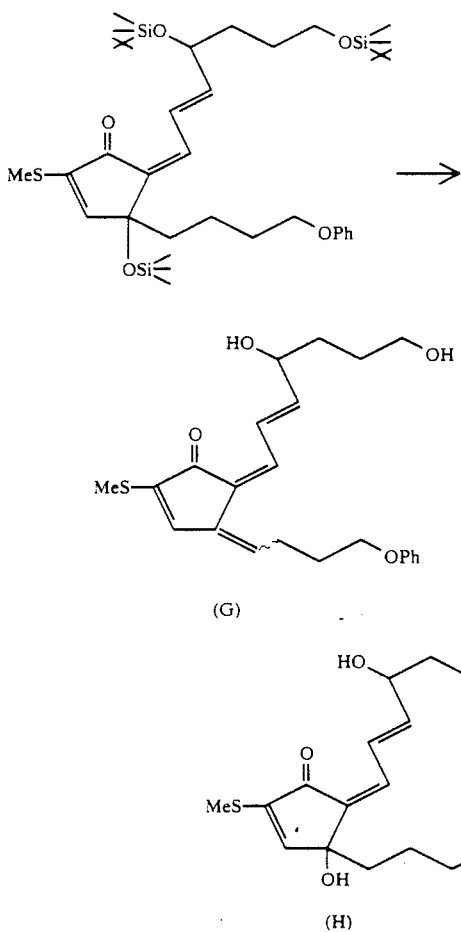

To a solution of 9 ml of pyridine dissolved in 50 ml of acetonitrile was added, 4.5 ml of hydrogen fluoride-pyridine solution, under ice-cooling and stirring. A solution of 1.41 g of 5-[(Z)-4,7-bis(t-butyldimethylsilyloxy)-2-heptenylidene]-2-methylthio-4-(4-phenoxybutyl)-4-trimethylsilyloxy-2-cyclopentenone obtained in Example 75 in 15 ml of acetonitrile was added, and the mixture was stirred at 0° C. for 10 minutes, and at room temperature for 8 hours. The reaction mixture was poured onto saturated aqueous sodium hydrogencarbonate, and the mixture was extracted for 3 times with ethyl acetate. The organic layers were combined, washed once with saturated aqueous sodium hydrogencarbonate and twice with saturated aqueous sodium chloride. The product was dried over anhydrous magnesium sulfate, filtered and concentrated. The oily product obtained was subject to silica gel column chromatography to obtain 158 mg (yield 20%) of 5-[(Z)-4,7-dihydroxy-2-heptenylidene]-2-methylthio-4-(4-phenoxybutylidene)-2-cyclopentenone and 353 mg (yield 43%) of 5-[(Z)-4,7-dihydroxy-2-heptenylidene]-4-hydroxy-2-methylthio-4-(4-phenoxybutyl)-2-cyclopentenone.

Spectrum data
(G) $^1$H-NMR-CDCl$_3$ δ
1.4-2.9 (m, 10H), 2.26 (s, 3H), 3.4-3.9 (m, 2H), 4.01 (t, 2H, J=6.0 Hz), 5.83 (t, 1H, J=7.9 Hz), 6.23 (dd, 1H, J=16.0, 6.5 Hz), 6.74 (d, 1H, J=11.0 Hz), 6.7-7.5 (m, 8H), 7.87 (dd, J=16.0, 11.0 Hz).
(H) $^1$H-NMR-CDCl$_3$ δ
1.2-2.7(13H, m), 2.33 (3H, s), 3.5-3.8 (2H, m), 3.94 (2H, t, J=6.0 Hz), 4.15-4.50 (1H, m), 6.15 (1H, dd, J=15.2, 6.4 Hz), 6.61 (1H, d, J=11.4 Hz), 6.62 (1H, s), 6.7-7.0 (3H, m), 7.1-7.4 (2H, m), 7.67 (1H, dd, J=15.4, 11.4 Hz).

EXAMPLE 86

Synthesis of
5-[(Z)-4,7-dihydroxy-2-heptenylidene]-2-methylthio-4-(4-phenoxybutylidene)-2-cyclopentenone

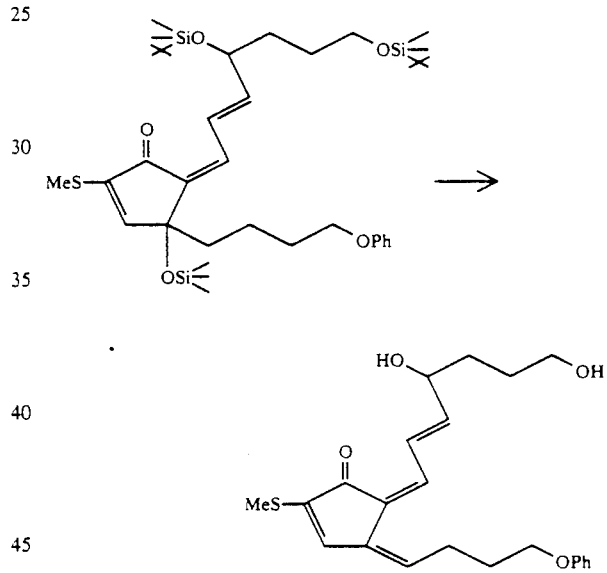

To 1.14 g of 5-[(Z)-4,7-bis(t-butydimethylsilyloxy)-2-heptenylidene]-2-methylthio-4-(4-phenoxybutyl)-4-trimethylsilyloxy-2-cyclopentenone obtained in Example 75 was added 40 ml of a mixture of acetic acid:tetrahydrofuran:water=3:1:1, and the mixture was stirred at room temperature for 18 hours. After the mixture was concentrated with an addition of toluene, saturated aqueous sodium hydrogen carbonate was added, and the mixture was extracted for 3 times with ethyl acetate. The organic layers were combined, washed successively with saturated aqueous sodium hydrogencarbonate and saturated aqueous sodium chloride, and dried over anhydrous magnesium sulfate. After filtration and concentration, the concentrate was subjected to silica gel column chromatography to give 407 mg (yield 61%) of 5-[(Z)-4,7-dihydroxy-2-heptenylidene]-4-hydroxy-2-methylthio-4-(4-phenoxybutylidene)-2-cyclopentenone.

EXAMPLE 87

Synthesis of 5-[(Z)-4,7-dihydroxy-2-heptenylidene]-4-hydroxy-2-methylsulfinyl-4-(4-phenoxybutylidene)-2-cyclopentenone

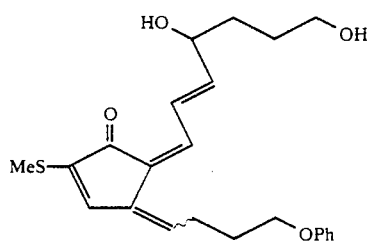

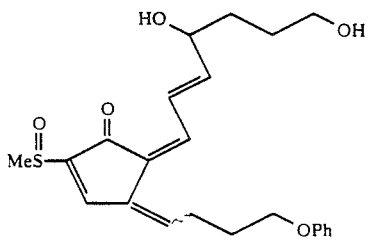

To a solution of 20 mg of 5-[(Z)-4,7-dihydroxy-2-heptenylidene]-4-hydroxy-2-methylthio-4-(4-phenoxybutylidene)-2-cyclopentenone obtained in Example 85 or Example 86 dissolved in 3 ml of methanol was added a solution of 102 mg of sodium periodate in 500 μl of water, and the mixture was stirred for 5 hours. Saturated aqueous sodium chloride was added, and the mixture was extracted for 3 times with ethyl acetate. The organic layers were combined, and washed with saturated aqueous sodium chloride, followed by drying over anhydrous magnesium sulfate. After filtration and concentration, the concentrate was subjected to silica gel column chromatography to give 13.3 mg (yield 64%) of 5-[(Z)--4,7-dihydroxy-2-heptenylidene]-4-hydroxy-2-methylsulfinyl-4-(4-phenoxybutylidene)-2-cyclopentenone.

Spectrum data $^1$H-NMR CDCl$_3$ δ

1.2–2.2 (m, 7H), 2.2–3.2 (m, 3H), 2.85 (s, 3H), 3.5–3.8 (m, 2H), 4.03 (t, 2H, J=6.3 Hz), 4.1–4.6 (m, 1H), 6.0–6.75 (m, 2H), 6.75–7.15 (m, 5H), 7.15–7.45 (m, 3H) 7.81 (dd, 1H, J=15.0, 11.3 Hz), 8.29 and 8.36 (s, 1H).

EXAMPLE 88

Syntheses of 5-[(Z)-4,7-dihydroxy-2-heptenyidene]-2-methylsulfinyl-4-(4-phenoxybutylidene)-2-cyclopentenone and 5-[(Z)-4,7-dihydroxy-2-heptenylidene]-2-methylsulfonyl-4-(4-phenoxybutylidene)-2-cyclopentenone

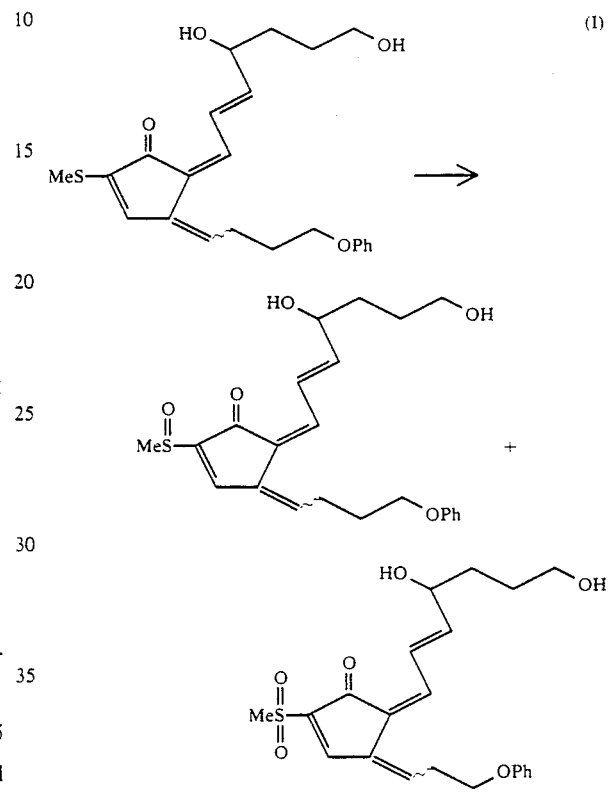

To a solution of 280 mg of 5-[(Z)-4,7-dihydroxy-2-heptenylidene]-2-methylthio-4-(4-phenoxybutylidene)-2-cyclopentenone obtained in Example 85 or Example 86 dissolved in 15 ml of dichloromethane was added a solution of 200 mg of 3-chloroperbenzoic acid in 5 ml of dichloromethane. Saturated aqueous sodium hydrogencarbonate was added, and the mixture was extracted with ethyl acetate. The organic layers were combined, washed with saturated aqueous sodium chloride and dried over anhydrous sodium sulfate. After filtration and concentration, the concentrate was subjected to silica gel column chromatography to give 36 mg (yield 13%) of 5-[(Z)-4,7-dihydroxy-2-heptenylidene]-2-methylsulfinyl-4-(4-phenoxybutylidene)-2-cyclopentenone and 66 mg (yield 24%) of 5-[(Z)-4,7-dihydroxy-2-heptenylidene]-2-methylsulfonyl-4-(4-phenoxybutylidene)-2-cyclopentenone.

Spectrum data (I) $^1$H-NMR CDCl$_3$ δ

1.3–2.3 (8H, m), 2.5–2.9 (2H, m), 3.10 and 3.11 (3H, s), 3.5–3.85 (2H, m), 4.00 (2H, t, J=5.9 Hz), 4.15–4.55 (1H, m), 6.0–6.75 (2H, m), 6.75–7.05 (4H, m), 7.05–7.40 (2H, m), 7.80 (1H, J=11.3, 15.0 Hz), 8.43 and 8.51 (1H, s).

EXAMPLE 89

Synthesis of
2-methylsulfonyl-5-[(Z)-4,7-dihydroxy-2-heptenylidene]-4-(4-phenoxybutylidene)-2-cyclopetenone

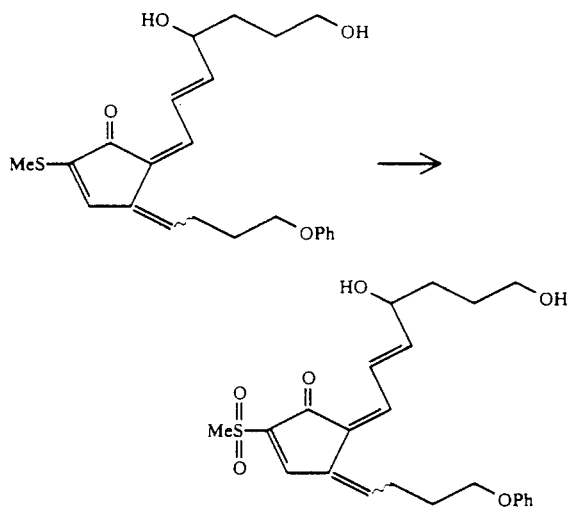

To a solution of 20 mg of 2-methylthio-5-[(Z)-4,7-dihydroxy-2-heptenyldidene]-4-(4-phenoxybutylidne)-2-cyclopentenone obtained in Example 85 or Example 86 dissolved in 2 ml of methanol was added 2 ml of an aqueous solution of 60 mg of $2KHSO_5 \cdot KHSO_4 \cdot K_2SO_4$, and the mixture was stirred for 20 hours. Saturated aqueous sodium hydrogencarbonate was added, and the mixture was extracted with ethyl acetate. The organic layers were combined, and washed with saturated aqueous sodium chloride, dried over anhydrous magnesium sulfate, filtered and concentrated, followed by silica gel chromatography to give 5.6 mg (yield 26%) of 2-methylsulfonyl-5-[(Z)-4,7-dihydroxy-2-heptenylidene]-4-(4-phenoxybutylidene)-2-cyclopentenone.

EXAMPLE 90

Synthesis of
2-methylsulfonyl-5-[(Z)-4,7-dihydroxy-2-heptenylidene]-4-(4-phenoxybutylidene)-2-cyclopentenone

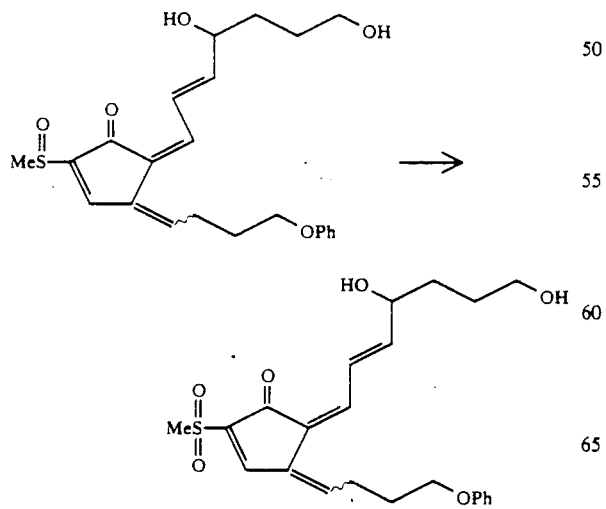

To a solution of 6.5 mg of 2-methylsulfinyl-5-[(Z)-4,7-dihydroxy-2-heptenylidene]-4-(4-phenoxybutylidene)-2-cyclopentenone obtained in Example 87 or Example 88 dissolved in 1.5 ml of dichloromethane was added 3 mg of 3-chloroperbenzoic acid, and the mixture was stirred for 4 hours. Saturated aqueous sodium hydrogencarbonate was added, and the mixture was extracted with ethyl acetate. The extract was washed with saturated aqueous sodium chloride, dried over anhydrous magnesium sulfate, filtered and concentrated, followed by silica gel chromatography to give 3.9 mg (yield 60%) of 2-methylsulfonyl-5-[(Z)-4,7-dihydroxy-2-heptenylidene]-4-(4-phenoxbutylidene)-2-cyclopentenone.

EXAMPLE 91

Synthesis of
5-[(E)-4,7-dihydroxy-2-heptenylidene]-4-hydroxy-2-methylthio-4-(4-phenoxybutyl)-2-cyclopentenone

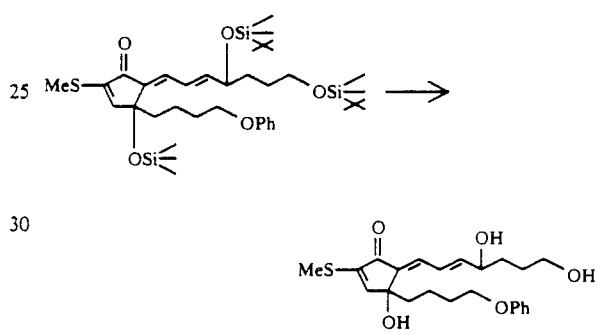

To 255 mg of 5-[(E)-4,7-bis(t-butyldimethylsilyloxy)-2-heptenylidene]-2-methylthio-4-(4-phenoxybutyl)-4-trimethylsilyloxy-2-cyclopentenone obtained in Example 75 was added 20 ml of a mixture of acetic acid:tetrahydrofuran:water=3:1:1, and the mixture was stirred at room temperature for 26 hours. After concentration with an addition of toluene, saturated aqueous sodium hydrogencarbonate was added, and the mixture was extracted 3 times with ethyl acetate. The organic layers were combined, washed successively with saturated aqueous sodium hydrogencarbonate and saturated aqueous sodium chloride, and dried over anhydrous magnesium sulfate. After filtration and concentration, the concentrate was subjected to silica gel column chromatography to give 94 mg (yield 63%) of 5-[(E)-4,7-dihydroxy-2-heptenylidene]-4-hydroxy-2-methylthio-4-(4-phenoxybutyl)-2-cyclopentenone.

EXAMPLE 92

Synthesis of
5-[(E)-4,7-dihydroxy-2-heptenylidene]-4-hydroxy-2-methylthio-4-(4-phenoxybutyl1-2-cyclopetenone

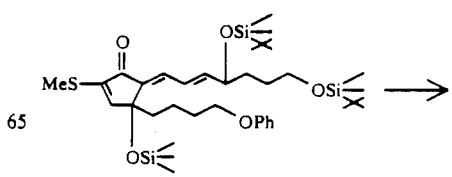

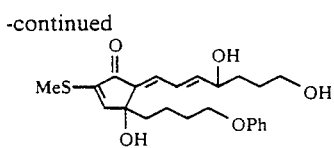

To a solution of 660 mg of 5-[(E)-4,7-bis(t-butyldimethylsilyloxy)-2-heptenylidene]-2-methylthio-4-(4-phenoxybutyl)-4-trimethylsilyloxy-2-cyclopentenone obtained in Example 75 dissolved in 50 ml of acetonitrile was added 4 ml of pyridine, under ice-cooling and stirring. A hydrogen-pyridine solution (2 ml) was added, and the mixture was stirred at 0° C. for 24 hours. The reaction mixture was poured onto saturated aqueous sodium hydrogencarbonate, and the mixture was extracted 3 times with ethyl acetate. The organic layers were combined, washed with saturated sodium chloride and dried over anhydrous magnesium sulfate. After filtration and concentration, the concentrate was subjected to silica gel column chromatography to give 320 mg (yield 83%) of 5-[(E)-4,7-dihydroxy-2-heptenylidene]-4-hydroxy-2-methylthio-4-(4-phenoxybutyl)-2-cyclopentenone.

Spectrum data $^1$H-NHR CDCl$_3$ δ

1.2–2.9 (m, 13H), 2.37 (s, 3H), 3.5–3.8 (m, 2H), 3.95 (t, 2H, J=6.3 Hz), 4.15–4.5 (m, 1H), 6.0–6.5 (m, 1H), 6.67 (s, 1H), 6.7–7.15 (m, 4H), 7.15–7.5 (m, 3H).

EXAMPLES 93–101

2-Substituted-2-cyclopentenones listed in Table 9 were obtained in the same manner as in Example 92.

TABLE 9

| Example No. | Starting compound | 2-Substituted-2-cyclopentenone | Yield (%) | NMR δCDCl₃ |
|---|---|---|---|---|
| 93 | 2-methylthio-5-[3-(4-methoxycarbonylcyclohexyl)propylidene]-4-(4-phenoxybutyl)-4-trimethylsilyloxy-2-cyclopentenone | 2-methylthio-5-[3-(4-methoxycarbonylcyclohexyl)propylidene]-4-(4-phenoxybutyl)-4-hydroxy-2-cyclopentenone | 47 | 1.1–2.8(21H, m), 2.36 (3H, s), 3.68(3H, s), 3.9–4.3(2H, m), 6.6–7.5 (7H, m) |
| 94 | 2-methylthio-5-[4-(4-methoxyphenyl)butylidene]-4-(4-phenoxybutyl)-4-trimethylsilyloxy-2-cyclopentenone | 2-methylthio-5-[4-(4-methoxyphenyl)butylidene]-4-(4-phenoxybutyl)-4-hydroxy-2-cyclopentenone | 64 | 1.1–2.9(13H, m), 2.36 (3H, s), 3.75(3H, s), 3.8–4.2(2H, m), 6.6–7.5 (7H, m) |
| 95 | 2-phenylthio-5-octenylidene-4-(4-phenoxybutyl)-4-trimethylsilyloxy-2-cyclopentenone | 2-phenylthio-5-octenylidene-4-(4-phenoxybutyl)-4-hydroxy-2-cyclopentenone | 75 | 0.7–1.0(3H, brt), 1.0–2.2(18H, m), 2.4–2.7(1H, m), 4.0 (2H, brt, J=5.8Hz), 6.7–7.5(12H, m) |

TABLE 9-continued

| Example No. | Starting compound | 2-Substituted-2-cyclopentenone | Yield (%) | NMR δCDCl₃ |
|---|---|---|---|---|
| 96 | 2-methylthio-5-(6-methoxy-carbonylhexylidene)-4-[3-(3,4-dimethoxyphenyl)propyl]-4-trimethylsilyloxy-2-cyclopentenone | 2-methylthio-5-(6-methoxy-carbonylhexylidene)-4-[3-(3,4-dimethoxyphenyl)propyl]-4-hydroxy-2-cyclopentenone | 58 | 1.0–3.2(17H, m), 2.35 (3H, s), 3.64(3H, s), 3.83(6H, s), 6.6–7.0 (5H, m) |
| 97 | 2-methylthio-5-(6-methoxy-carbonylhexylidene)-4-(3,7-dimethyloctyl)-4-trimethyl-silyloxy-2-cyclopentenone | 2-methylthio-5-(6-methoxy-carbonylhexylidene)-4-(3,7-dimethyloctyl)-4-hydroxy-2-cyclopentenone | 71 | 0.84(9H, d, J=4.5Hz), 0.9–2.7 (23H, m), 2.36(3H, s), 3.68(3H, s), 6.6–7.0 (2H, m) |
| 98 | 2-methylthio-5-(6-methoxy-carbonylhexylidene)-4-(1-hexynyl)-4-trimethylsilyloxy-2-cyclopentenone | 2-methylthio-5-(6-methoxy-carbonylhexylidene)-4-(1-hexynyl)-4-hydroxy-2-cyclopentenone | 67 | 0.7–1.0(3H, brt), 1.0–2.4(16H, m), 2.35 (3H, s), 2.6–2.9 (1H, m), 3.68(3H, s), 6.6–7.0(2H, m) |

TABLE 9-continued

| Example No. | Starting compound | 2-Substituted-2-cyclopentenone | Yield (%) | NMR δCDCl₃ |
|---|---|---|---|---|
| 99 | 2-methylthio-5-(6-methoxy-carbonyl-2-hexynylidene)-4-(3-t-butyldimethylsiloxy-3-cyclohexyl-1-propenyl)-4-trimethylsilyloxy-2-cyclopentenone | 2-methylthio-5-(6-methoxy-carbonyl-2-hexynylidene)-4-(3-hydroxy-3-cyclohexyl-1-propenyl)-4-hydroxy-2-cyclopentenone | 47 | 1.0–2.4(17H, m), 2.36 (3H, s), 2.5–2.8 (2H, m), 3.68(3H, s), 4.6–4.8(1H, m), 5.3–5.9 (2H, m), 6.6–7.1(2H, m) |
| 100 | 2-methylthio-5-(6-methoxy-carbonylhexylidene)-4-methyl-4-trimethylsilyloxy-2-cyclopentenone | 2-methylthio-5-(6-methoxy-carbonylhexylidene)-4-methyl-4-hydroxy-2-cyclopentenone | 72 | 1.30(3H, s), 1.1–2.7 (11H, m), 2.35(3H, s), 3.68(3H, s), 6.6–7.1 (2H, m) |
| 101 | 2-methylthio-5-(6-methoxy-carbonylhexylidene)-4-octyl-4-trimethylsilyloxy-2-cyclopentenone | 2-methylthio-5-(6-methoxy-carbonylhexylidene)-4-octyl-4-hydroxy-2-cyclopentenone | 62 | 0.86(3H, t, J=5.7Hz), 1.1–2.1 (21H, m), 2.2–2.5 (2H, m), 2.36(3H, s), 2.5–3.0(2H, m), 3.68 (3H, s), 6.5–6.9(2H, m) |

EXAMPLE 102

Synthesis of
5-[(Z)-4,7-dihydroxy-2-heptenylidene]-4-hydroxy-2-methylsulfinyl-4-phenoxybutyl-2-cyclopentenone

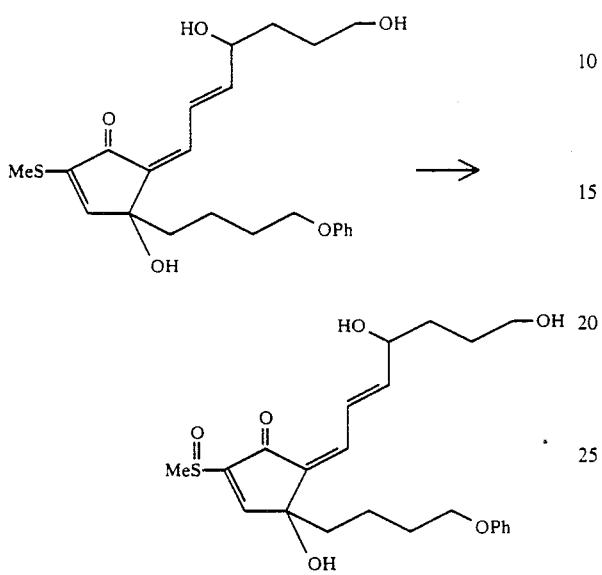

To a solution of 110 mg of 5-[(Z)-4,7-dihydroxy-2-heptenylidene]-4-hydroxy-2-methylthio-4-(4-phenoxybutyl)-2-cyclopentenone obtained in Example 85 dissolved in 15 ml of dichloromethane was added a solution of 75 mg of 3-chloroperbenzoic acid in 5 ml of dichloromethane, under ice-cooling and stirring, and the mixture was stirred at 0° C. to room temperature for 4 hours. Saturated aqueous sodium hydrogencarbonate was added, and the mixture was extracted for 3 times with ethyl acetate. The organic layer was washed with saturated aqueous sodium chloride and dried over anhydrous sodium sulfate. After filtration and concentration, the concentrate was subjected to silica gel column chromatography to give 33 mg (yield 30%) of low polarity isomer and 19 mg (yield 17%) of high polarity isomer of 5-[(Z)-4,7-dihydroxyheptenylidene]-4-hydroxy-2-methylsulfinyl-4-phenoxybutyl-2-cyclopentenone.

Spectrum data
Less polar isomer
$^1$H-NMR CDCl$_3$ δ
1.2–2.4 (13H, m), 2.84 (3H, s), 3.5–3.8 (2H, m), 3.94 (2H, t, J=5.9 Hz), 4.1–4.5 (1H, m), 6.0–6.4 (1H, m), 6.55–7.0 (4H, m), 7.1–7.8 (3H, m), 7.70 (1H, s).
More polar isomer
$^1$H-NMR CDCl$_3$ δ
1.2–2.5 (13H, m), 2.86 (3H, s), 3.5–3.8 (2H, m), 3.95 (2H, t, J=5.9 Hz), 4.1–4.5 (1H, m), 6.23 (1H, dd, J=15.8, 5.5 Hz), 6.70 (1H, d, J=11.4 Hz), 6.7–7.0 (3H, m), 7.1–7.4 (2H, m), 7.61 (1H, dd, J=14.5, 12.0 Hz), 7.71 (1H, s)

EXAMPLE 103

Synthesis of
5-[(Z)-4,7-dihydroxy-2-heptenylidene]-4-hydroxy-2-methylsulfonyl-4-(4-phenoxybutyl)-2-cyclopetenone

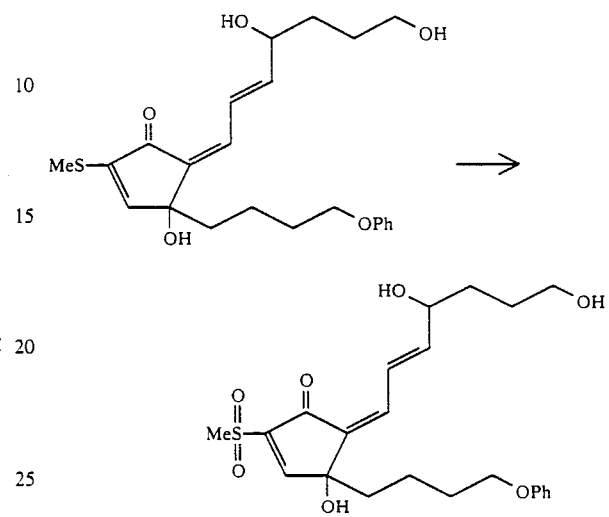

To a solution of 24 mg of 5-[(Z)-4,7-dihydroxy-2-heptenylidene]-4-hydroxy-2-methylthio-4-(4-phenoxybutyl)-2-cyclopentenone obtained in Example 85 dissolved in 2 ml of dichloromethane was added a solution of 24 mg of 3-chloroperbenzoic acid in 240 μl of dichloromethane, and the mixture was stirred for 18 hours. Saturated aqueous sodium hydrogencarbonate was added, and the mixture was extracted with ethyl acetate. The organic layers were combined, washed with saturated aqueous sodium chloride and dried over anhydrous magnesium sulfate. After filtration and concentration, the concentrate was subjected to silica gel column chromatography to give 7.3 mg (yield 30%) of 5-[(Z)-4,7-dihydroxy-2-heptenylidene]-4-hydroxy-2-methylsulfonyl-4-(4-phenoxybutyl)-2-cyclopentenone.

Spectrum data
$^1$H-NMR CDCl$_3$ δ
1.0–2.5 (13H, m), 2.14 (1H, s), 3.6–3.8 (2H, m), 3.94 (2H, t, J=5.9 Hz), 4.1–4.5 (1H, m), 6.0–6.5 (1H, m), 6.5–7.0 (4H, m), 7.1–7.4 (2H, m), 7.4–7.8 (1H, m), 7.94 (1H,s).

EXAMPLE 104

Synthesis of
5-[(E)-4,7-dihydroxy-2-heptenylidene]-4-hydroxy-2-methylsulfinyl-4-(4-phenoxybutyl)-2-cyclopetenone

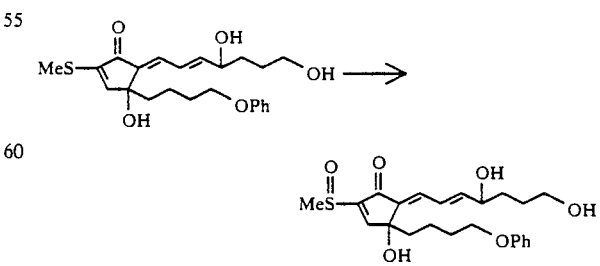

To a solution of 71 mg of 5-[(E)-4,7-dihydroxy-2-heptenylidene]-4-hydroxy-2-methylthio-4-(4-phenoxybutyl)-2-cyclopentenone obtained in Example 91 dissolved in 2 ml of dichloromethane was added a solution of 45 mg of 3-chloroperbenzoic acid in 2 ml of dichloromethane, and the mixture was stirred for 3 hours. Saturated aqueous sodium hydrogencarbonate was added. The mixture was extracted twice with ethyl acetate, and the organic layers were combined, washed with saturated aqueous sodium chloride and dried over anhydrous sodium sulfate. After filtration and concentration, the concentrate was subjected to silica gel column chromatography to give 27 mg (yield 38%) of low polarity isomer and 25 mg (yield 35%) of high polarity isomer of 5-[(E)-4,7-dihydroxyheptenylidene]-4-hydroxy-2-methylsulfinyl-4-(4-phenoxybutyl)-2-cyclopentenone.

Spectrum data
Less polar isomer
$^1$H-NMR CDCl$_3$ δ
1.1–2.7 (13H, m), 2.85 (3H, s), 3.5–3.8 (2H, m), 3.92 (2H, t, J=6.0 Hz), 4.1–4.4 (1H, m), 6.0–6.45 (1H, m), 6.65–7.05 (5H, m), 7.1–7.4 (2H, m), 7.71 (1H, s).
More polar isomer
$^1$H-NMR CDCl$_3$ δ
1.1–2.3 (10H, m), 2.3–3.3 (3H, m), 2.87 (3H, s), 3.5–3.8 (2H, m), 3.91 (2H, t, J=6.0 Hz), 4.1–4.4 (1H, m), 6.0–6.5 (1H, m), 6.6–7.05 (5H, m), 7.1–7.5 (2H, m), 7.69 (1H, s).

EXAMPLE 105

Synthesis of 5-[(E)-4,7-dihydroxy-2-heptenylidene]-4-hydroxy-2-methylsulfonyl-4-(4-phenoxybutyl)-2-cyclopetenone

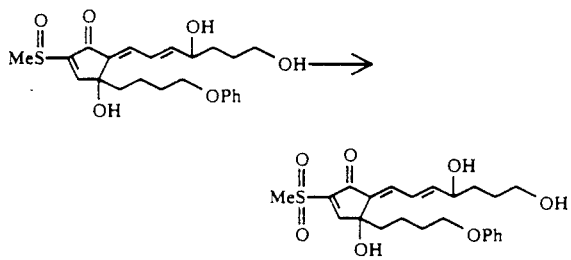

To a solution of 165 mg of 5-[(E)-4,7-dihydroxyheptenylidene]-4-hydroxy-2-methylsulfinyl-4-(4-phenoxybutyl)-2-cyclopentenone obtained in Example 104 dissolved in 30 ml of dichloromethane was added a solution 117 mg of 3-chloroperbenzoic acid in 5 ml of dichloromethane, and the mixture was stirred for 2 hours. The reaction mixture was poured onto saturated aqueous sodium thiosulfate, and the mixture was extracted 3 times with ethyl acetate. The organic layers were combined, washed twice with saturated aqueous sodium hydrogencarbonate and with saturated aqueous sodium chloride, and dried over anhydrous sodium sulfate. After filtration and concentration, the concentrate was subjected to chromatography to give 78 mg (yield 47%) of 5-[(E)-4,7-dihydroxy-2-heptenylidene]-4-hydroxy-2-methylsulfonyl-4-(4-phenoxybutyl)-2cyclopentenone Spectrum data
$^1$H-NMR CDCl$_3$ δ
1.2–2.5 (13H, m), 3.15 (3H, s), 3.5–3.8 (2H, m), 3.93 (2H, t, J=5.9 Hz), 4.1–4.4 (1H, m), 6.1–6.4 (1H, m), 6.65–7.05 (4H, m), 7.05–7.4 (2H, m), 7.99 (1H, s).

EXAMPLE 106

Synthesis of
5-[(E)-4,7-dihydroxy-2-heptenylidene]-4-hydroxy-2-methylsulfinyl-4-(4-phenoxybutyl1-2-cyclopentenone
and
5-[(E)-4,7-dihydroxy-2-heptenylidene]-4-hydroxy-2-methylsulfonyl-4-(4-phenoxybutyl)-2-cyclopentenone

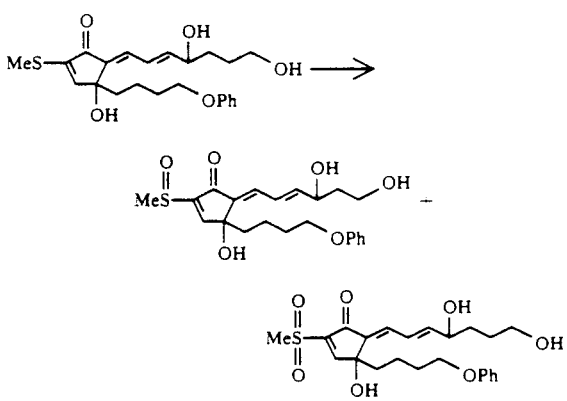

To a solution of 10 mg of 5-[(E)-4,7-dihydroxy-2-heptenylidene]-4-hydroxy-2-methylthio-4-(4-phenoxybutyl)-2-cyclopentenone obtained in Example 91 dissolved in 2 ml of dichloromethane was added 4.8 mg of 3-chloroperbenzoic acid, and the mixture was stirred for 16 hours. Saturated aqueous sodium hydrogencarbonate was added, the mixture was extracted with ethyl acetate, and the organic layer was washed with saturated aqueous sodium chloride. After drying over anhydrous sodium sulfate, filtration and concentration, the concentrate was subjected to silica gel chromatography to give 2.0 mg (yield 20%) of less polar isomer, 4.0 mg (yield 40%) of more polar isomer of 5-[(E)-4,7-dihydroxy-2-heptenylidene]-4-hydroxy-2-methylsulfinyl-4-(4-phenoxybutyl)-2-cyclopentenone and 1.6 mg (yield 16%) of 5-[(E)-4,7-dihydroxy-2-heptenylidene]-4-hydroxy-2-methylsulfonyl-4-(4-phenoxybutyl)-2-cyclopentenone.

EXAMPLE 107

Synthesis of 5-[(E)-4,7-dihydroxy-2-heptenylidene]-4-hydroxy-2-methylsulfonyl-4-(4-phenoxybutyl)-2-cyclopetenone

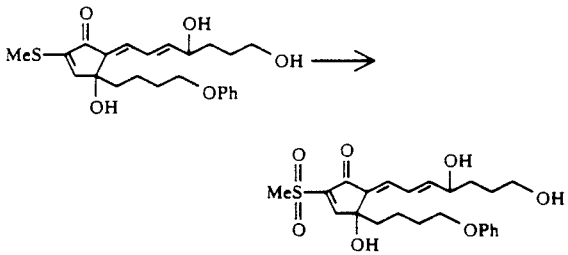

To a solution of 34 mg of 5-[(E)-4,7-dihydroxy-2-heptenylidene]-4-hydroxy-2-methylthio-4-(4-phenoxybutyl)-2-cyclopentenone obtained in Example 91 dissolved in 2 ml of dichloromethane was added a solution 33 mg of 3-chloroperbenzoic acid in 330 μl of dichloromethane, and the mixture was stirred for 18 hours. Saturated aqueous sodium hydrogencarbonate was added, and the mixture was extracted with ethyl acetate. The organic layers were combined, washed with saturated aqueous sodium chloride and dried over anhydrous magnesium sulfate. After filtration and concentration, the concentrate was subjected to silica gel column chromatography to give 13 mg (yield 38%) of 5-[(E)-4,7-dihydroxy-2-heptenylidene]-4-hydroxy-2-methylsulfonyl-4-(4-phenoxybutyl)-2-cyclopentenone.

EXAMPLE 108

Synthesis of 2-methylsulfinyl-4-hydroxy-5-(6-methoxycarbonylhexylidene)-4-octyl-2-cyclopentenone

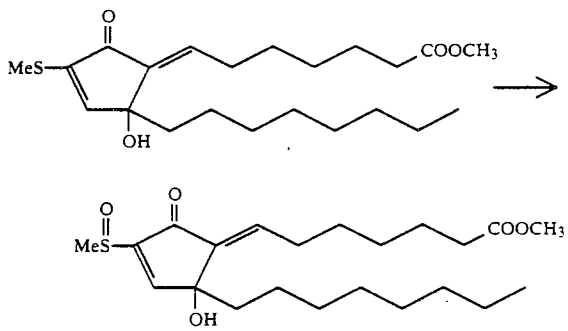

To a solution of 12 mg of 2-methylthio-4-hydroxy-5-(6-methoxycarbonylhexylidene)-4-octyl-2-cyclopentenone obtained in Example 101 dissolved in 2 ml of dichloromethane was added 6.5 mg of 3-chloroperbenzoic acid. After the mixture was stirred at 0° C. for 1 hour, saturated aqueous sodium hydrogencarbonate was added, and the mixture was extracted with ethyl acetate. After washing with saturated aqueous sodium chloride, the product was subjected to silica gel chromatography to obtain 7.3 mg (yield 61%).

Spectrum data
$^1$H-NMR CDCl$_3$ δ
0.86 (3H, t, J=5.7 Hz), 1.1-2.1 (21H, m),
2.2-2.5 (2H, m), 2.5-3.0 (2H, m), 2.87
(3H, s), 3.68 (3H, s), 6.72 (1H, t, J=7 Hz),
7.70 (1H, s).

EXAMPLE 109

Synthesis of 5-[(Z)-4,7-dihydroxy-2-heptenylidene]-2-methylthio-4-methoxy-4-(4-phenoxybutyl)-2-cyclopentenone

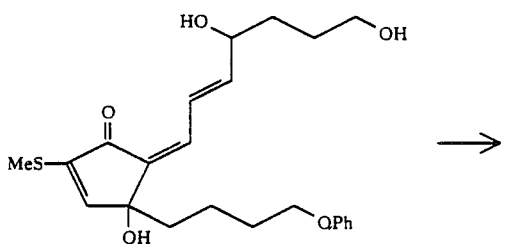

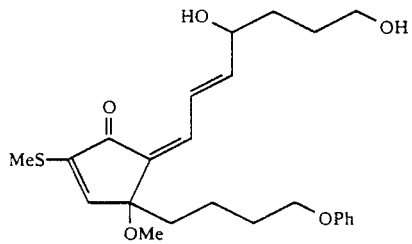

To a solution of 2 mg of 5-[(Z)-4,7-dihydroxy-2-heptenylidene]-2-methylthio-4-hydroxy-4-(4-phenoxybutyl)-2-cyclopentenone obtained in Example 85 dissolved in 1 ml of methanol was added 0.5 μl of acetic acid, and the mixture was stirred for 24 hours. Saturated aqueous sodium hydrogencarbonate was added, and the mixture was extracted with ethyl acetate. The extract was dried over anhydrous magnesium sulfate, filtered and concentrated, followed by silica gel chromatography to give 1.9 mg (yield 95%) of 5-[(Z)-4,7-dihydroxy-2-heptenylidene]-2-methylthio-4-methoxy-4-(4-phenoxybutyl)-2-cyclopentenone.

Spectrum data
$^1$H-NMR CDCl$_3$ δ
1.1-2.1 (12H, m), 2.36 (3H, s), 3.05 (3H, s),
3.55-3.8 (2H, m), 3.93 (2H, t, J=6.0 Hz),
4.1-4.5 (1H, m), 6.17 (1H, dd, J=6.2 ,
15.0 Hz), 6.46 (1H, d, J=11.0 Hz), 6.53
(1H, s), 6.7-7.0 (3H, m), 7.1-7.4 (2H, m),
7.72 (1H, dd, J=11.2, 15.3 Hz).

EXAMPLE 110

Synthesis of 5-[(E)-4,7-diacetoxy-2-heptenylidene]-4-hydroxy-2-methylthio-4-(4-phenoxybutyl)-2-cyclopentenone and 5-[(E)-4,7-diacetoxy-2-heptenylidene]-4-acetoxy-2-methylthio-4-(4-phenoxybutyl)-2-cyclopentenone

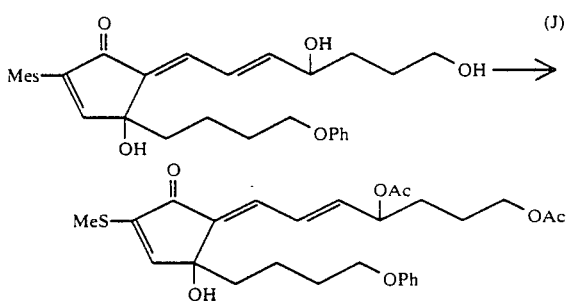

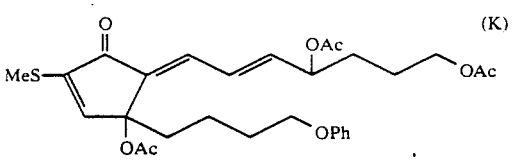

To a solution of 23 mg of 5-[(E)-4,7-dihydroxy-2-heptenylidene]-4-hydroxy-2-methylthio-4-(4-phenoxybutyl)-2-cyclopentenone obtained in Example 91 dissolved in 2 ml of dichloromethane was added 200 μl of triethylamine. Under ice-cooling and stirring, 20 μl of acetylchloride was added, and the mixture was stirred at 0° C. for 2 hours. Saturated aqueous sodium chloride was added, and the mixture was extracted with ethyl acetate. The extract was dried over anhydrous sodium sulfate, filtrate and concentrated, followed by silica gel column chromatography to give 11 mg (yield 43%) of 5-[(E)-4,7-diacetoxy-2-heptenylidene]-4-hydroxy-2-methylthio-4-(4-phenoxybutyl)-2-cyclopentenone (J) and 4 mg (yield 17%) of 5-[(E)-4,7-diacetoxy-2-heptenylidene]-4-acetoxy-2-methylthio-4-(4-phenoxybutyl)-2-cyclopentenone (K).

Spectrum data
$^1$H-NMR CDCl$_3$ δ
(J) 1.1–2.1 (11H, m), 2.01 (3H, s), 2.13 (3H, s), 2.36 (3H, s), 3.6–4.5 (5H, m), 6.0–6.5 (1H, m), 6.69 (1H, s), 6.7–7.2 (4H, m), 7.2–7.5 (3H, m).
(K) 1.1–2.1 (10H, m), 2.01 (3H, s), 2.04 (3H, s), 2.13 (3H, s), 2.35 (3H, s), 3.6–4.5 (5H, m), 6.0–6.5 (1H, m), 6.64 (1H, s), 6.7–7.2 (4H, m) 7.2–7.5 (3H, m).

EXAMPLE 111

Synthesis of 2-methylthio-5-(6-carboxyhexylidene)-4-hydroxy-4-octyl-2-cyclopentenone

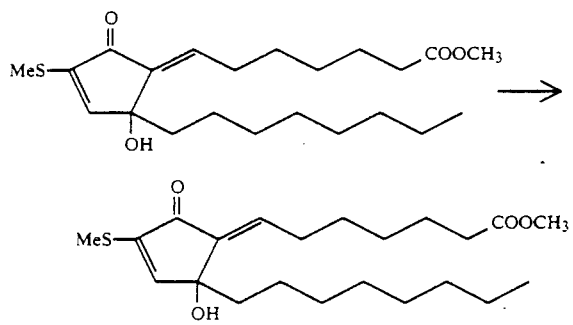

To a solution of 16 mg of 2-methylthio-4-hydroxy-5-(6-methoxycarbonylhexylidene)-4-octyl-2-cyclopentenone obtained in Example 101, dissolved in 1 ml of acetone, 11 ml of 0.1M phosphate buffer of pH 8 was added. Under stirring, 1.5 mg of pig liver esterase was added, and the mixture was stirred at 30–35° C. for 130 hours. After the mixture was adjusted to pH 4 with 0.1N hydrochloric acid, ammonium sulfate was added to saturation and the mixture was filtered with addition of ethyl acetate. The filtrate was extracted with ethyl acetate, the organic layers were combined and washed with saturated aqueous sodium chloride. After drying over anhydrous magnesium sulfate, filtration and concentration, the concentrate was subjected to silica gel column chromatography to give 7.7 mg (yield 47%) of 2-methylthio-5-(6-carboxyhexylidene)-4-hydroxy-4-octyl-2-cyclopentenone.

Spectrum data
$^1$H-NMR CDCl$_3$ δ
0.86 (3H, t, J=5.7 Hz), 1.1–2.2 (22H, m), 2.2–2.5 (2H, m), 2.36 (3H, s), 2.5–3.0 (2H, m), 6.5–6.9 (2H, m).

EXAMPLE 112

Evaluation of antitumor activity

Cancer cells were grown in an RPMI 1640 culture medium containing 10% of fetal calf serum.

The compound to be tested was dissolved in 99.5% ethanol and was added to the medium so that the final concentration of the ethanol was 0.1% or less. As a control, 0.1% ethanol was used. L1210 cancer cells were inoculated at a concentration of $1 \times 10^5$ cells/ml in the medium and were grown for 4 days. The number of live cells was determined by trypan blue staining.

The results are shown in Table 10.

TABLE 10

| Compound to be tested | | IC$_{50}$ (μg/ml) |
|---|---|---|
| | 2-methylthio-5-(6-methoxycarbonyl-hexylidene)-4-(3-hydroxy-1-octenyl)-2-cyclopentenone | 5.0 |
| | 2-methylsulfinyl-5-(6-methoxycarbonyl-hexylidene)-4-(3-hydroxy-1-octenyl)-2-cyclopentenone | 4.0 |
| | 2-methylsulfinyl-5-[(E)-4,7-dihydroxy-2-heptenylidene]-4-(4-phenoxybutyl)-4-hydroxy-2-cyclopentenone | 1.0 |
| | 2-methylsulfonyl-5-[(E)-4,7-dihydroxy-2-heptenylidene]-4-(4-phenoxybutyl)-4-hydroxy-2-cyclopentenone | 2.0 |

TABLE 10-continued

| Compound to be tested | | $IC_{50}$ (µg/ml) |
|---|---|---|
| 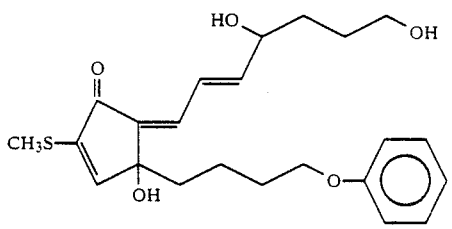 | 2-methylthio-5-[(Z)-4,7-dihydroxy-2-heptenylidene]-4-(4-phenoxybutyl)-4-hydroxy-2-cyclopentenone | 1.2 |
| 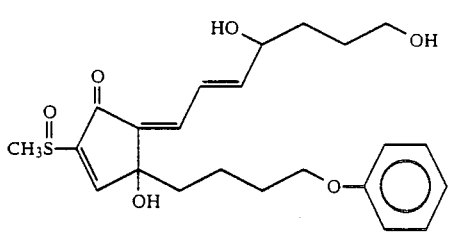 | 2-methylsulfinyl-5-[(Z)-4,7-dihydroxy-2-heptenylidene]-4-(4-phenoxybutyl)-4-hydroxy-2-cyclopentenone | 1.0 |
| 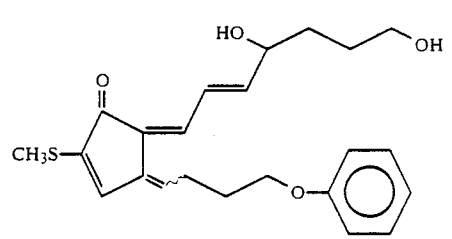 | 2-methylthio-5-[(Z)-4,7-dihydroxy-2-heptenylidene]-4-(4-phenoxybutylidene)-2-cyclopentenone | 3.5 |
| 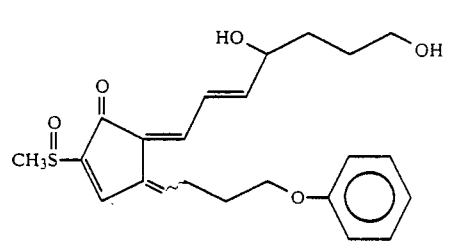 | 2-methylsulfinyl-5-[(Z)-4,7-dihydroxy-2-heptenylidene]-4-(4-phenoxybutylidene)-2-cyclopentenone | 0.1 |

EXAMPLE 113

Determination (1) of bone formation activity

Human osteoblast (SAM-1, 12PDL) was cultured in α-MEM containing 10% fetal bovine serum, and when a stable growth was attained, a predetermined concentration of the compound was added in the presence of 2 mM α-glycerophosphoric acid salt, followed by treatment for 25 days. The cell layer was washed with Hank's solution and the alkali phosphatase activity then measured by absorption at $OD_{410}$. Next, calcium and phosphorus were extracted with a 5% perchloric acid solution and quantitated, and DNA was extracted with 5% perchloric acid at 90° C., and the weight thereof quantitated. These evaluations were conducted according to the methods of Koshihara et al (Biochemical and Biophysical Research Communication Vol 145, No. 2, 1987, p. 651). The results are shown in Table 11.

TABLE 11

| Measurement of alkali phosphatase (ALP), calcium (Ca), phosphorus (P) per DNA | | | |
|---|---|---|---|
| Compound | ALP OD 410 nm/ µg DNA | Ca µg/µg DNA | P µg/µg DNA |
| Control | 1.148 ± 0.050 | 0.386 ± 0.245 | 1.528 ± 0.316 |

TABLE 11-continued

Measurement of alkali phosphatase (ALP), calcium (Ca), phosphorus (P) per DNA

| Compound | | ALP OD 410 nm/ μg DNA | Ca μg/μg DNA | P μg/μg DNA |
|---|---|---|---|---|
| 2-methylthio-5-[(Z)-4,7-dihydroxy-2-heptenylidene]-4-(4-phenoxybutyl)-4-hydroxy-2-cyclopentenone | $10^{-7}$ M | 0.333 ± 0.039 $p < 0.001$ | 8.847 ± 1.485 $p < 0.05$ | 5.270 ± 0.144 $p < 0.001$ |
| | $10^{-6}$ M | 1.447 ± 0.268 $p < 0.001$ | 29.410 ± 1.263 $p < 0.001$ | 15.743 ± 0.630 $p < 0.01$ |

EXAMPLE 114

Determination (2) of bone formation activity

Human osteoblast (KK-3, 18PDL) was cultured in α-MEM containing 10% fetal bovine serum, and when a stable growth was attained, a predetermined concentration of the compound was added in the presence of 2 mM α-glycerophosphoric acid salt, followed by treatment for 14 days. The cell layer was washed with physiological salt solution and the alkali phosphatase activity then measured by absorption at $OD_{415}$. Then, calcium and phosphorus were extracted with a 2N hydrochloric acid solution and quantitated. The results are shown in Table 12.

EXAMPLE 115

Determination (3) of bone formation activity

Human osteoblast (KK-3, 18PDL) was cultured in α-MEM containing 10% fetal bovine serum, and when a stable growth was attained, a predetermined concentration of the compound was added in the presence of 2 mM α-glycerophosphoric acid salt, followed by treatment for 14 days. The cell layer was washed with a physioligical salt solution and the alkali phosphatase activity then measured by absorption at $OD_{415}$. Next, calcium and phosphorus were extracted with a 2N hydrochloric acid solution and quantitated.

The results are shown in Table 13.

TABLE 12

| Compound | | ALP OD 415 nm/dish | Ca μg/dish | P μg/dish |
|---|---|---|---|---|
| Control (No compound) | | 0.44 ± 0.12 | 106 ± 12 | 61 ± 10 |
| 2-methylthio-5-[(Z)-4,7-dihydroxy-2-heptenylidene]-4-(4-phenoxybutyl)-4-hydroxy-2-cyclopentenone | $10^{-8}$ M | 0.28 ± 0.06 | 84 ± 10 | 47 ± 6 |
| | $10^{-7}$ M | 0.48 ± 0.08 | 111 ± 9 | 63 ± 6 |
| | $10^{-6}$ M | 1.12 ± 0.31 | 168 ± 1 | 92 ± 2 |
| 2-methylthio-5-[(E)-4,7-dihydroxy-2-heptenylidene]-4-(4-phenoxybutyl)-4-hydroxy-2-cyclopentenone | $10^{-8}$ M | 0.24 ± 0.02 | 87 ± 6 | 47 ± 2 |
| | $10^{-7}$ M | 0.56 ± 0.08 | 114 ± 4 | 64 ± 3 |
| | $10^{-6}$ M | 0.97 ± 0.07 | 168 ± 9 | 93 ± 4 |

TABLE 13

| Compound | | ALP OD 415 nm/dish | Ca μg/dish | P μg/dish |
|---|---|---|---|---|
| Control (No compound) | | 0.72 ± 0.17 | 90 ± 8 | 51 ± 5 |
| 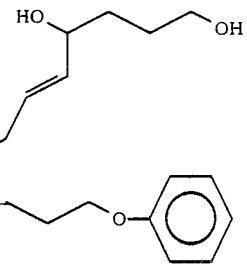<br>2-methylthio-5-[(Z)-4,7-dihydroxy-2-heptenylidene]-4-(4-phenoxybutylidene)-2-cyclopentenone | $10^{-7}$ M<br>$10^{-6}$ M | 0.69 ± 0.02<br>0.75 ± 0.17 | 110 ± 30<br>105 ± 5 | 60 ± 14<br>57 ± 1 |
| 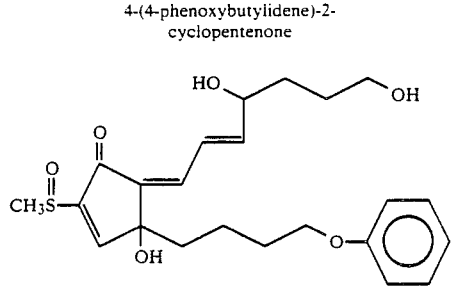<br>2-methylsulfinyl-5-[(Z)-4,7-dihydroxy-2-heptenylidene]-4-(4-phenoxybutylidene)-4-hydroxy-2-cyclopentenone | $10^{-7}$ M<br>$10^{-6}$ M | 0.81 ± 0.11<br>0.92 ± 0.9 | 89 ± 1<br>109 ± 7 | 52 ± 1<br>61 ± 4 |
| 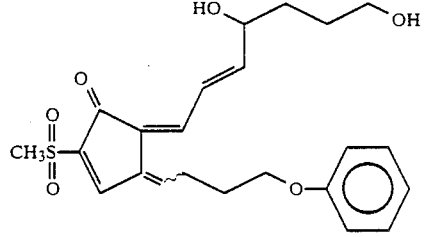<br>2-methylsulfonyl-5-[(Z)-4,7-dihydroxy-2-heptenylidene]-4-(4-phenoxybutylidene)-2-cyclopentenone | $10^{-7}$ M<br>$10^{-6}$ M | 0.94 ± 0.07<br>0.94 ± 0.11 | 85 ± 10<br>109 ± 3 | 48 ± 4<br>60 ± 0.5 |
| 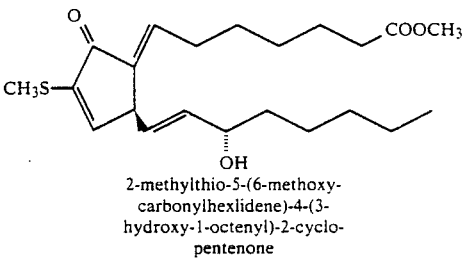<br>2-methylthio-5-(6-methoxycarbonylhexlidene)-4-(3-hydroxy-1-octenyl)-2-cyclopentenone | $10^{-7}$ M<br>$10^{-6}$ M | 0.73 ± 0.02<br>0.68 ± 0.10 | 78 ± 4<br>79 ± 8 | 46 ± 2<br>43 ± 4 |

We claim:

1. A 2-substituted-2-cyclopentenone represented by the formula (I):

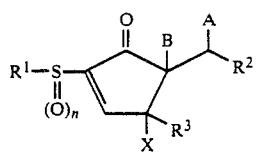

wherein A is a hydroxyl group or

and B is a hydrogen atom or A and B are absent and a double bond is present between the two carbon atoms to which A and B would be bound;

$R^1$ represents an alkyl group having 1 to 10 carbon atoms, an aralkyl group having 7 to 10 carbon atoms, or an aryl group having 6 to 10 carbon atoms or said alkyl, aralkyl or aryl group substituted with a hydroxyl group, a tri($C_1$-$C_7$)hydrocarbonsilyloxy group, a halogen atom, an alkoxy group, an acyloxy group, an acyl group, an alkoxycarbonyl group, or a carboxyl group;

$R^2$ represents an aliphatic hydrocarbon group having from 1 to 10 carbon atoms or an aliphatic hydrocarbon group having from 1 to 10 carbon atoms substituted with —COOR$^5$, wherein $R^5$ represents a hydrogen atom, an alkyl group having 1 to 10 carbon atoms or one equivalent cation; —OR$^6$, wherein $R^6$ represents a hydrogen atom, an acyl group having 2 to 7 carbon atoms, a tri($C_1$-$C_7$)hydrocarbonsilyloxy group, a methoxymethyl group, a 1-ethoxyethyl group, a 2-methoxy-2-propyl group, a 2-ethoxy-2-propyl group, a 2-methoxyethoxy-methyl group, a tetrahydropyran-2-yl group, a tetrahydrofuran-2-yl group, a 6,6-dimethyl-3-oxa-2-oxo-bicyclo[3.1.0]-hexan-4-yl group, an aromatic hydrocarbon group which may be substituted with a halogen atom, a hydroxyl group, a tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, or an alkoxy group having 1 to 4 carbon atoms; an aromatic hydrocarbon group which may be substituted with a halogen atom, a hydroxyl group, a tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, or an alkoxy group having 1 to 4 carbon atoms; or an alicyclic group which may be substituted with a halogen atom, a hydroxyl group, a tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, or an alkoxy group having 1 to 4 carbon atoms;

$R^3$ represents an aliphatic hydrocarbon group having from 1 to 10 carbon atoms or an aliphatic hydrocarbon group having from 1 to 10 carbon atoms substituted with —COOR$^5$, wherein $R^5$ represents a hydrogen atom, an alkyl group having 1 to 10 carbon atoms or one equivalent cation; —OR$^6$, wherein $R^6$ represents a hydrogen atom, an acyl group having 2 to 7 carbon atoms, a tri($C_1$-$C_7$)hydrocarbonsilyloxy group, a methoxymethyl group, a 1-ethoxyethyl group, a 2-methoxy-2-propyl group, a 2-ethoxy-2-propyl group, a 2-methoxyethoxy-methyl group, a tetrahydropyran-2-yl group, a tetrahydrofuran-2-yl group, a 6,6-dimethyl-3-oxa-2-oxo-bicyclo[3.1.0]-hexan-4-yl group, an aromatic hydrocarbon group which may be substituted with a halogen atom, a hydroxyl group, a tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, or an alkoxy group having 1 to 4 carbon atoms; an aromatic hydrocarbon group which may be substituted with a halogen atom, a hydroxyl group, a tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, or an alkoxy group having 1 to 4 carbon atoms; or an alicyclic group which may be substituted with a halogen atom, a hydroxyl group, a tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, or an alkoxy group having 1 to 4 carbon atoms; wherein $R^3$ is attached via a single bond, and X represents a hydrogen atom, a hydroxyl group, an alkoxy group, a tri($C_1$-$C_7$)hydro-carbonsilyloxy group, an acetal group selected from the group consisting of a methoxymethoxy group, a 1-ethoxyethoxy group, a 2-methoxyethoxymethoxy group, and a tetrahydropyran-2-yloxy group or an acyloxy group or $R^3$ is attached via a double bond and X is absent; and m and n represent 0, 1 or 2.

2. A 2-substituted-2-cyclopentenone as claimed in claim 1 represented by the formula (I-a):

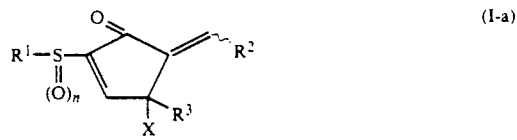

wherein $R^1$, $R^2$, $R^3$, X and n are as defined in claim 1; and the representation ∿ represents that the substituent bonded to the double bond is in an E-arrangement or a Z-arrangement or a mixture thereof at any desired ratio.

3. A 2-substituted-2-cyclopentenone as claimed in claim 1 represented by the formula (I-b):

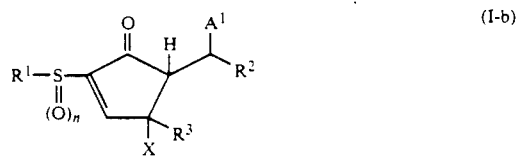

wherein $A^1$ is a hydroxyl group or

$R^1$, $R^2$, $R^3$, X, m and n are the same as defined in claim 1.

4. A 2-substituted-2-cyclopentenone as claimed in claim 1 represented by the formula (I-a-1):

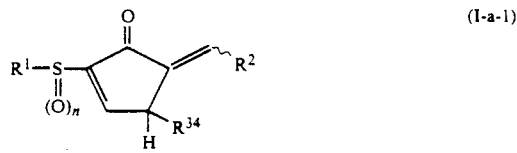

wherein $R^1$, $R^2$, n are as defined in claim 1, the representation ∿ represents that the substituent bonded to the double bond is in an E-arrangement or a Z-arrangement or a mixture thereof at any desired ratio and $R^{34}$ has the same meaning as $R^2$.

5. A 2-substituted-2-cyclopentenone as claimed in claim 1 represented by the formula (I-a-2):

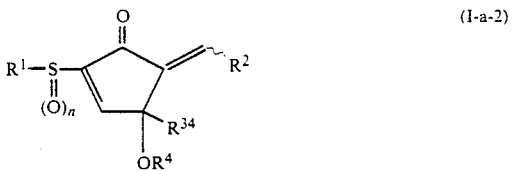
(I-a-2)

wherein $R^1$, $R^2$, and n are as defined in claim 1, $R^{34}$ has the same meaning as $R^2$, and the representation ⁓ represents that the substituent bonded to the double bond is in an E-arrangement or a Z-arrangement or a mixture thereof at any desired ratio;

$R^4$ represents a hydrogen atom, an alkyl group having 1 to 3 carbon atoms, a tri($C_1$-$C_7$)hydrocarbonsilyl group, a methoxymethyl group, a 1-ethoxy ethyl group, a 2-methoxyethoxymethyl group, a tetrahydropyran-2-yl group, or an acyl group having 1 to 4 carbon atoms.

6. A 2-substituted-2-cyclopentenone as claimed in claim 1 represented by the formula (I-a-3'):

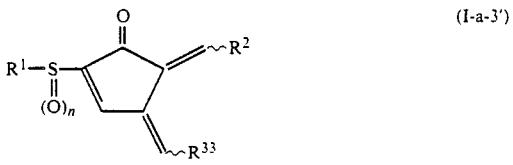
(I-a-3')

wherein $R^1$, $R^2$ and n are as defined in claim 1, the representation ⁓ represents that the substituent bonded to the double bond is in an E-arrangement or a Z-arrangement or a mixture thereof at any desired ratio; and $R^{33}$ represents a hydrogen atom, an aliphatic hydrocarbon group having from 1 to 9 carbon atoms or an aliphatic hydrocarbon group having from 1–9 carbon atoms substituted with —COOR$^5$, where $R^5$ represents a hydrogen atom, an alkyl group having 1 to 10 carbon atoms or one equivalent cation; —OR$^6$, where $R^6$ is an acyl group having 2 to 7 carbon atoms, a tri($C_1$-$C_7$)hydrocarbonsilyloxy group, a methoxymethyl group, a 1-ethoxyethyl group, a 2-methoxy-2-propyl group, a 2-ethoxy-2-propyl group, a 2-methoxyethoxy-methyl group, a tetrahydropyran-2-yl group, a tetrahydrofuran-2-yl group, a 6,6-dimethyl-3-oxa-2-oxobicyclo[3.1.0]-hexan-4-yl group, an aromatic hydrocarbon group which may be substituted with a halogen atom, a hydroxyl group, a tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, or an alkoxy group having 1 to 4 carbon atoms; an aromatic hydrocarbon group which may be substituted with a halogen atom, a hydroxyl group, a tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, or an alkoxy group having 1 to 4 carbon atoms; or an alicyclic group which may be substituted with a halogen atom, a hydroxyl group, a tri($C_1$-$C_7$)hydrocarbonsilyloxy group, a carboxyl group, an acyloxy group having 2 to 7 carbon atoms, an acyl group having 2 to 7 carbon atoms, an alkoxycarbonyl group having 2 to 5 carbon atoms, an alkyl group having 1 to 4 carbon atoms, or an alkoxy group having 1 to 4 carbon atoms.

7. A 2-substituted-2-cyclopentenone as claimed in claim 1 represented by the formula (I-b-1):

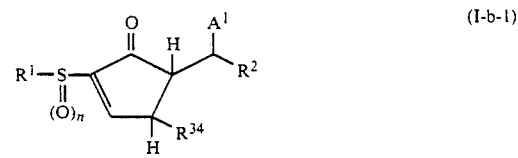
(I-b-1)

wherein $A^1$ is a hydroxyl group or

wherein m represents 0, 1 or 2, $R^1$, $R^2$ and n are as defined in claim 1, and $R^{34}$ has the same meaning as $R^2$.

8. 2-substituted-2-cyclopentenone as claimed in claim 7 wherein $A^1$ is a hydroxyl group.

9. 2-substituted-cyclopentenone as claimed in claim 1 represented by the formula (I-b-2):

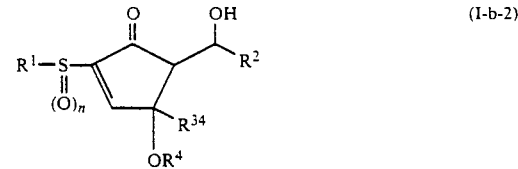
(I-b-2)

wherein $R^1$, $R^2$ and n are as defined in claim 1, $R^{34}$ has the same meaning as $R^2$, and $R^4$ represents a hydrogen atom, an alkyl group having 1 to 3 carbon atoms, a tri($C_1$-$C_7$)hydrocarbonsilyl group, a methoxymethyl group, a 1-ethoxy ethyl group, a 2-methoxyethoxymethyl group, a tetrahydropyran-2-yl group, or an acyl group having 1 to 4 carbon atoms.

10. 2-substituted-2-cyclopentenone as claimed in claim 1, wherein $R^1$ is a substituted or unsubstituted alkyl group having 1 to 5 carbon atoms.

11. 2-substituted-cyclopentenone as claimed in claim 1, wherein $R^1$ is methyl.

12. 2-substituted-2-cyclopentenone as claimed in claim 1, wherein the substituent on $R^2$ is a methoxycarbonyl group, a hydroxyl group, an acetoxy group or a t-butyldimethylsilyloxy group.

13. 2-substituted-2-cyclopentenone as claimed in claim 1, wherein the substituents when $R^3$ is substituted are a phenoxy group, a hydroxy group, a tetrahydropyran-2-yloxy group, or a t-butyldimethylsilyloxy group.

14. 2-substituted-2-cyclopentenone as claimed in claim 1, wherein X is a hydroxyl group, a methoxy group, an acetoxy group or a trimethylsilyloxy group.

15. 2-substituted-2-cyclopentenone as claimed in claim 1, wherein X is a hydrogen atom, a hydroxyl group, a methoxy group, an ethoxy group, a trimethylsilyloxy group, or an acetoxy group.

16. An antitumor agent containing, as an essential component, at least one 2-substituted-2-cyclopentenone of claim 1 and a pharmaceutically acceptable carrier or excipient.

17. A bone formation accelerator containing, as an essential component, at least one 2-substituted-2-cyclopentenone of claim 1 and a pharmaceutically acceptable carrier or excipient.

* * * * *